United States Patent
Liu

(10) Patent No.: US 9,412,949 B2
(45) Date of Patent: Aug. 9, 2016

(54) FLUORESCENT CONJUGATED POLYMERS WITH A BODIPY-BASED BACKBONE AND USES THEREOF

(75) Inventor: Haiying Liu, Houghton, MI (US)

(73) Assignee: MICHIGAN TECHNOLOGICAL UNIVERSITY, Houghton, MI (US)

(*) Notice: Subject to any disclaimer, the term of this patent is extended or adjusted under 35 U.S.C. 154(b) by 1078 days.

(21) Appl. No.: 13/141,158

(22) PCT Filed: Dec. 23, 2009

(86) PCT No.: PCT/US2009/069415
§ 371 (c)(1),
(2), (4) Date: Sep. 14, 2011

(87) PCT Pub. No.: WO2010/075514
PCT Pub. Date: Jul. 1, 2010

(65) Prior Publication Data
US 2012/0070382 A1 Mar. 22, 2012

Related U.S. Application Data

(60) Provisional application No. 61/140,529, filed on Dec. 23, 2008.

(51) Int. Cl.
| | |
|---|---|
| *A61K 8/72* | (2006.01) |
| *H01L 51/00* | (2006.01) |
| *B82Y 10/00* | (2011.01) |
| *C08G 61/12* | (2006.01) |
| *A61K 31/785* | (2006.01) |
| *A61K 31/74* | (2006.01) |
| *A61K 31/787* | (2006.01) |
| *H01L 51/42* | (2006.01) |

(52) U.S. Cl.
CPC ............. *H01L 51/0041* (2013.01); *B82Y 10/00* (2013.01); *C08G 61/124* (2013.01); *H01L 51/008* (2013.01); *H01L 51/0035* (2013.01); *A61K 31/74* (2013.01); *A61K 31/785* (2013.01); *A61K 31/787* (2013.01); *C08G 2261/3241* (2013.01); *H01L 51/0047* (2013.01); *H01L 51/4253* (2013.01)

(58) Field of Classification Search
None
See application file for complete search history.

(56) References Cited

U.S. PATENT DOCUMENTS

| | | | |
|---|---|---|---|
| 5,994,063 A | 11/1999 | Metzker et al. | |
| 6,001,999 A | 12/1999 | Wolfbeis et al. | |
| 6,420,648 B1 | 7/2002 | Lindsey | |
| 2006/0121623 A1 | 6/2006 | He et al. | |
| 2008/0061684 A1 | 3/2008 | Saitou et al. | |

OTHER PUBLICATIONS

Peng et al. "Polymers with High Electron Affinities forLight-Emitting Diodes" Chem. Mater. 1998, vol. 10, pp. 1785-1788.*
Bonardi et al., "Fine-tuning of yellow or red photo—and electroluminescence of functional difluoro-boradiazaindacene films," Advanced Functional Materials, 2008, vol. 18, pp. 401-413.
Donuru et al., "Deep-red emissive conjugated poly(2,6-BODIFY-ethynylene)s bearing alkyl side chains," Journal of Polymer Science, Part A: Polymer Chemistry, 2009, vol. 47, No. 20, pp. 5354-5366.
Donuru et al., "Synthesis and optical properties of red and deep-red emissive polymeric and copolymeric BODIPY dyes," Chemistry of Materials, 2009, vol. 21, No. 10, pp. 2130-2138.
Meng et al., "Color tuning of polyfluorene emission with BODIPY monomers," Macromolecules, 2009, Meng et al., "Color tuning of polyfluorene emission with BODIPY monomers," Macromolecules (2009) 42(6):1995-2001. ol. 42, No. 6, pp. 1995-2001.
Nagai et al., "Highly luminescent BODIPY-based organoboron polymer exhibiting supramolecular self-assemble structure," J. American Chemical Society, 2008, vol. 130, No. 46, pp. 15276-15278.
Zhu et al., "Efficient tuning nonlinear optical properties: synthesis and characterization of a series of novel poly (aryleneethynylen)s co-containing BODIPY," Journal of Polymer Science: Part A: Polymer Chemistry, 2008, vol. 46, pp. 7401-7410.
International Search Report and Written Opinion for Application No. PCT/US09/69412 dated Mar. 10, 2010 (7 pages).
International Search Report and Written Opinion for Application No. PCT/US09/69415 dated Mar. 22, 2010 (7 pages).

* cited by examiner

*Primary Examiner* — James Rogers
(74) *Attorney, Agent, or Firm* — Michael Best & Friedrich LLP

(57) ABSTRACT

The present invention provides various fluorescent conjugated polymers with a BODIPY-based backbone. The invention also provides methods of using the polymers of the invention, such as for imaging and detection of cells, tumors, bacteria and viruses.

4 Claims, 52 Drawing Sheets

Scheme 8. Synthetic route to conjugated glycopoly(F-BODIPY-ethynylene)s.

Scheme 9. Synthetic route to Cascade-type conjugated glycopoly(C- or E-BODIPY-ethynylene)s.

Scheme 10. Synthetic route to near-infrared emissive conjugated glycopoly(F-, C- and E-BODIPY-vinylene)s.

Scheme 11. Synthetic route to near-infrared emissive conjugated glycopoly(BODIPY-ethynylene)s.

Scheme 12. Synthetic route to BODIPY-based fluorescent conjugated glyco-copolymers.

FLUORESCENT CONJUGATED POLYMERS WITH A BODIPY-BASED BACKBONE AND USES THEREOF

CROSS-REFERENCE TO RELATED APPLICATIONS

This application is a national stage filing under 35 U.S.C. 371 of International Application No. PCT/US2009/069415 filed Dec. 23, 2009, which claims the benefit of U.S. Provisional Application Ser. No. 61/140,529 filed Dec. 23, 2008, which are hereby incorporated by reference in their entireties.

STATEMENT OF GOVERNMENT SUPPORT

This invention was made with United States government support from the USDA Cooperative State Research, Education, and Extension Service—Nanoscale Science and Engineering for Agriculture and Food Systems, National Research Initiative Grant no. 2007-35603-17740. The United States government has certain rights in this invention.

BACKGROUND

4-Difluoro-4-bora-3a,4a-diaza-s-indacene (BODIPY) derivatives are becoming increasingly popular for promising applications in biological probes, suproamolecular fluorescent gels, solar cells and sensors because BODIPY dyes possess elevated chemical and photostability, relatively high absorption coefficients and fluorescence quantum yields, and show narrow absorption and emission bands with high peak intensities.

SUMMARY

Among other things, the present invention provides a polymer according to formula (I):

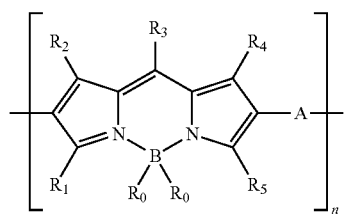

(I)

wherein each -A- is independently selected from -AR—, ═══AR═══, ═══AR, ═══, or ═══AR═══;

wherein each -AR— is independently selected from arylene or heteroarylene;

wherein each $R_3$ is independently selected from R, alkyl, aryl or heteroaryl wherein each $R_2$ and $R_4$ are independently selected from alkyl or H;

wherein each $R_1$ and $R_5$ are independently selected from hydrogen, alkyl, or ═══AR;

wherein each $R_0$ is —F, —OR, —R, aryl, heteroaryl, ═══R, ═══-Aryl, or ═══-Heteroaryl;

wherein each R is independently selected from —H, $-(CH_2)_mR_{10}$, $-(CH_2)_mCOO(CH_2)_pCH_3$, $-(CH_2)_mSO_3Na$, $-(CH_2)_mPO_3Na$, $-(CH_2)_mN(CH_3)_3^+Br^-$, $-(CH_2)_mCOH(CH_2)_pCH_3$, $-(CH_2)_mOR_{10}$, $-(CH_2)_mOR_8$, $-CH_2CH_2(OCH_2CH_2)_mOR_{10}$, $-CH_2CH_2(OCH_2CH_2)_mOR_8$, $-CH_2CH_2(OCH_2CH_2)_mSR_8$, or

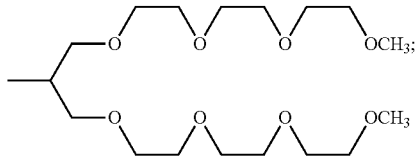 [SMILES: COCCOCCOCCOCC(C)COCCOCCOCCOC]

and wherein each $R_8$ is independently selected from a carbohydrate residue;

and wherein each $R_{10}$ is independently selected from hydrogen, alkyl, heteroalkyl, hydroxy, amino, ammonic acid, thiol, carboxylic acid, nitrile, azide, ethynylene, halo, and tosylate;

wherein m is from 0 to 100;

wherein n is from 2 to 300 and wherein p is from 0 to 20.

The invention further provides a polymer according to formula (II):

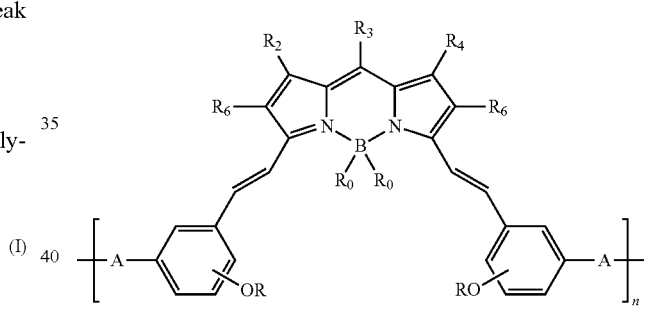

(II)

wherein each -A- is independently selected from -AR—, ═══AR═══, ═══AR, ═══, or ═══AR═══;

wherein each -AR— is independently selected from arylene or heteroarylene;

wherein each $R_3$ is independently selected from R, alkyl, aryl or heteroaryl wherein each $R_2$ and $R_4$ are independently selected from alkyl or H;

wherein each $R_6$ is independently selected from H or alkyl;

wherein each $R_0$ is —F, —OR, —R, aryl, heteroaryl, ═══R, ═══-Aryl, or ═══-Heteroaryl;

wherein each R is independently selected from —H, $-(CH_2)_mCOO(CH_2)_pCH_3$, $-(CH_2)_mSO_3Na$, $-(CH_2)_mPO_3Na$, $-(CH_2)_mN(CH_3)_3^+Br^-$, $-(CH_2)_mCOH(CH_2)_pCH_3$, $-(CH_2)_mOR_{10}$, $-(CH_2)_mOR_8$, $-CH_2CH_2(OCH_2CH_2)_mOR_{10}$, $-CH_2CH_2(OCH_2CH_2)_mOR_8$, $-CH_2CH_2(OCH_2CH_2)_mSR_8$, or

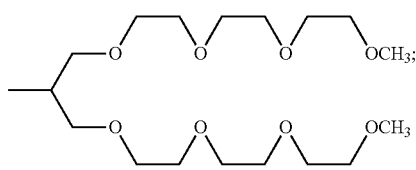 [SMILES: COCCOCCOCCOCC(C)COCCOCCOCCOC]

and wherein each $R_8$ is independently selected from a carbohydrate residue;

and wherein each $R_{10}$ is independently selected from hydrogen, alkyl, heteroalkyl, hydroxy, amino, ammonic acid, thiol, carboxylic acid, nitrile, azide, ethynylene, halo, and tosylate;

wherein m is from 0 to 100;

wherein n is from 2 to 300 and wherein p is from 0 to 20.

In addition, the invention provides a polymer according to formula (III):

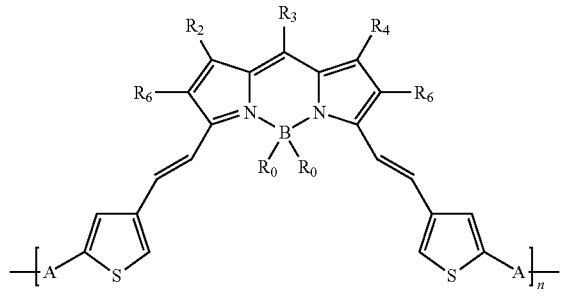

wherein each -A- is independently selected from -AR—, —≡—AR—≡—, —≡—AR—≡—≡—, or —≡—≡—AR—≡—≡—;

wherein each -AR— is independently selected from arylene or heteroarylene;

wherein each $R_3$ is independently selected from R, alkyl, aryl or heteroaryl wherein each $R_2$ and $R_4$ are independently selected from alkyl or H;

wherein each $R_6$ is independently selected from H or alkyl;

wherein each $R_0$ is —F, —OR, —R, aryl, heteroaryl, —≡—R, —≡—-Aryl, or —≡—-Heteroaryl;

wherein each R is independently selected from —H, —$(CH_2)_m R_{10}$, —$(CH_2)_m COO(CH_2)_p CH_3$, —$(CH_2)_m SO_3Na$, —$(CH_2)_m PO_3Na$, —$(CH_2)_m N(CH_3)_3^+ Br^-$, —$(CH_2)_m COH(CH_2)_p CH_3$, —$(CH_2)_m OR_{10}$, —$(CH_2)_m OR_8$, —$CH_2CH_2(OCH_2CH_2)_m OR_{10}$, —$CH_2CH_2(OCH_2CH_2)_m OR_8$, —$CH_2CH_2(OCH_2CH_2)_m SR_8$, or

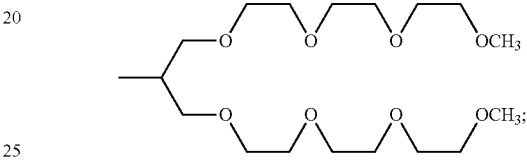

and wherein each $R_8$ is independently selected from a carbohydrate residue;

and wherein each $R_{10}$ is independently selected from hydrogen, alkyl, heteroalkyl, hydroxy, amino, ammonic acid, thiol, carboxylic acid, nitrile, azide, ethynylene, halo, and tosylate;

wherein m is from 0 to 100;

wherein n is from 2 to 300 and wherein p is from 0 to 20.

The invention also provides a polymer according to formula (IV):

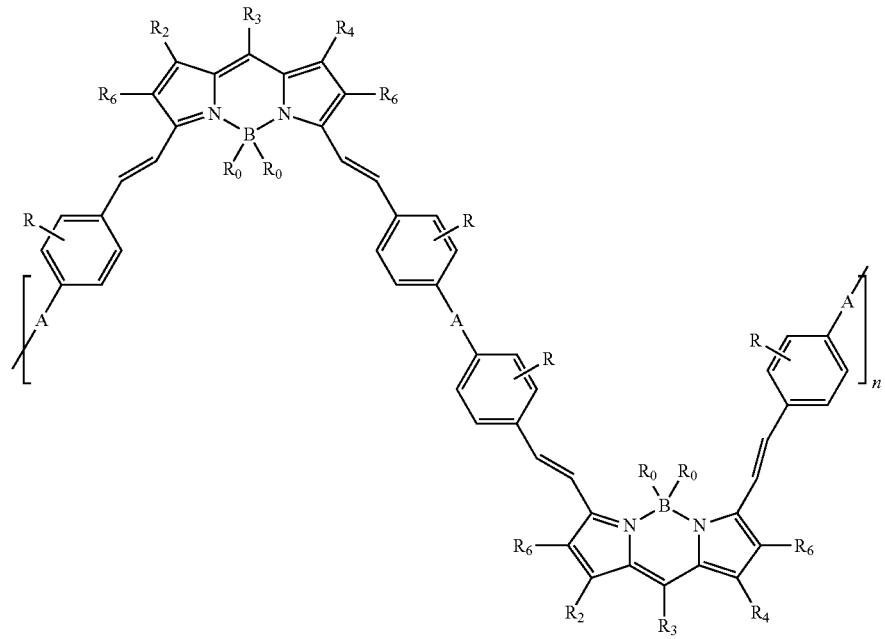

wherein each -A- is independently selected from -AR—, ══════AR══════, ══════AR══════, or ══════AR══════;

wherein each -AR— is independently selected from arylene or heteroarylene;

wherein each $R_3$ is independently selected from R, alkyl, aryl or heteroaryl wherein each $R_2$ and $R_4$ are independently selected from alkyl or H;

wherein each $R_6$ is independently selected from H or alkyl;

wherein each $R_0$ is —F, —OR, —R, aryl, heteroaryl, ══════R, ══════-Aryl, or ══════-Heteroaryl;

wherein each R is independently selected from —H, —$(CH_2)_mR_{10}$, —$(CH_2)_mCOO(CH_2)_pCH_3$, —$(CH_2)_mSO_3Na$, —$(CH_2)_mPO_3Na$, —$(CH_2)_mN(CH_3)_3^+Br^-$, —$(CH_2)_mCOH(CH_2)_pCH_3$, —$(CH_2)_mOR_{10}$, —$(CH_2)_mOR_8$, —$CH_2CH_2(OCH_2CH_2)_mOR_{10}$, —$CH_2CH_2(OCH_2CH_2)_mOR_8$, —$CH_2CH_2(OCH_2CH_2)_mSR_8$, or

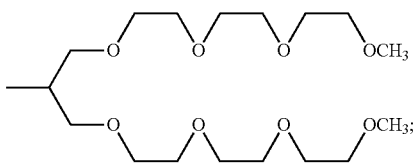 [SMILES: COCCOCCOCCOCC(C)COCCOCCOCCOC]

and wherein each $R_8$ is independently selected from a carbohydrate residue;

and wherein each $R_{10}$ is independently selected from hydrogen, alkyl, heteroalkyl, hydroxy, amino, ammonic acid, thiol, carboxylic acid, nitrile, azide, ethynylene, halo, and tosylate;

wherein m is from 0 to 100;
wherein n is from 2 to 300 and
wherein p is from 0 to 20.

The invention further provides methods of using the above polymers including a method of enhancing medical imaging comprising administering an effective amount of a polymer to a subject in need of medical imaging and obtaining an image, wherein the amount of the polymer is sufficient to enhance an image compared to an image obtained in absence of the polymer.

Also, the invention provides a method of detecting the presence of a target in a sample comprising contacting the sample with a polymer which binds to the target and detecting fluorescence of the polymer.

In addition, the invention provides a method of monitoring drug delivery comprising administering a polymer to a subject and detecting fluorescence of the polymer in the subject, wherein the polymer is further functionalized with an active agent.

DETAILED DESCRIPTION

Figure 1:
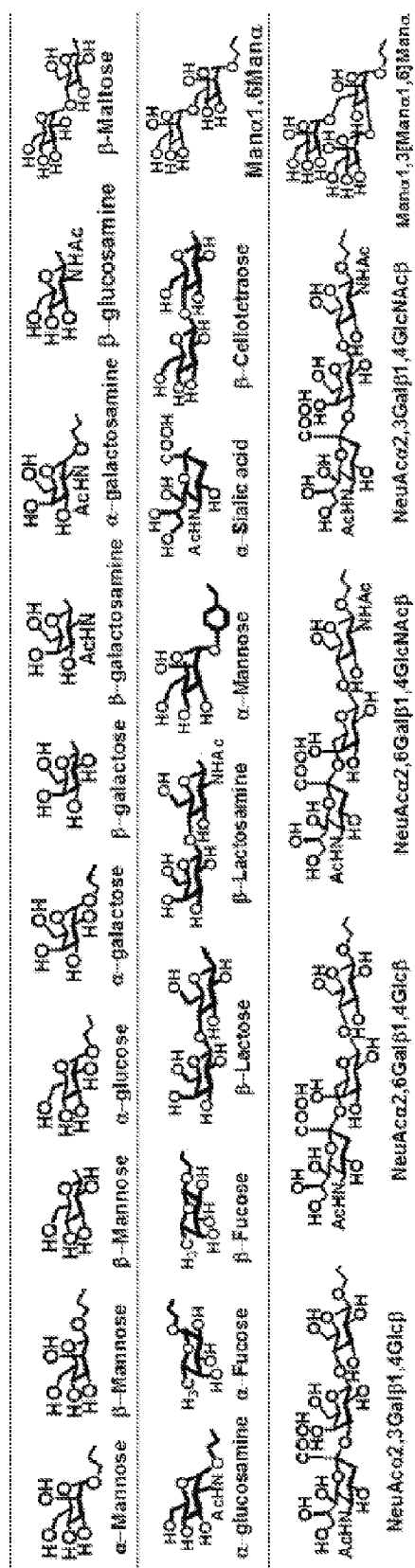
FIG. 1 shows various carbohydrate residues.
Figure 2A:
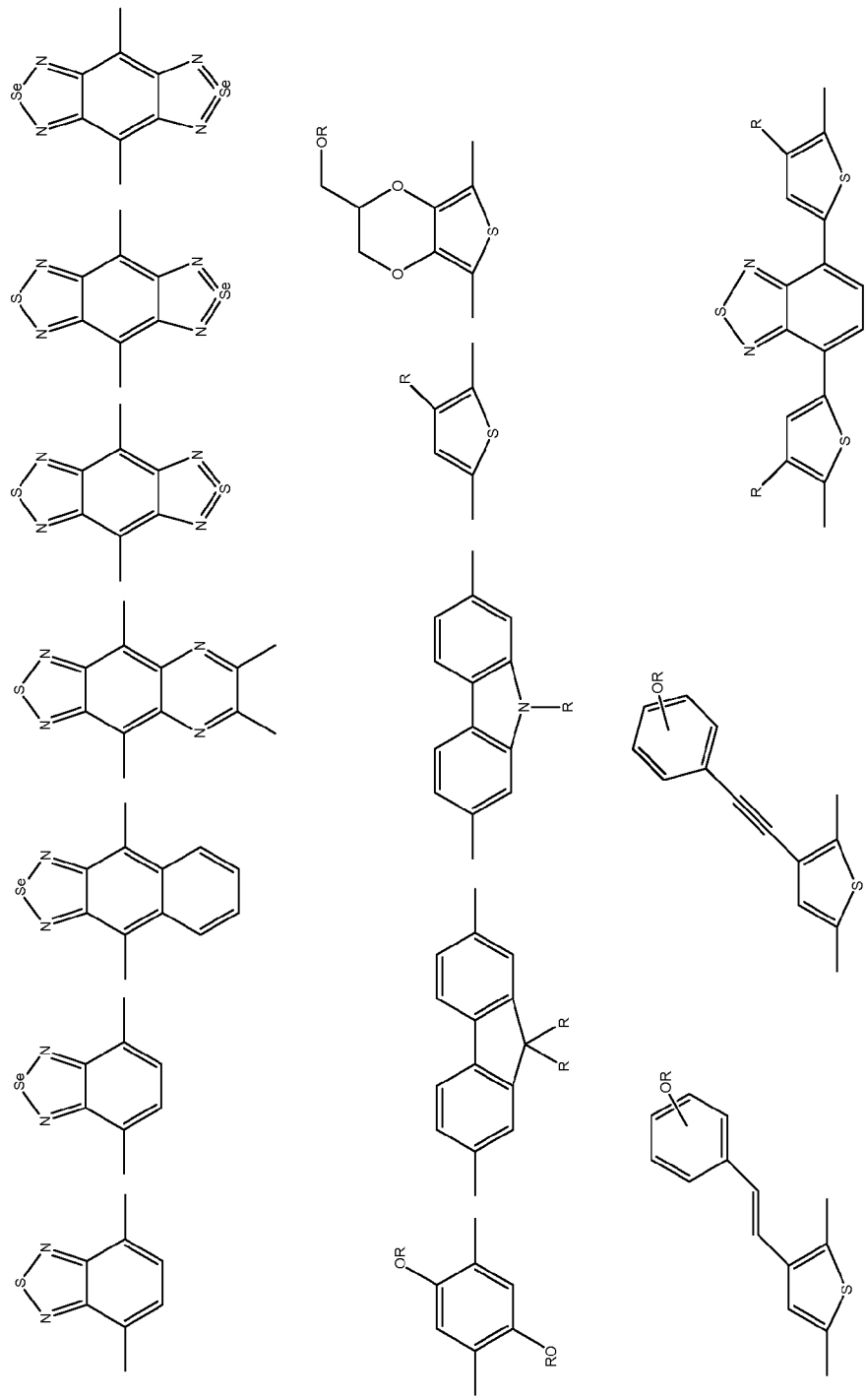
FIG. 2 shows various aryl groups.
Figure 2A:
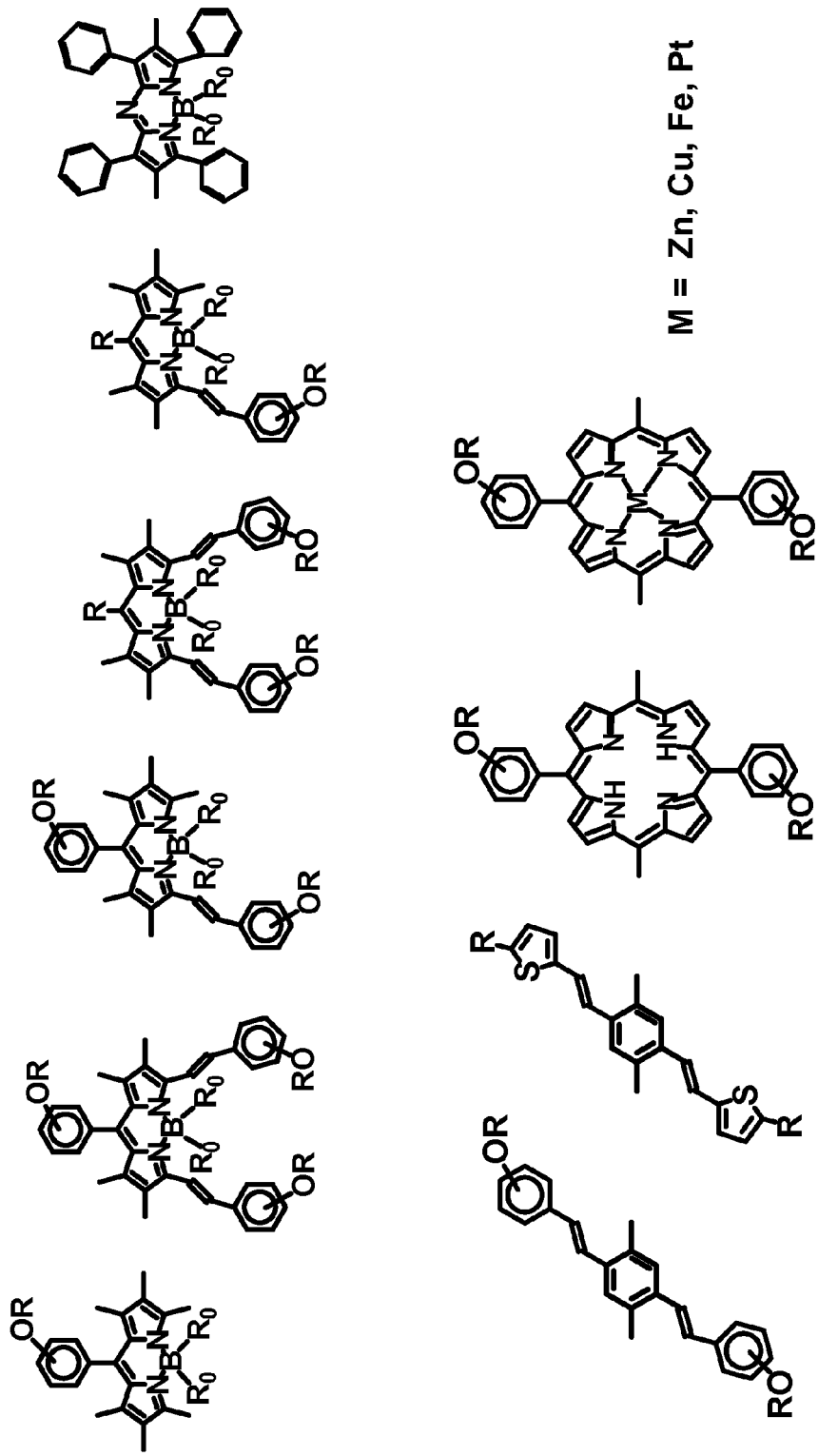
Figure 2B:
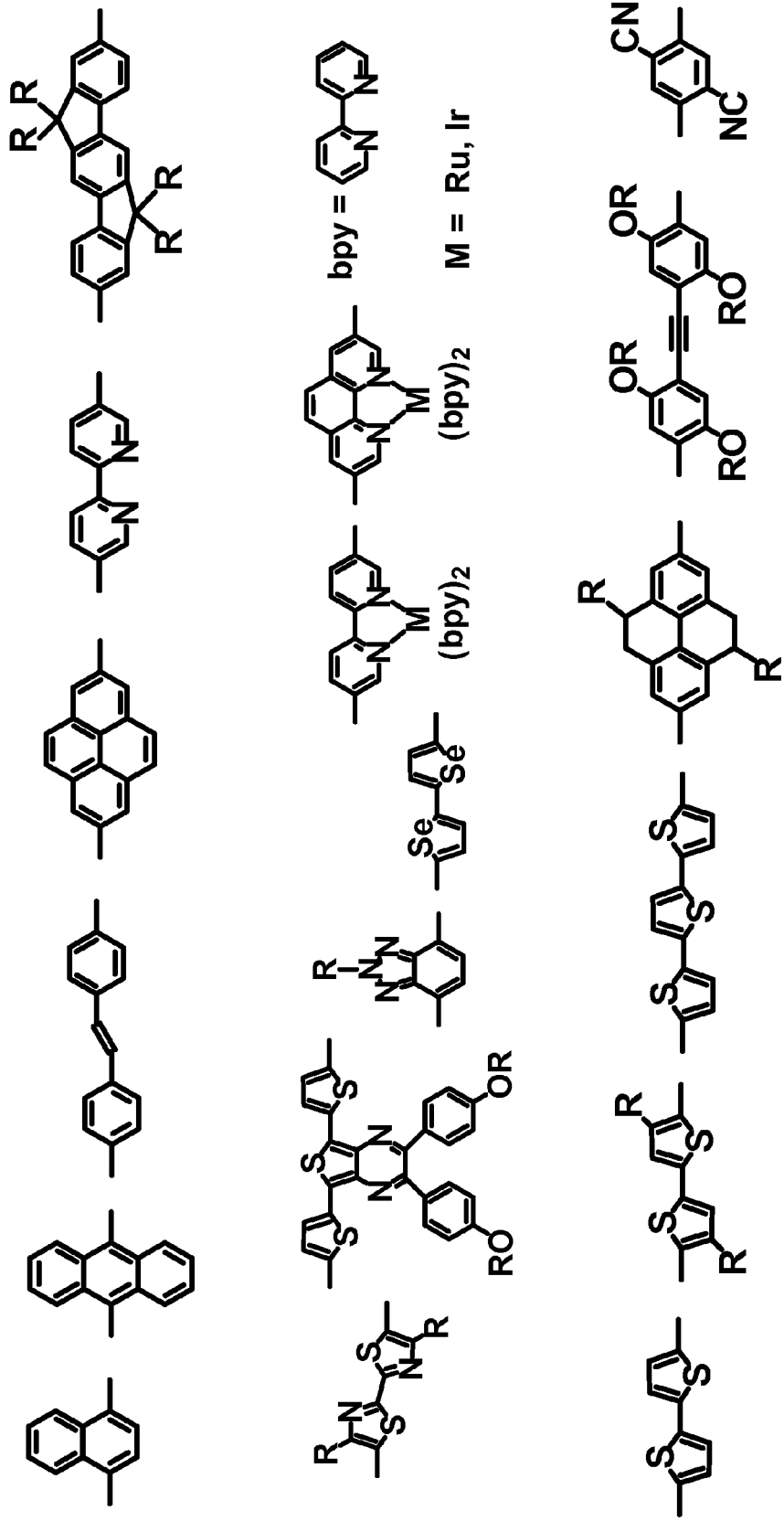
Figure 2B:
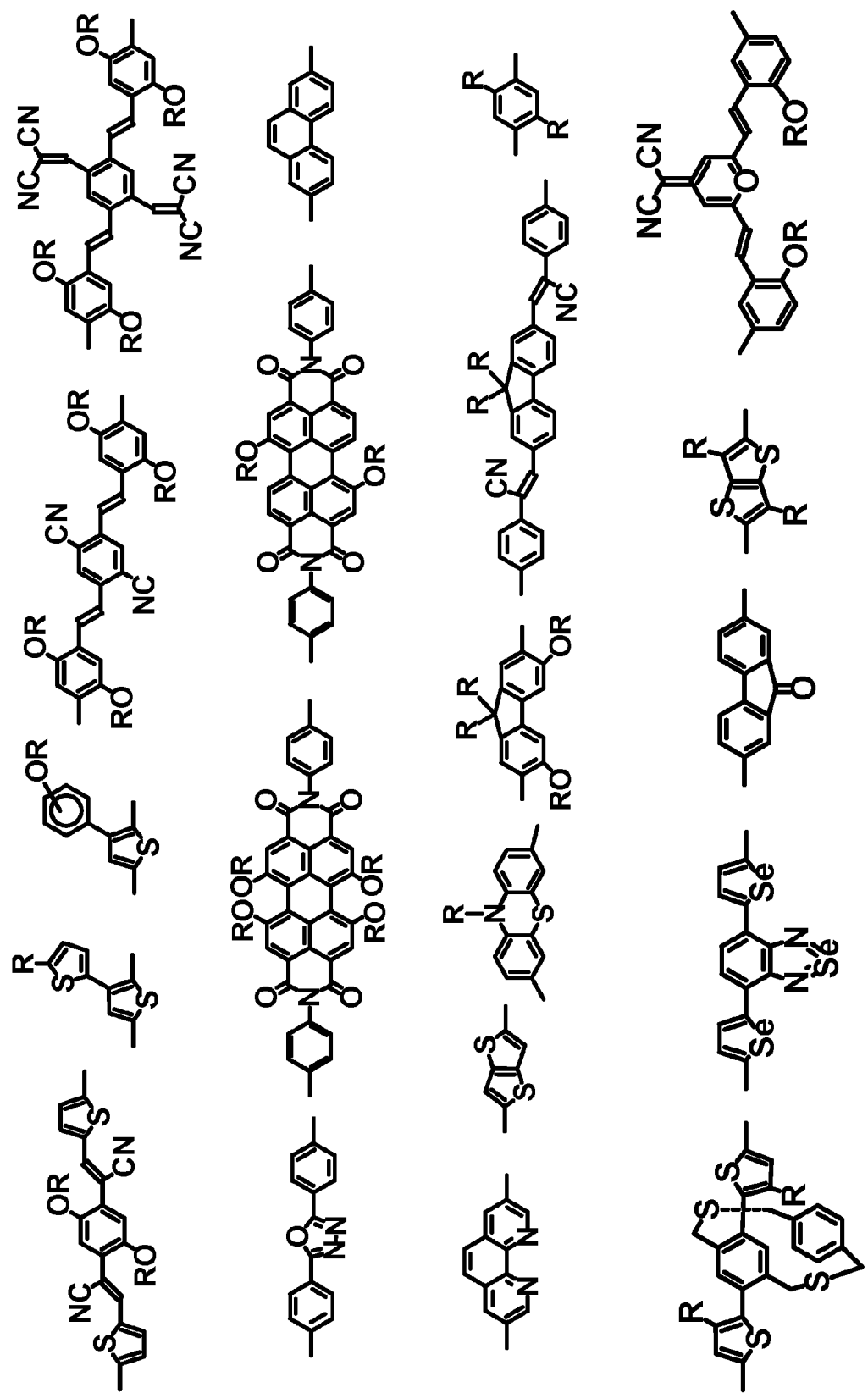

Before any embodiments of the present application are explained in detail, it is to be understood that the invention is not limited in its application to the details of construction and the arrangement of components set forth in the following description or illustrated in the following drawings. The invention is capable of other embodiments and of being practiced or of being carried out in various ways.

The present application provides fluorescent conjugated polymers with a BODIPY-based backbone. In one embodiment, the present invention provides different BODIPY monomers incorporated into a polyfluorene backbone through the 2,6-positions of BODIPY cores. Suitably, these polymers have emission into the orange region. The absorption and fluorescent maxima of certain of the copolymers are significantly red-shifted up to 48 nm and 74 nm relative to those of the starting BODIPY dyes due to the extended π-conjugation of the conjugated polymers in methylene chloride solution. In addition, in certain embodiments, these polymers are highly fluorescent with quantum yields ranging from about 55.6% to about 84.8% in methylene chloride solution.

In one embodiment, the invention provides a polymer according to formula (I):

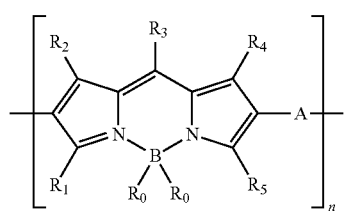

(I)

wherein each -A- is independently selected from -AR—, ═AR═, ═AR ═, or ═AR═;

wherein each -AR— is independently selected from arylene or heteroarylene;

wherein each $R_3$ is independently selected from R, alkyl, aryl or heteroaryl wherein each $R_2$ and $R_4$ are independently selected from alkyl or H;

wherein each $R_1$ and $R_5$ are independently selected from hydrogen, alkyl, or ═AR;

wherein each $R_0$ is —F, —OR, —R, aryl, heteroaryl, ═R, ═Aryl, or ═Heteroaryl;

wherein each R is independently selected from —H, —$(CH_2)_m R_{10}$, —$(CH_2)_m COO(CH_2)_p CH_3$, —$(CH_2)_m SO_3Na$, —$(CH_2)_m PO_3Na$, —$(CH_2)_m N(CH_3)_3^+ Br^-$, —$(CH_2)_m COH(CH_2)_p CH_3$, —$(CH_2)_m OR_{10}$, —$(CH_2)_m OR_8$, —$CH_2CH_2(OCH_2CH_2)_m OR_{10}$, —$CH_2CH_2(OCH_2CH_2)_m OR_8$, —$CH_2CH_2(OCH_2CH_2)_m SR_8$, or

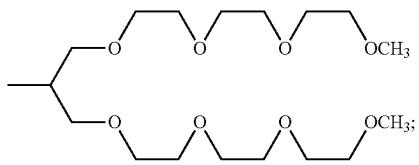 [SMILES: COCCOCCOCCOCC(C)COCCOCCOCCOC]

and
wherein each $R_8$ is independently selected from a carbohydrate residue;
and wherein each $R_{10}$ is independently selected from hydrogen, alkyl, heteroalkyl, hydroxy, amino, ammonic acid, thiol, carboxylic acid, nitrile, azide, ethynylene, halo, and tosylate;
wherein m is from 0 to 100;
wherein n is from 2 to 300 and
wherein p is from 0 to 20.

In another embodiment, the invention provides a polymer according to formula (II):

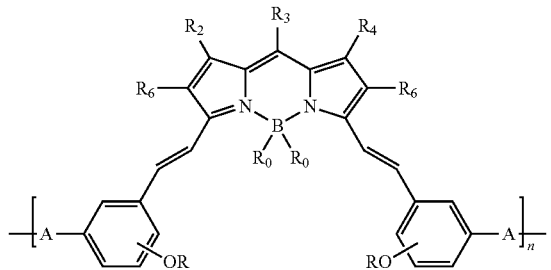

(II)

wherein each -A- is independently selected from -AR—, ═AR═, ═AR ═, or ═AR═;

wherein each -AR— is independently selected from arylene or heteroarylene;

wherein each $R_3$ is independently selected from R, alkyl, aryl or heteroaryl wherein each $R_2$ and $R_4$ are independently selected from alkyl or H;

wherein each $R_6$ is independently selected from H or alkyl;

wherein each $R_0$ is —F, —OR, —R, aryl, heteroaryl, ═R, ═Aryl, or ═Heteroaryl;

wherein each R is independently selected from —H, —(CH$_2$)$_m$R$_{10}$, —(CH$_2$)$_m$COO(CH$_2$)$_p$CH$_3$, —(CH$_2$)$_m$SO$_3$Na, —(CH$_2$)$_m$PO$_3$Na, —(CH$_2$)$_m$N(CH$_3$)$_3$$^+$Br$^-$, —(CH$_2$)$_m$COH(CH$_2$)$_p$CH$_3$, —(CH$_2$)$_m$OR$_{10}$, —(CH$_2$)$_m$OR$_8$, —CH$_2$CH$_2$(OCH$_2$CH$_2$)$_m$OR$_{10}$, —CH$_2$CH$_2$(OCH$_2$CH$_2$)$_m$OR$_8$, —CH$_2$CH$_2$(OCH$_2$CH$_2$)$_m$SR$_8$, or

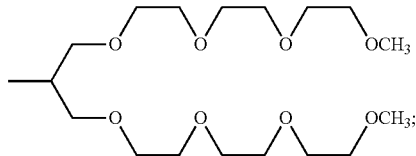 [SMILES: COCCOCCOCCOCC(C)COCCOCCOCCOC]

and
wherein each R$_8$ is independently selected from a carbohydrate residue;
and wherein each R$_{10}$ is independently selected from hydrogen, alkyl, heteroalkyl, hydroxy, amino, ammonic acid, thiol, carboxylic acid, nitrile, azide, ethynylene, halo, and tosylate;
wherein m is from 0 to 100;
wherein n is from 2 to 300 and
wherein p is from 0 to 20.

In yet another embodiment, the invention provides a polymer according to formula (III):

(III)

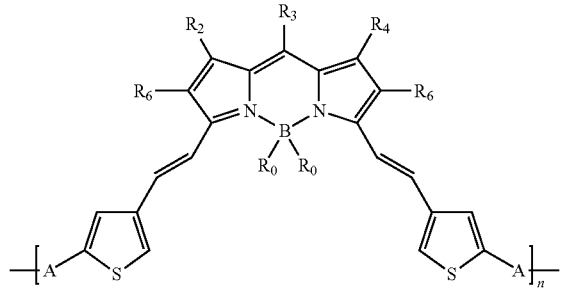

wherein each -A- is independently selected from -AR—, ══════AR══════, ══════AR══════, or ══════AR══════;

wherein each -AR— is independently selected from arylene or heteroarylene;
wherein each R$_3$ is independently selected from R, alkyl, aryl or heteroaryl
wherein each R$_2$ and R$_4$ are independently selected from alkyl or H;
wherein each R$_6$ is independently selected from H or alkyl;
wherein each R$_0$ is —F, —OR, —R, aryl, heteroaryl, ══════R, ══════-Aryl, or ══════-Heteroaryl;
wherein each R is independently selected from —H, —(CH$_2$)$_m$R$_{10}$, —(CH$_2$)$_m$COO(CH$_2$)$_p$CH$_3$, —(CH$_2$)$_m$SO$_3$Na, —(CH$_2$)$_m$PO$_3$Na, —(CH$_2$)$_m$N(CH$_3$)$_3$$^+$Br$^-$, —(CH$_2$)$_m$COH(CH$_2$)$_p$CH$_3$, —(CH$_2$)$_m$OR$_{10}$, —(CH$_2$)$_m$OR$_8$, —CH$_2$CH$_2$(OCH$_2$CH$_2$)$_m$OR$_{10}$, —CH$_2$CH$_2$(OCH$_2$CH$_2$)$_m$OR$_8$, —CH$_2$CH$_2$(OCH$_2$CH$_2$)$_m$SR$_8$, or

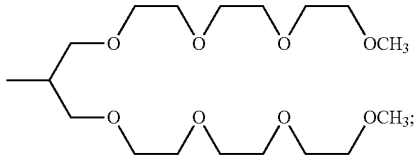 [SMILES: COCCOCCOCCOCC(C)COCCOCCOCCOC]

and
wherein each R$_8$ is independently selected from a carbohydrate residue;
and wherein each R$_{10}$ is independently selected from hydrogen, alkyl, heteroalkyl, hydroxy, amino, ammonic acid, thiol, carboxylic acid, nitrile, azide, ethynylene, halo, and tosylate;
wherein m is from 0 to 100;
wherein n is from 2 to 300 and
wherein p is from 0 to 20.

In a further embodiment, the invention provides a polymer according to formula (IV):

(IV)

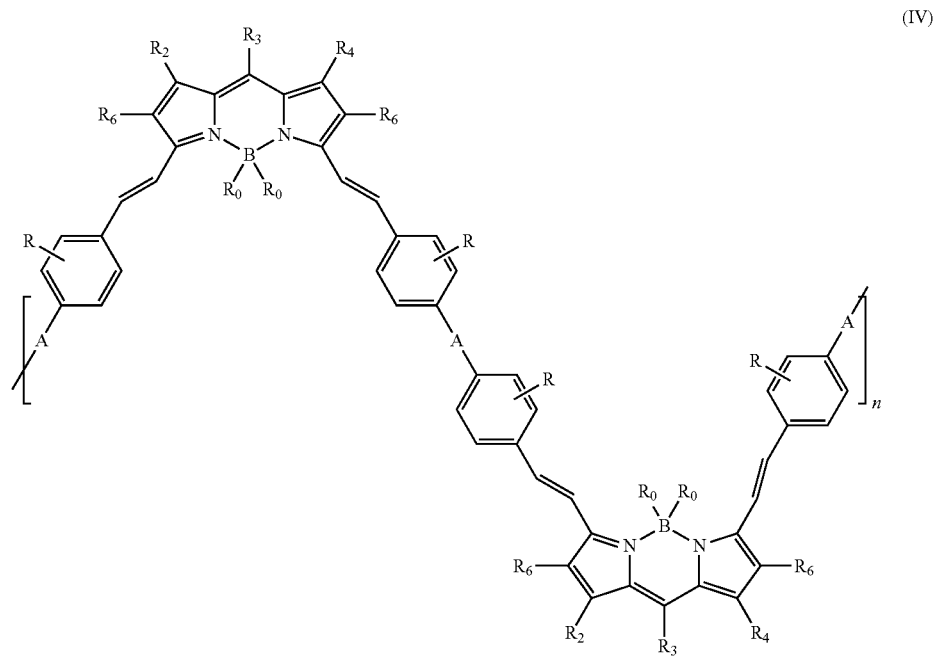

wherein each -A- is independently selected from -AR—,

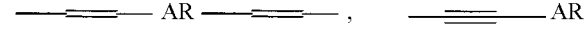 

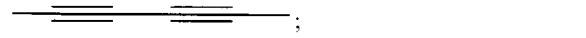;

wherein each -AR— is independently selected from arylene or heteroarylene;

wherein each $R_3$ is independently selected from R, alkyl, aryl or heteroaryl wherein each $R_2$ and $R_4$ are independently selected from alkyl or H;

wherein each $R_6$ is independently selected from H or alkyl;

wherein each $R_0$ is —F, —OR, —R, aryl, heteroaryl, 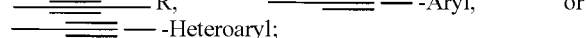

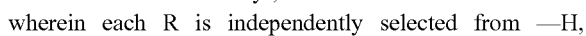;

wherein each R is independently selected from —H, —(CH$_2$)$_m$R$_{10}$, —(CH$_2$)$_m$COO(CH$_2$)$_p$CH$_3$, —(CH$_2$)$_m$SO$_3$Na, —(CH$_2$)$_m$PO$_3$Na, —(CH$_2$)$_m$N(CH$_3$)$_3$$^+$Br$^-$, —(CH$_2$)$_m$COH(CH$_2$)$_p$CH$_3$, —(CH$_2$)$_m$OR$_{10}$, —(CH$_2$)$_m$OR$_8$, —CH$_2$CH$_2$(OCH$_2$CH$_2$)$_m$OR$_{10}$, —CH$_2$CH$_2$(OCH$_2$CH$_2$)$_m$OR$_8$, —CH$_2$CH$_2$(OCH$_2$CH$_2$)$_m$SR$_8$, or

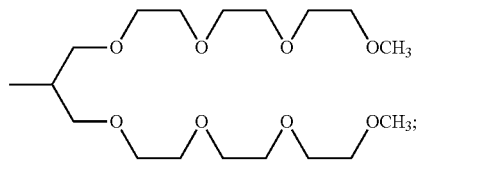 [SMILES: COCCOCCOCCOCC(C)COCCOCCOCCOC]

and wherein each $R_8$ is independently selected from a carbohydrate residue;

and wherein each $R_{10}$ is independently selected from hydrogen, alkyl, heteroalkyl, hydroxy, amino, ammonic acid, thiol, carboxylic acid, nitrile, azide, ethynylene, halo, and tosylate;

wherein m is from 0 to 100;

wherein n is from 2 to 300 and wherein p is from 0 to 20.

In certain embodiments, -AR— is selected from the following:

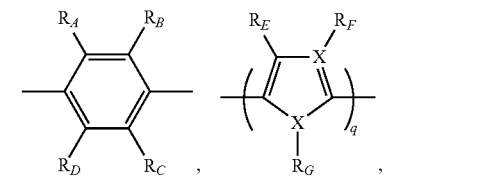

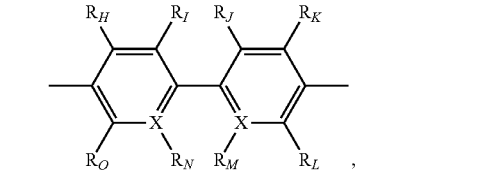

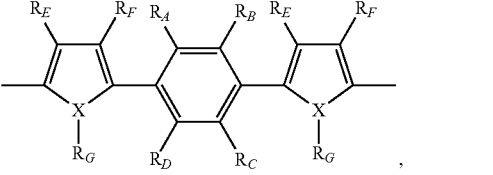

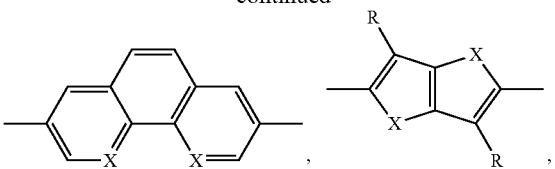

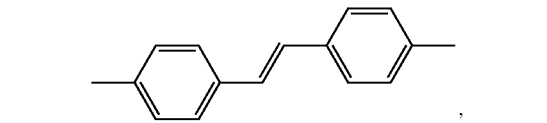

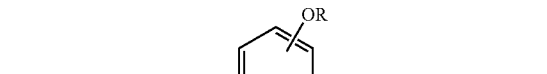

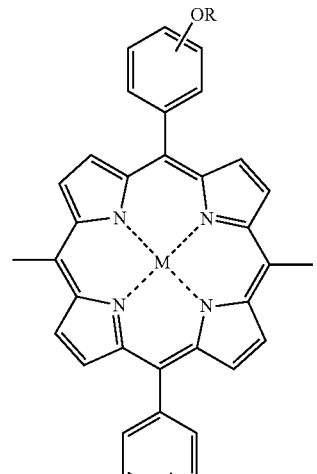

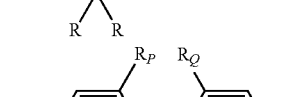

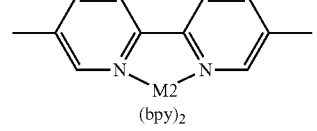

-continued

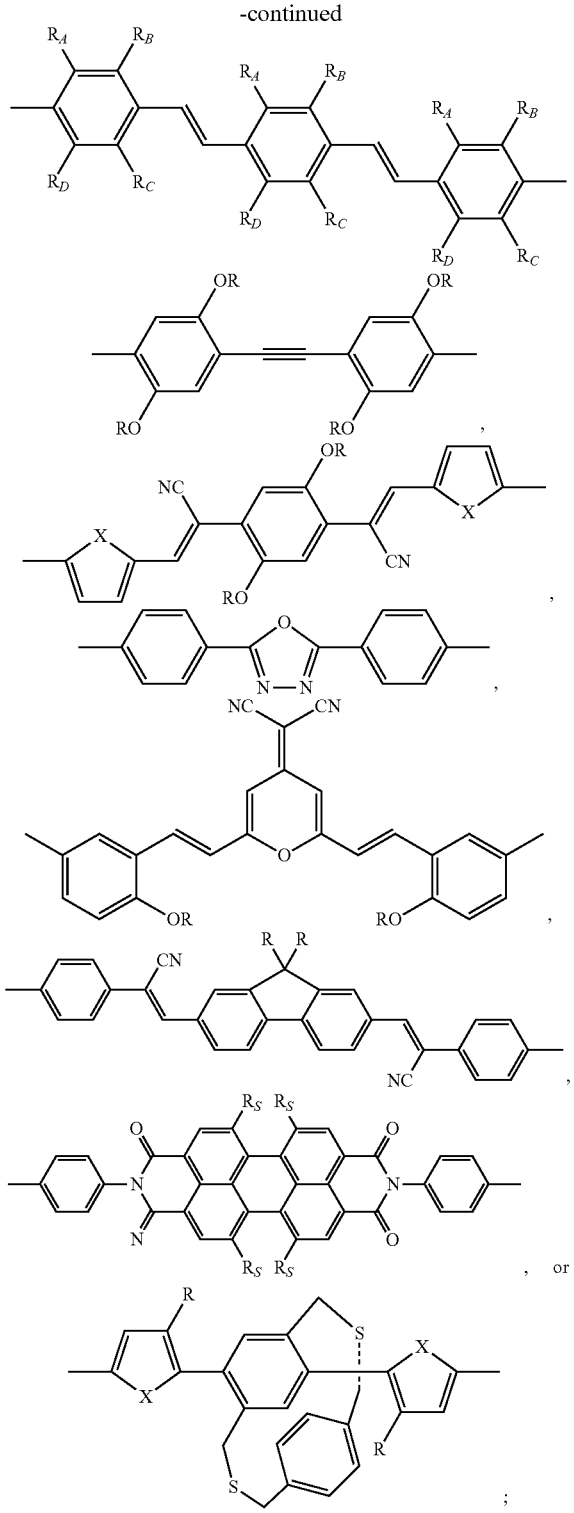

wherein each $R_A$, $R_B$, $R_C$ and $R_D$ is independently selected from R, OR, hydrogen, alkyl, heteroalkyl, hydroxy, amino, thiol, carboxylic acid, nitrile, azide, halo or $R_A$ and $R_B$ may together form an aromatic ring, or $R_C$ and $R_D$ may together form an aromatic ring or both $R_A$ and $R_B$ and $R_C$ and $R_D$ may together form an aromatic ring;

wherein each $R_E$, $R_F$ and $R_G$ is independently selected from R, OR, hydrogen, alkyl, heteroalkyl, aryl, heteroaryl, hydroxy, amino, thiol, carboxylic acid, nitrile, azide, halo, or $R_E$ and $R_F$ may together form a ring;

wherein each $R_H$, $R_I$, $R_J$, $R_K$, $R_L$, $R_M$, $R_N$, and $R_O$ is independently selected from R, OR, hydrogen, alkyl, heteroalkyl, hydroxy, amino, thiol, carboxylic acid, nitrile, azide, halo, or $R_I$ and $R_J$ may together form a ring, or $R_M$ and $R_N$ may together form a ring;

wherein each $R_P$ and $R_Q$ is independently selected from hydrogen or together form an aromatic ring;

wherein each $R_S$ is independently selected from hydrogen or OR;

wherein each X is independently a carbon atom or a heteroatom;

wherein q is an integer from 1 to 3;

wherein M is selected from Zn, Cu, Fe, and Pt;

wherein M2 is selected from Ru or Ir; and wherein bpy is

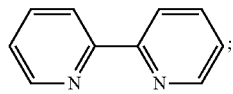

and wherein each R is independently selected from —H, —(CH$_2$)$_m$R$_{10}$, —(CH$_2$)$_m$COO(CH$_2$)$_p$CH$_3$, —(CH$_2$)$_m$SO$_3$Na, —(CH$_2$)$_m$PO$_3$Na, —(CH$_2$)$_m$N(CH$_3$)$_3^+$Br$^-$, —(CH$_2$)$_m$COH(CH$_2$)$_p$CH$_3$, —(CH$_2$)$_m$OR$_{10}$, —(CH$_2$)$_m$OR$_8$, —CH$_2$CH$_2$(OCH$_2$CH$_2$)$_m$OR$_{10}$, —CH$_2$CH$_2$(OCH$_2$CH$_2$)$_m$OR$_8$, —CH$_2$CH$_2$(OCH$_2$CH$_2$)$_m$SR$_8$, or

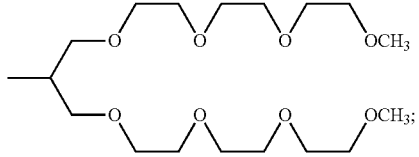 [SMILES: COCCOCCOCCOCC(C)COCCOCCOCCOC]

and wherein each $R_8$ is independently selected from a carbohydrate residue;

and wherein each $R_{10}$ is independently selected from hydrogen, alkyl, heteroalkyl, hydroxy, amino, ammonic acid, thiol, carboxylic acid, nitrile, azide, ethynylene, halo, and tosylate.

Alternatively, -AR— may be

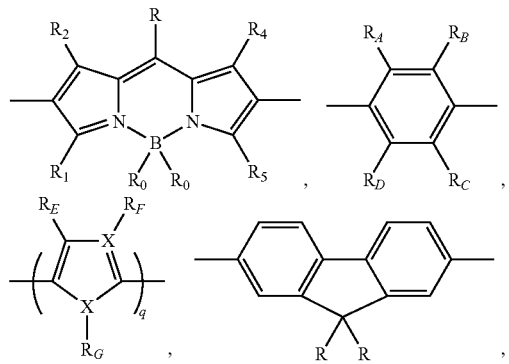

-continued

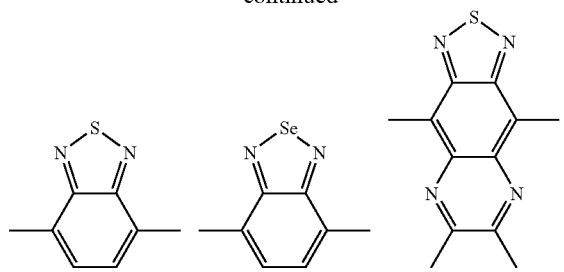

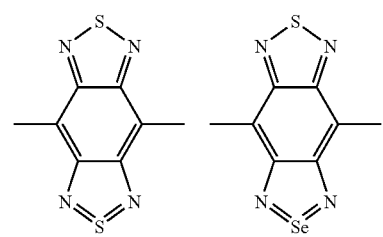

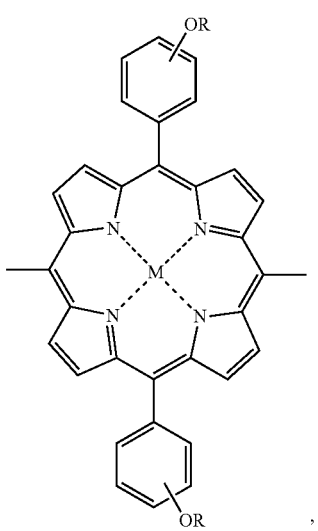

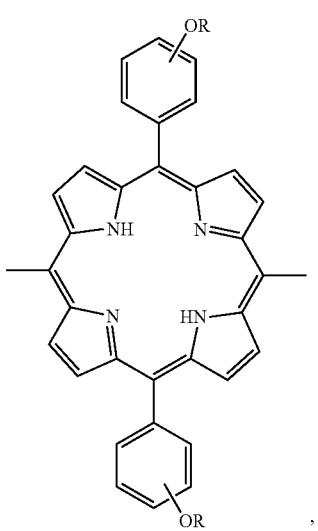

-continued

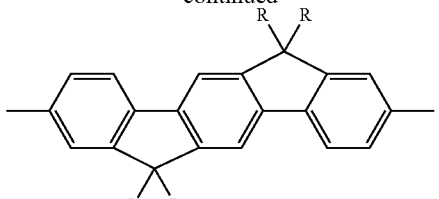

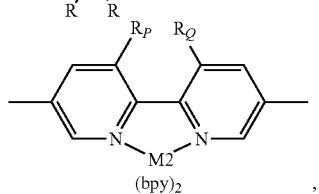

wherein each $R_A$, $R_B$, $R_C$ and $R_D$ is independently selected from R, OR, hydrogen, alkyl, heteroalkyl, hydroxy, amino, thiol, carboxylic acid, nitrile, azide, halo or $R_A$ and $R_B$ may together form an aromatic ring, or $R_C$ and $R_D$ may together form an aromatic ring or both $R_A$ and $R_B$ and $R_C$ and $R_D$ may together form an aromatic ring;

wherein each $R_E$, $R_F$ and $R_G$ is independently selected from R, OR, hydrogen, alkyl, heteroalkyl, aryl, heteroaryl, hydroxy, amino, thiol, carboxylic acid, nitrile, azide, halo, or $R_E$ and $R_F$ may together form a ring;

wherein each $R_H$, $R_I$, $R_J$, $R_K$, $R_L$, $R_M$, $R_N$, and $R_O$ is independently selected from R, OR, hydrogen, alkyl, heteroalkyl, hydroxy, amino, thiol, carboxylic acid, nitrile, azide, halo, or $R_I$ and $R_J$ may together form a ring, or $R_M$ and $R_N$ may together form a ring;

wherein each $R_P$ and $R_Q$ is independently selected from hydrogen or together form an aromatic ring;

wherein each $R_S$ is independently selected from hydrogen or OR;

wherein each X is independently a carbon atom or a heteroatom;

wherein q is an integer from 1 to 3;

wherein M is selected from Zn, Cu, Fe, or Pt;

wherein M2 is selected from Ru or Ir; and wherein bpy is

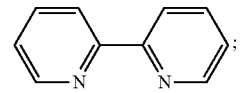

wherein each R is independently selected from —H, —(CH$_2$)$_m$R$_{10}$, —(CH$_2$)$_m$COO(CH$_2$)$_p$CH$_3$, —(CH$_2$)$_m$SO$_3$Na, —(CH$_2$)$_m$PO$_3$Na, —(CH$_2$)$_m$N(CH$_3$)$_3$$^+$Br$^-$, —(CH$_2$)$_m$COH(CH$_2$)$_p$CH$_3$, —(CH$_2$)$_m$OR$_{10}$, —(CH$_2$)$_m$OR$_8$, —CH$_2$CH$_2$(OCH$_2$CH$_2$)$_m$OR$_{10}$, —CH$_2$CH$_2$(OCH$_2$CH$_2$)$_m$OR$_8$, —CH$_2$CH$_2$(OCH$_2$CH$_2$)$_m$SR$_8$, or

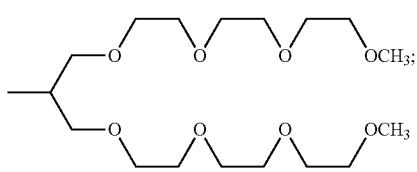 [SMILES: COCCOCCOCCOCC(C)COCCOCCOCCOC]

and wherein each R$_3$ is independently selected from a carbohydrate residue;

and wherein each $R_{10}$ is independently selected from hydrogen, alkyl, heteroalkyl, hydroxy, amino, ammonic acid, thiol, carboxylic acid, nitrile, azide, ethynylene, halo, and tosylate.

For example, -AR— may be those moieties shown in FIG. 2.

In certain embodiments, $R_3$ may be

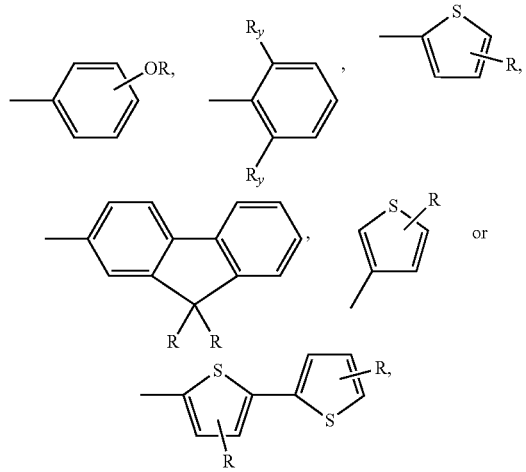

where R is as defined above.

In other embodiments, $R_3$ may be

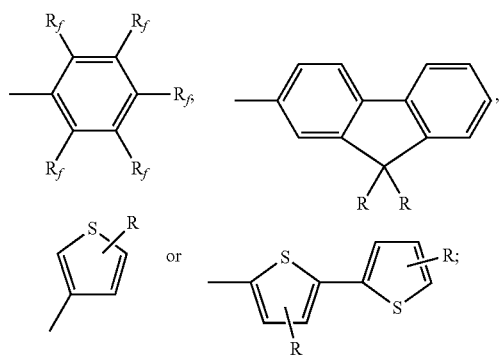

wherein each $R_F$ is independently selected from R, OR, hydrogen, alkyl, heteroalkyl, aryl, heteroaryl, hydroxy, amino, thiol, carboxylic acid, nitrile, azide or halo; and wherein each R is independently selected from —H, —$(CH_2)_m R_{10}$, —$(CH_2)_m COO(CH_2)_p CH_3$, —$(CH_2)_m SO_3Na$, —$(CH_2)_m PO_3Na$, —$(CH_2)_m N(CH_3)_3{}^+Br^-$, —$(CH_2)_m COH(CH_2)_p CH_3$, —$(CH_2)_m OR_{10}$, —$(CH_2)_m OR_8$, —$CH_2CH_2(OCH_2CH_2)_m OR_{10}$, —$CH_2CH_2(OCH_2CH_2)_m OR_8$, —$CH_2CH_2(OCH_2CH_2)_m SR_8$, or

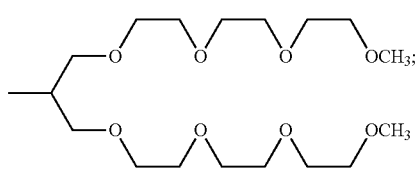 [SMILES: COCCOCCOCCOCC(C)COCCOCCOCCOC]

and
wherein each $R_8$ is independently selected from a carbohydrate residue;

and wherein each $R_{10}$ is independently selected from hydrogen, alkyl, heteroalkyl, hydroxy, amino, ammonic acid, thiol, carboxylic acid, nitrile, azide, ethynylene, halo, and tosylate.

In certain embodiments, $R_1$ or $R_5$ may be

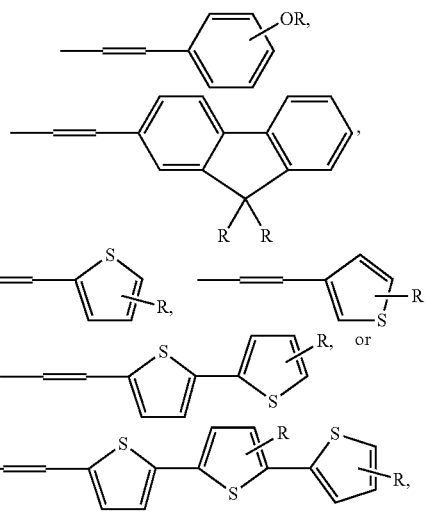

where R is as defined above.

In some embodiments, $R_0$ may be

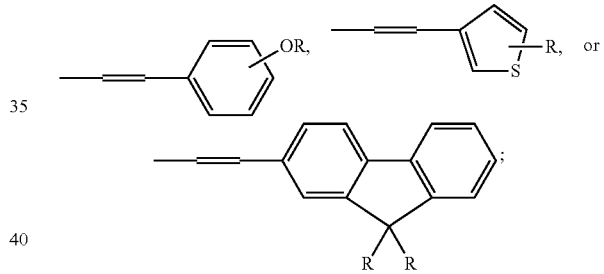

wherein each R is as defined above.

In some embodiments, m is from 0 to 50 or from 0 to 30 or from 0 to 20. In some embodiments, n is from 2 to 200 or 2 to 150. In some embodiments, p is from 1 to 10 or 3 to 15.

As used herein, "alkyl" refers to a saturated or unsaturated hydrocarbon chain having 1 to 12 carbon atoms (e.g. methyl, ethyl, propyl, butyl). Alkyl groups may be straight or branched. In some embodiments, branched alkyl groups have one or two branches. Unsaturated alkyl groups have one or more double bonds and/or one or more triple bonds. Suitably, unsaturated alkyl groups have one or two double bonds or one triple bond. Alkyl chains may be unsubstituted or substituted with from 1 to about 4 substituents unless otherwise specified. Suitably, alkyl groups are mono-, di-, or tri-substituted. Suitable alkyl substituents include, but are not limited to, cyano, oxo, halo, hydroxy, aryl (e.g., phenyl, tolyl, alkyloxphenyl, alkyloxycarbonylphenyl, halophenyl), heterocyclyl, and heteroaryl. "Lower alkyl" refers to alkyl chains having from 1 to 4 carbon atoms.

"Aryl" refers to an aromatic carbocyclic group. "Aryl" may be exemplified by phenyl. The aryl group may be substituted or unsubstituted. More than one substituent may be present. Substituents may also be themselves substituted. When substituted, the substituent group is preferably but not limited to heteroaryl; acyl, carboxyl, carbonylamino, nitro, amino, cyano, halogen, or hydroxyl. "Arylene" refers to a divalent aryl group.

"Aromatic ring" refers to a mono, bicyclic, or polycyclic ring structure which is conjugated and has a much greater stability due to electron delocalization than the hypothetical localized structure. The aromatic ring optionally contains one or more heteroatoms independently selected from nitrogen, oxygen, selenium, or sulfur. Suitable aromatic rings include, for example: anthracenyl, bipyridyl, fluorenonyl, furanyl, naphthyl, phenanthryl, phenyl, pyrazinyl, pyrenyl, pyridinyl, pyrrolyl, selenopheyl, thiazolyl, thienyl. Aromatic rings may be unsubstituted or substituted with from 1 to about 4 substituents. Suitable aromatic ring substitutents may include, for example: aryl, alkyl, alkenyl, alkynyl, halo, heteroalkyl, heterocyclyl, and heteroaryl.

"Halo" refers to fluoro, chloro, bromo or iodo.

"Heteroalkyl" refers to a saturated or unsaturated chain containing carbon and at least one heteroatom, wherein no two heteroatoms are adjacent. Heteroalkyl groups contain from 1 to 12 member atoms (carbon and heteroatoms) in the chain. Heteroalkyl groups may be straight or branched. Suitably, the branched heteroalkyl may have one or two branches. Unsaturated heteroalkyl have one or more double bonds and/ or one or more triple bonds. Heteroalkyl groups may be unsubstituted or substituted with from 1 to about 4 substituents unless otherwise specified. Suitable heteroalkyl substituents include halo, aryl (e.g., phenyl, tolyl, alkyloxyphenyl, alkyloxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e.g., amino, mono- and di-C1-C3 alkanylamino, methylphenylamino, methylbenzylamino, C1-C3 alkanylamido, carbamamido, ureido, guanidino). "Lower heteroalkyl" refers to heteroalkyl chains having 1 to 4 member atoms.

"Heteroaryl" refers to a monocyclic or bicyclic aromatic carbocyclic radical having one or more heteroatoms in the carbocyclic ring. Heteroaryl may be substituted or unsubstituted. More than one substituent may be present. When substituted, the substituents may themselves be substituted. Preferred but non limiting substituents are aryl, $C_1$-$C_4$ alkylaryl, amino, halogen, hydroxy, cyano, nitro, carboxyl, carbonylamino, or $C_1$-$C_4$ alkyl. Preferred heteroaromatic groups include tetrazoyl, triazolyl, thienyl, thiazolyl, purinyl, pyrimidyl, pyridyl, and furanyl. More preferred heteroaromatic groups include benzothiofuranyl; thienyl, furanyl, tetrazoyl, triazolyl, and pyridyl. "Heteroarylene" refers to a divalent heteroaryl group.

"Heteroatom" refers to a nitrogen, sulfur, selenium or oxygen atom. Groups containing more than one heteroatom may contain different heteroatoms. As used herein, halogens are not heteroatoms.

"Member atom" refers to a polyvalent atom (e.g., C, O, N, or S atom) in a chain or ring system that continues the chain or ring system. For example, in benzene the six carbon atoms are member atoms and the six hydrogen atoms are not member atoms.

"Ring" refers to a cycloalkyl, heterocycloalkyl, or an aromatic ring. The ring has from 5 to 7 members. A ring may be unsubstituted or substituted with from 1 to about 4 substituents. Suitable ring substitutents may include, for example: aryl, alkyl, alkenyl, alkynyl, halo, heteroalkyl, heterocyclyl, or heteroaryl.

As used herein,

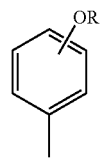

refers to any of the following:

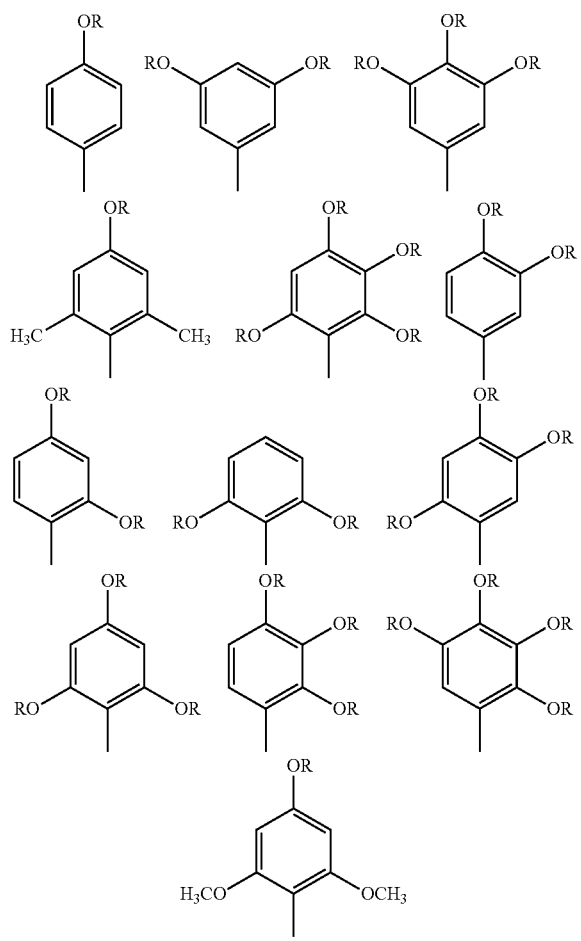

As used herein,

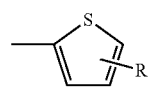

refers to any of the following:

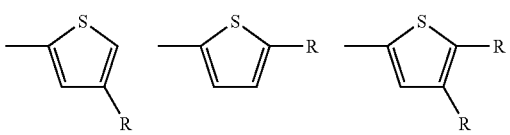

-continued

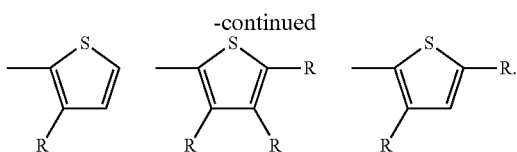

As used herein,

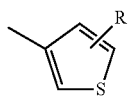

refers to any of the following:

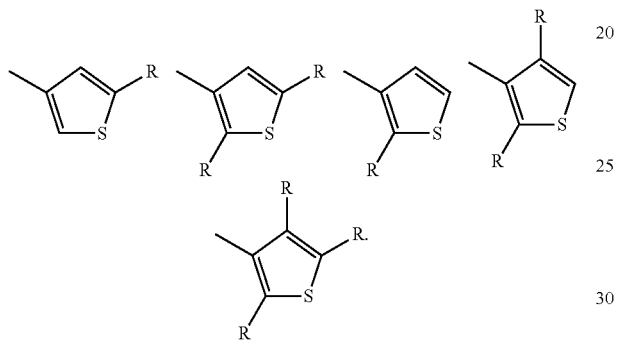

The polymers of the present invention may display significant red shifts of both UV-absorption and emission maxima compared with their BODIPY counterparts due to significantly extended π-conjugation. Commonly, polyfluorene homopolymers possess a large band gap and emit blue light. A variety of narrow-band-gap monomer units such as 2,1,3-benzoselenadiazole, 2,1,3-naphthoselenadiazole and 4,7-dithiophen-2'-yl-2,1,3-benzothiazole can be incorporated into the polyfluorene backbone to tune the polymer emission wavelengths from orange to red or even to the near-infrared region. Use of a long, flexible and highly hydrophilic oligo (ethylene glycol) linker at the meso position facilitates, inter alia, water-solubility of conjugated glycopolymers, prevention of nonspecific interactions with other proteins, and reduction of steric binding hindrance of the polymeric carbohydrates to carbohydrate-binding proteins at bacterial and viral surfaces. In one embodiment, the BODIPY-based polymers are soluble in aqueous solution or organic solvents such as chloroform, methylene chloride, acetone, dimethylformamide, dimethyl sulfoxide and tetrahydrofuran. Suitably, aromatic groups can be introduced at the meso-position to enhance solubility.

In some embodiments, the BODIPY-based polymer may be further functionalized with a moiety selected from the group consisting of an active agent, DNA, RNA, PNA aptamers, antibodies, carbohydrates, a saccharide (such as monosaccharides, disaccharides, trisaccharides, and oligosaccharides), polypeptides, peptides, cancer-homing peptides, and lipids. These additional groups may be added through any one of a variety of reactions known to one of ordinary skill in the art, such as click chemistry, amidation reactions and thioether formations. The functionalization suitably takes place at the meso position.

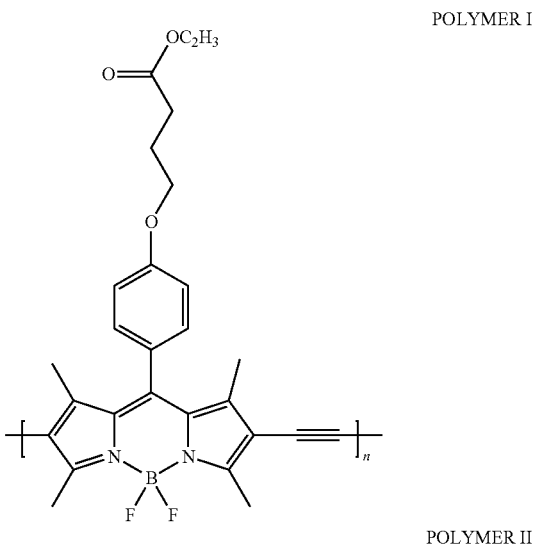

The use of poly(ethylene glycol) linkers between carbohydrates and polymer backbone makes fluorene-based conjugated glycopolymers highly soluble in aqueous solution and enables sensitive detection of a few cells of E. coli bacteria.

In one embodiment, the present invention provides fluorescent conjugated polymers with BODIPY backbone bearing ethyl phenoxybutanoate groups at the meso-position (polymers I and II).

POLYMER I

POLYMER II

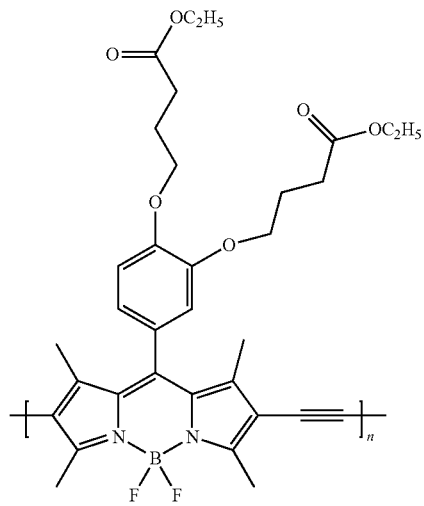

Synthesis of BODIPY-Based Polymers

The BODIPY-based polymers may be synthesized using a palladium catalyzed Suzuki polymerization of boronic acid substituted monomers and diiodo-substituted BODIPY-monomers, by employing a palladium catalyzed Sonogashira polymerization of diiodo-substituted BODIPY monomers with diethynyl-substituted BODIPY monomers or aryl monomers, by polymerizing diethynyl-substituted BODIPY monomers with CuCl, or by utilizing a palladium catalyzed Heck polymerization of diiodo-substituted BODIPY-monomers with divinyl-functionalized BODIPY monomers or aryl monomers. Various polymers and their syntheses are described in Color Tuning of Polyfluorene Emission with BODIPY Monomers. Ge Meng, Singaravelu Velayudham, Adrian Smith, Rudy Luck, and Haiying Liu, Macromolecules, 42 (2009) 1995-2001, which is incorporated by reference herein; Synthesis and Optical Properties of Red and Deep-Red Emissive Polymeric and Copolymeric BODIPY Dyes, Venkat R. Donuru, Giri K. Vegesna, Singaravelu Velayudham, Sarah Green, and Haiying Liu, Chemistry of Materials, 21(10) (2009) 2130-2138, which is incorporated by reference herein; and Deep-Red Emissive Conjugated Poly (2,6-BODIPY-Ethynylene)s Bearing Alkyl Side Chains, Venkat R. Donuru, Giri K. Vegesna, Singaravelu Velayudham, Ge Meng, Haiying Liu, Journal of Polymer Science, Part A: Polymer Chemistry, 47(20) (2009) 5354-5366, which is incorporated by reference herein.

For example, 9,9-dihexylfluorene-2,7-diboronic acid may be coupled with each one of three different 2,6-diiodo-substituted BODIPY monomers, affording polymers III, IV and V.

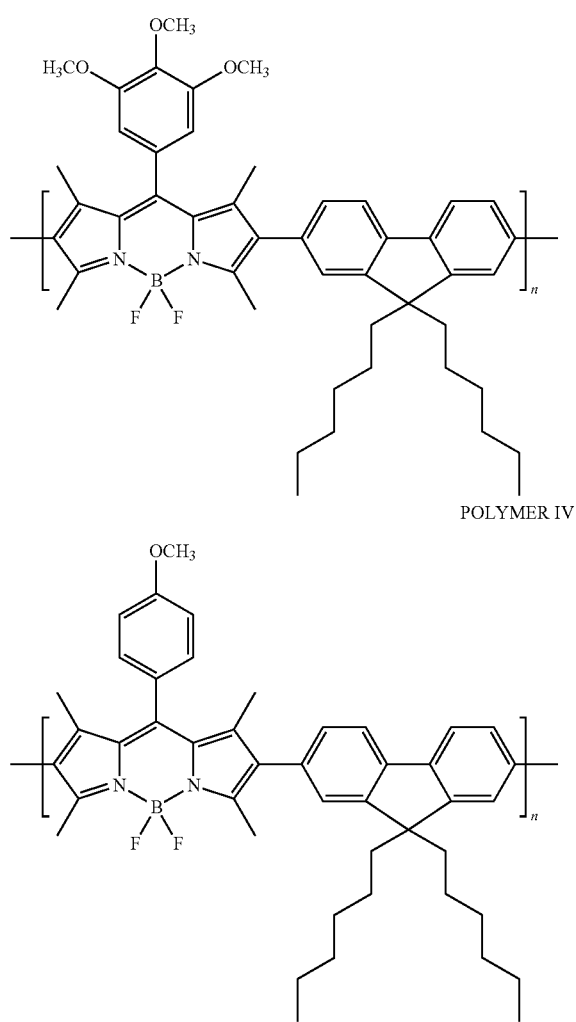

POLYMER III

POLYMER IV

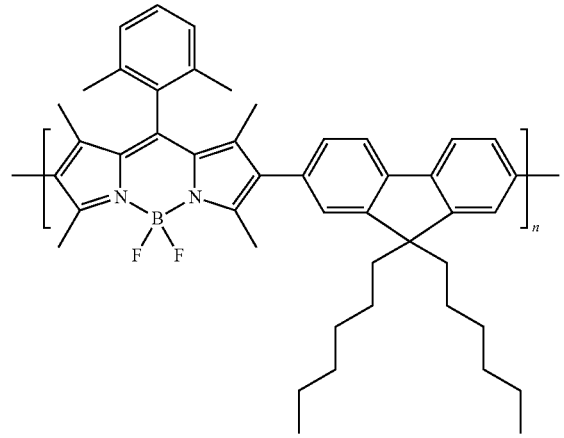

POLYMER V

Use in Medical Imaging and for Detection of Cells, Bacteria and Viruses.

Carbohydrates play important roles in key recognition events with a variety of receptor proteins such as hormones, enzymes, toxins, lectins, antibodies, viruses, and bacteria. They are also involved in numerous biological processes such as cell growth, recognition and differentiation, cancer metastasis, inflammation, bacterial and viral infection. Individual carbohydrate-protein interactions are generally weak, but should be able to be amplified by the glycoside clusters expressed on the cell surface. The overall binding capacity with protein receptors, commonly with multiple binding sites, may be enhanced over the affinity of individual monovalent ligands through cooperative multiple interactions.

Fluorescent conjugated glycopolymers, such as those according to the present invention, which combine fluorescent scaffolding and carbohydrate reporting functions into one package, provide techniques to study carbohydrate-protein interactions for bioimaging applications because of their intrinsic fluorescence and multivalent display of carbohydrates. The fluorescent conjugated glycopolymers described herein have utility as bioimaging materials with high fluorescent quantum yields for sensitive detection of cells, bacteria and influenza virus. The deep-red and near-infrared emissions of the polymers help to circumvent the problem of residual blue fluorescence (blue haze) that tends to emanate from biological fluids because the deep-red and near infrared polymeric dyes have low background absorption, low scattering and cheap illumination sources. In addition, fluorescent conjugated glycopolymers, such as those described herein, with near-infrared emissions will have a potential in vivo application in deep-tissue bioimaging detection since the near-infrared emission propagates through two or more centimeters of tissue and may enable deep tissue imaging. They may also be used for cancer imaging by attaching cancer-homing peptides to conjugated polymers.

Each of the polymers according to the present invention may be further functionalized with a moiety selected from the group consisting of an active agent, DNA, RNA, PNA aptamers, antibodies, carbohydrates, saccharides (such as monosaccharides, disaccharides, trisaccharides, and oligosaccharides), polypeptides, peptides, cancer-homing peptides, and lipids. Suitably, these moieties are attached at the meso-position through a tethered linker, e.g. an oligo(ethyelene glycol). Alternatively, the moiety may be attached to the aryl monomer.

Suitable carbohydrates include, but are not limited to, mannose, sialic acid and galactose as is shown below in Table 1.

TABLE 1

Chemical Structures of a few carbohydrates in BODIPY-based conjugated glycopolymers and their interactive bacteria or virus.

| Carbohydrate residue (R) | α-Mannose | β-Lactosamine | α2,3-Sialic acid |
|---|---|---|---|
| Bacteria | *Escherichia coli* | *Clostridium perfringens* | Avian influenza virus |

| Carbohydrate residue (R) | α2,6-Sialic acid |
|---|---|
| Bacteria or virus | Human influenza virus |

Suitably, the BODIPY-based polymers fluoresce in the near-infrared region, e.g. about 700 to about 1400 nanometers, or the deep red region, e.g. about 630 to about 699 nanometers.

In another embodiment, the BODIPY-based polymers of the present invention may be used to detect the presence of a target, such as a tumor, a cancer cell, a bacteria or viruses, in a sample. The sample may be in vitro or the sample may be in a subject. The desired target is contacted with a BODIPY-based polymer and the fluorescence of the BODIPY-based polymer is detected. In some embodiments, the fluorescence may be quantified. The desired target may be, among other things, a cell, a tumor, a cancer cell, a bacteria, or a virus. In some embodiments, the fluorescence is compared with a control. In yet another embodiment, the BODIPY-based polymer targets the area which is to be imaged. The BODIPY-based polymer may be designed to target the area by attaching an additional moiety to the polymer, e.g. a cancer-homing peptide, antibodies, carbohydrates, monosaccharides, disaccharides, trisaccharides, oligosaccharides (and others discussed herein).

In one embodiment, the BODIPY-based polymers of the present invention may be used as fluorescent agents to enhance biomedical imaging, such as imaging of DNA, proteins, peptides, tumors and cancer cells. The BODIPY-based polymer may be designed to target the area by attaching an additional moiety to the polymer, e.g. a cancer-homing peptide (such as such as RGD, NGR, GFE, F3, and LyP-1), antibodies, carbohydrates, monosaccharides, disaccharides, trisaccharides, oligosaccharides (and others discussed herein). The BODIPY-based polymer is administered to the subject and the fluorescence of the BODIPY-based polymer is detected. In some embodiments, the fluorescence may be quantified. In some embodiments, the fluorescence is compared with a control.

In yet another embodiment, the BODIPY-based polymers may be used to monitor drug delivery. Again, the BODIPY-based polymer is administered to a subject and the fluorescence of the BODIPY-based polymer is detected. In some embodiments, the fluorescence may be quantified. In some embodiments, the fluorescence is compared with a control. The BODIPY-based polymer may be further functionalized with an active agent, suitably the one which is to be monitored.

The term "contacting" is used to mean contacting in vitro, in vivo (i.e., in a subject, such as a mammal, including humans, rabbits, cats and dogs) or ex vivo. In some embodiments, the contact may occur as a result of administration of a BODIPY-based polymer to a subject. The term "administration" contemplates any route known to one of ordinary skill in the art, including, but not limited to, oral, topical, parenteral, injection, inhalation, implants, buccal and rectal.

An effective amount of a BODIPY-based polymer according to the present invention will vary with the particular target, the age and physical condition of the subject, the route of administration, the particular pharmaceutically-acceptable carrier utilized, and like factors within the knowledge and expertise of one of ordinary skill in the art.

It is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

EXAMPLES

Characterization of BODIPY-Based Monomers and Functional Conjugated Polymers.

All intermediates, carbohydrates, BODIPY dyes and conjugated polymers and glycopolymers will be fully characterized by $^1$H, $^{13}$C and $^{11}$B NMR spectroscopy, mass spectrometry, FT-IR and elemental analysis. Spectrophotometer and spectrofluometer will be used to study optical absorption, bandgap, Stoke's shift, fluorescence quantum yield and vibrational structures of fluorescent conjugated glycopolymers. The molecular weights of the glycopolymers can be manipulated by controlling polymerization time for conjugated polymers. Gel permeation chromatography ("GPC") will be used to determine molecular weight of the conjugated polymers. Matrix-assisted laser desorption/ionization time of flight mass spectrometer will also be used to determine molecular weights, repeated units, and capping end groups of conjugated polymers.

Example 1

Synthesis of Meso-Aryl-Substituted BODIPY-Based Polymers

Figure 3:
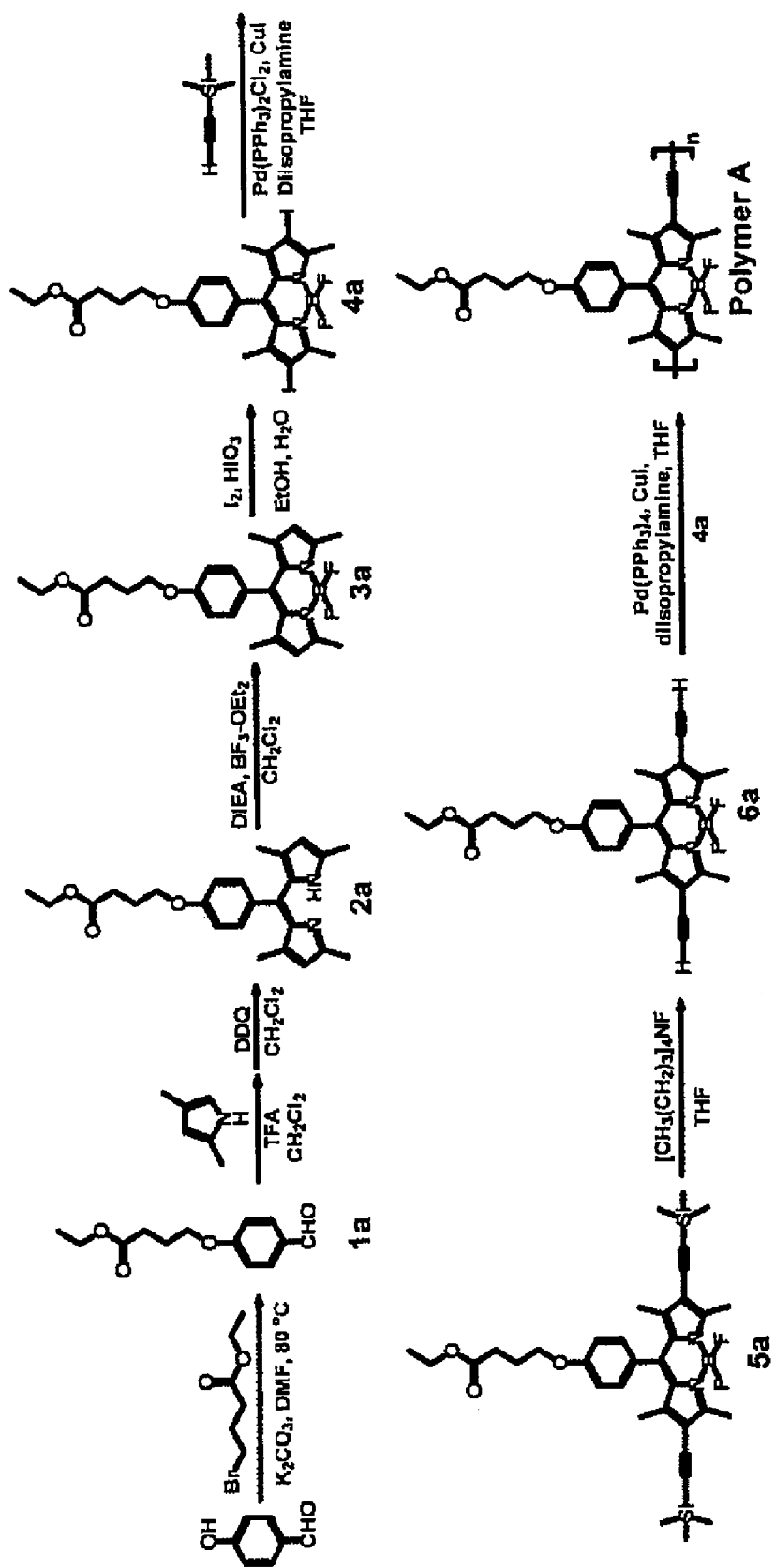
FIG. 3 shows a synthetic route to conjugated polymers with BODIPY backbone.
Figure 3:
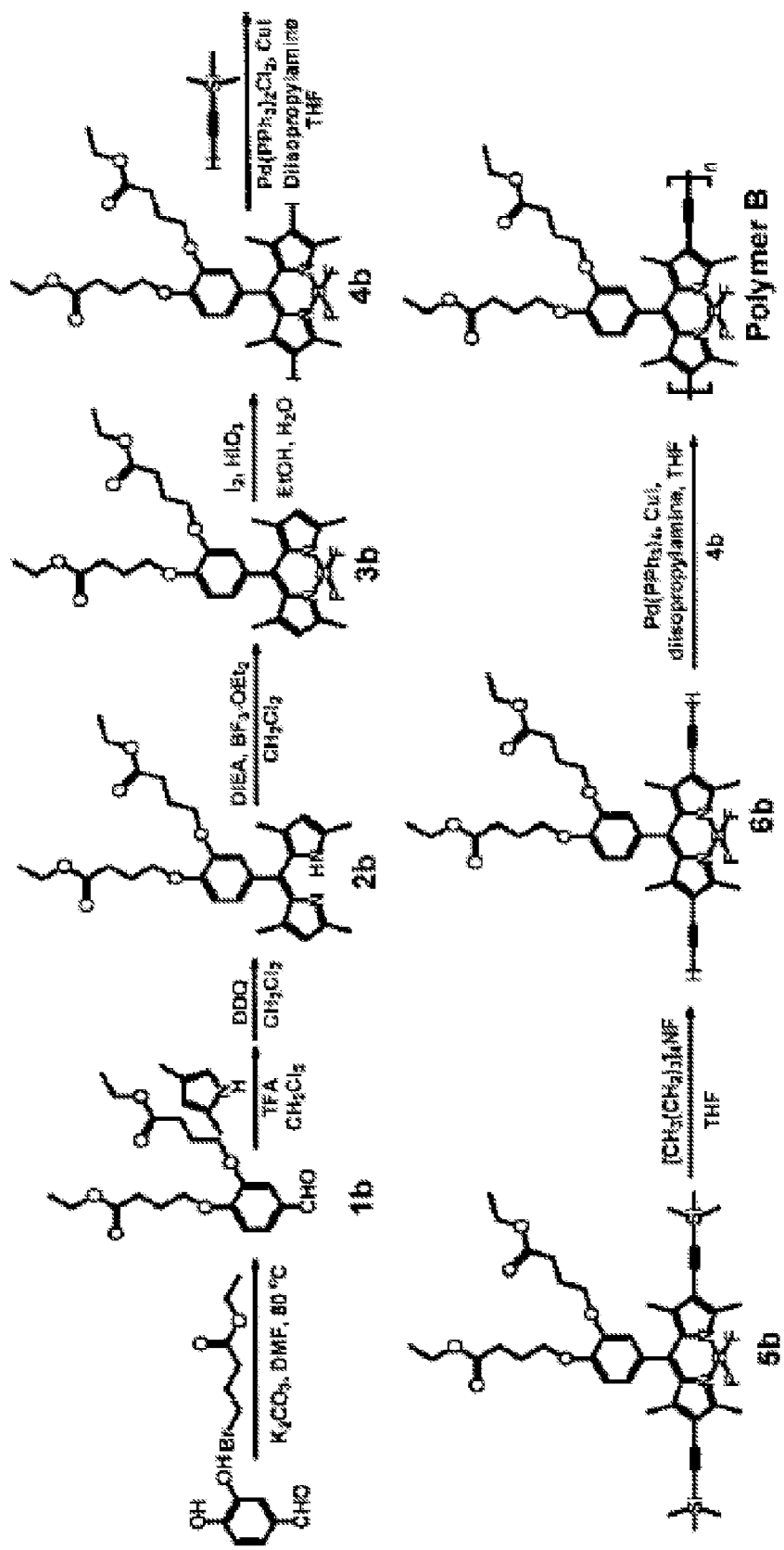
Figure 4:
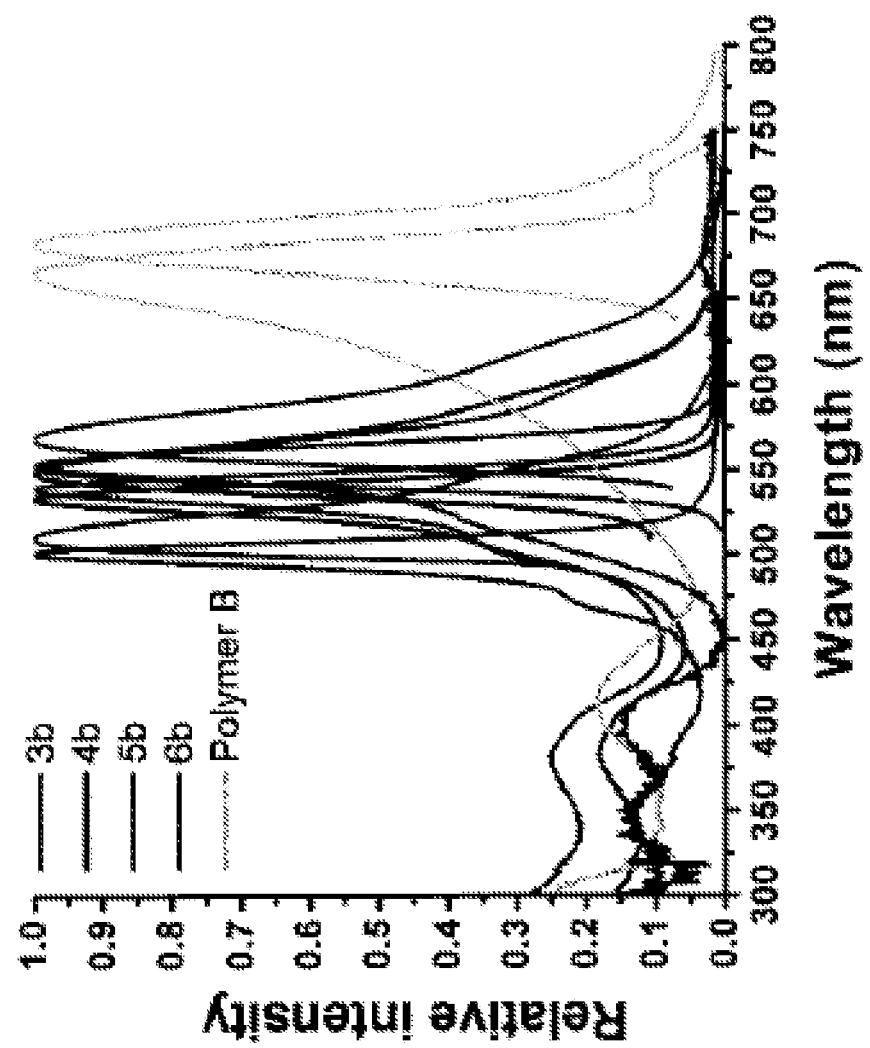
FIG. 4 shows UV-visible absorption and emission spectra of BODIPY derivatives and polymer II.

Meso-aryl-substituted BODIPY derivatives (3a and 3b) were prepared through the reaction of the formyl benzene derivatives (1a and 1b) with a large excess of 2,4-dimethylpyrrole under acid catalysis, and followed by oxidization with 2,3-dichloro-5,6-dicyano-1,4-benzoquinone (DDQ) and treatment with $BF_3$ etherate in the presence of N,N-diisopropylethylamine (DIEA) (FIG. 3). Further iodination of BODIPY derivatives (3a and 3b) afforded 2,6-diiodo-tetramethyl BODIPY derivatives (4a and 4b). 2,6-Diethynyl BODIPY derivatives (6a and 6b) were prepared by palladium-catalyzed Sonogashira reaction of compounds 4a and 4b with ethynyltrimethylsilane, affording compounds 5a and 5b, respectively, and followed by hydrolysis of compounds 5a and 5b in the presence of tetrabutylammonium fluoride.

Diethynylation of compound 4a causes peaks at 1.4 ppm corresponding to methyl group of compound 4a at 2 position to shift to lower field at 1.5 ppm and result in an additional peak at 3.3 ppm corresponding to diethynyl groups of monomer 6a. BODIPY polymers (I and II) were synthesized by palladium-catalyzed Sonogashira polymenzation of diiodo-functionalized BODIPY monomers (4a and 4b) with diethynyl-functionalized BODIPY monomers (6a and 6b) (FIG. 3). $^1$H NMR peaks of polymer I became a little broader than those of its monomer counterparts. Polymers I and II exhibit solubility similar to that of their BODIPY monomers and are soluble in common organic solvents such chloroform, methylene chloride and THF.

Arylation at the meso position has no significant effect on the absorption and emission maxima since the arylated moiety is not coplanar with the BODIPY core due to the steric hindrance although the substitution position is structurally unique. As a result, polymers I and II and their monomer counterparts have only 1 nm difference in their absorption and emission maxima as conjugated polymers do not amplify the tiny difference. However, the quantum yields of the mesophenyl compounds (3a, 4a, 5a and 6a) are a little less than the corresponding more substituted analogues (3b, 4b, 5b and 6b).

Compound 1b:
$^1$H NMR (400 MHz, $CDCl_3$) δ9.80 (s, 1H), 7.42-7.37 (m, 2H), 6.94 (d, J=8.0 Hz, 1H), 4.15-4.06 (m, 8H), 2.54-2.49 (m, 4H), 2.17-2.12 (m, 4H), 1.23 (t, J=7.2 Hz, 6H); $^{13}$C NMR (100 MHz, $CDCl_3$) δ191.0, 173.2, 154.4, 149.3, 130.3, 126.9, 112.2, 111.5, 68.1, 68.0, 60.6, 30.8, 30.6, 24.6, 24.5, 14.4.

Compound 3b:
$^1$H NMR (400 MHz, $CDCl_3$) δ6.95 (d, J=8.4 Hz, 1H), 6.78-6.76 (m, 2H), 5.95 (s, 1H), 4.17-4.05 (m, 6H), 3.98 (t, J=6.0 Hz, 2H) 2.56-2.48 (m, 10H), 2.18-2.08 (m, 4H), 1.44 (s, 6H), 1.26-1.20 (m, 6H); $^{13}$C NMR (100 MHz, $CDCl_3$) δ173.3, 173.2, 155.5, 149.7, 143.3, 141.7, 131.8, 127.7, 121.3, 121.1, 114.3, 113.9, 68.5, 68.2, 60.6, 30.8, 24.8, 14.7, 14.6, 14.4. ESI-MS calculated for M+ 584.4. found 607.3 (M+Na).

Compound 4b:
$^1$H NMR (400 MHz, $CDCl_3$) δ6.97 (d, J=8.4 Hz, 1H), 6.75-6.71 (m, 2H), 4.17-4.09 (m, 6H), 3.97 (t, J=6.0 Hz, 2H), 2.61 (s, 6H) 2.57-2.48 (m, 4H), 2.18-2.08 (m, 4H), 1.45 (s, 6H), 1.27-1.20 (m, 6H); $^{13}$C NMR (100 MHz, $CDCl_3$) δ173.3, 173.1, 156.8, 150.0, 149.9, 145.5, 141.4, 131.8, 127.2, 120.9, 114.3, 113.6, 85.7, 68.6, 68.2, 60.6, 30.8, 24.8, 17.3, 16.2, 14.4. ESI-MS calculated for M+ 836.2. found 859.4 (M+Na).

Compound 5b:
$^1$H NMR (400 MHz, $CDCl_3$) δ6.96 (d, J=8.4 Hz, 1H), 6.74-6.71 (m, 2H), 4.15-4.07 (m, 6H), 3.97 (t, J=6.0 Hz, 2H), 2.60 (s, 6H) 2.57-2.48 (m, 4H), 2.18-2.09 (m, 4H), 1.52 (5, 6H), 1.27-1.20 (m, 6H), 0.19 (5, 18H); $^{13}$C NMR (100 MHz, $CDCl_3$) δ 173.3, 173.1, 158.8, 149.9, 149.8, 145.0, 142.7, 131.4, 127.0, 120.9, 116.4, 114.3, 113.6, 101.9, 97.3, 68.6, 68.2, 60.6, 30.8, 24.8, 14.4, 13.7, 13.6, 0.28; ESI-MS calculated for M+ 776.8. found 776.9.

Compound 6b:
$^1$H NMR (400 MHz, $CDCl_3$) δ 6.97 (d, J=8.4 Hz, 1H), 6.76-6.71 (m, 2H), 4.15-4.07 (m, 6H), 3.96 (t, J=6.0 Hz, 2H), 3.30 (s, 2H), 2.60 (s, 6H) 2.57-2.48 (m, 4H), 2.18-2.09 (m, 4H), 1.54 (s, 6H), 1.27-1.20 (m, 6H); $^{13}$C NMR (100 MHz, $CDCl_3$) δ 173.3, 173.1, 158.9, 150.0, 149.9, 143.2, 131.4, 126.8, 120.9, 115.2, 114.3, 113.6, 84.6, 76.1, 68.6, 68.2, 60.6, 30.8, 24.8, 14.4, 13.7, 13.6; ESI-MS calculated for M+ 632.5. found 656.9 (M+Na).

Polymer II:
$^1$H NMR (400 MHz, $CDCl_3$) δ6.97 (d, J=8.4 Hz, 1H), 6.76-6.71 (m, 2H), 4.15-4.07 (m, 6H), 3.97 (t, J=6.0 Hz, 2H), 2.60 (5, 6H) 2.57-2.48 (m, 4H), 2.18-2.09 (m, 4H), 1.54 (s, 6H), 1.27-1.20 (m, 6H); $^{13}$C NMR (100 MHz, CDCb) 0173.3, 173.1, 158.2, 150.0, 149.8, 143.3, 142.3, 131.7, 126.9, 120.9, 116.5, 114.2, 113.6, 89.0, 76.1, 68.6, 68.2, 60.6, 30.8, 24.8, 14.4, 13.8, 13.7.

Example 2

Preparation and Characterization of BODIPY-Based Polyfluorene Derivatives

Instrumentation.
$^1$H NMR and $^{13}$C NMR spectra were taken on a 400 MHz Varian Unity Inova spectrophotometer instrument. $^1$H and $^{13}$C NMR spectra were recorded in $CDCl_3$, chemical shifts (6) are given in ppm relative to solvent peaks (1H: δ 7.26; 13C: δ 77.3) as internal standard. UV spectra were taken on a Hewlett Packard 8452A Diode Array UV-visible spectrophotometer. Fluorescence spectra were recorded on a Spex Fluorolog 1681 0.22 m steady-state fluorometer. Fluorescence quantum yields of BODIPY dyes and polymers were measured in methylene chloride and DMF, and calculated by using fluorescein excited at 490 nm in 0.1 N NaOH as the reference absolute quantum efficiency (φn=85%). Molecular weights of the polymers were determined by gel permeation chromatography ("GPC") by using a Waters Associates Model 6000A liquid chromatograph. Three American Polymer Standards Corp. Ultrastyragel columns in series with porosity indices of $10^3$, $10^4$, and $10^5$ Å were used and housed in an oven thermostated at 30° C. Mobile phase was HPLC grade THF which was filtered and degassed by vacuum filtration through a 0.5 μm fluoropore filter prior to use. The polymers were detected by a Waters Model 440 ultraviolet absorbance detector at a wavelength of 254 nm and a Waters Model 2410 refractive index detector. Molecular weights were measured relative to polystyrene standards. An Enraf Nonius CAD-4 X-Ray diffractometer was used in the crystal structure determination. The windows program WinGX was used as the interface for the solution and refinement of the model. The data were first reduced and corrected for absorption using the psi-scans, and then solved using the program SIR2004. The model was refined using SHELXL97.

Materials.

Unless otherwise indicated, all reagents and solvents were obtained from commercial suppliers (Aldrich, Sigma, Fluke, Acros Organics, Fisher Scientific, Lancaster), and were used without further purification. Air- and moisture-sensitive reactions were conducted in oven-dried glassware using standard Schlenk line or dry box techniques under an inert atmosphere of dry nitrogen.

Figure 5:
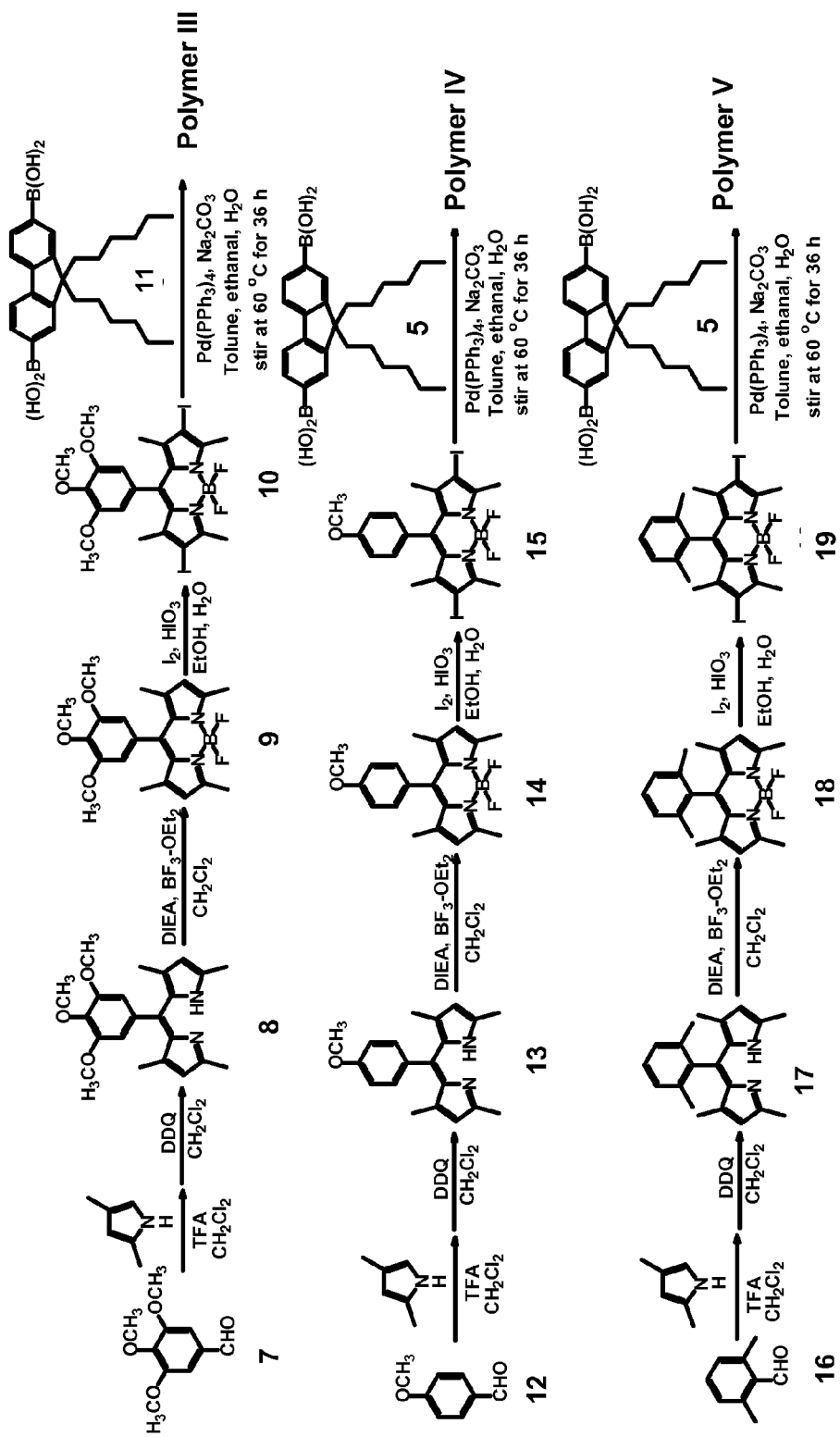
FIG. 5 shows a synthetic route to fluorescent BODIPY-based conjugated copolymers.

The synthetic scheme for polymers III, IV and V is shown in FIG. 5 and detailed below.

4,4-Difluoro-8-(3,4,5-trimethoxyphenyl)-1,3,5,7-tetramethyl-4-bora-3a,4a-diaza-s-indacene (9)

3,4,5-Trimethoxylbenzaldehyde 7 (1.65 g, 8.4 mmol) and 2,4-dimethylpyrrole (1.6 g, 16.8 mmol) were dissolved in dry $CH_2Cl_2$ (800 mL) under a nitrogen atmosphere. Nine drops of trifluoroacetic acid ("TFA") (about 0.5 mL) were added, and the mixture was stirred at room temperature overnight. After TLC monitoring showed complete disappearance of the aldehyde, a solution of 2,3-dichloro-5,6-dicyano-1,4-benzoquinone ("DDQ") (1.9 g, 8.4 mmol) in anhydrous $CH_2Cl_2$ (200 mL) was added. This mixture was further stirred for 3 hours, washed with water three times, dried over anhydrous $NaSO_4$, filtered, and concentrated to dryness. The resulting compound was roughly purified by using aluminum oxide column chromatography to give a brown powder as the crude compound 8 (about 1.0 g, 2.7 mmol, yield of the first step is 32%). This product 8 was used without further purification in the next step. The brown powder (1.0 g, 2.7 mmol) and N,N-diisopropylethylamine ("DIEA") (16 mL, 168 mmol) were dissolved in anhydrous $CH_2Cl_2$ (500 mL) under a nitrogen atmosphere. The solution was stirred at room temperature for 30 minutes and $BF_3$—$OEt_2$ (164 mL, 100 mmol) was subsequently added. This mixture was stirred for 3 hours whereupon the complexation was found to be completed by TLC monitoring. The mixture was washed thoroughly with water and brine, dried over anhydrous $Na_2SO_4$, filtered, and evaporated under vacuum. The crude compound was purified by silica gel column chromatography (eluent: petroleum ether/ethyl acetate: from first 10:1 to final 5:1, increasing the polarity of the solvent) to give a shiny green powder as the pure compound 9 (600 mg, 1.45 mmol, yield of the second step is 53%, yield overall 17%). $^1$H NMR (400 MHz, $CDCl_3$): δ 1.50 (s, 6H, 2×$CH_3$); 2.51 (s, 6H, 2×$CH_3$), 3.79 (s, 6H, 2×$OCH_3$-3,5), 3.88 (s, 3H, $OCH_3$-4), 5.97 (s, 2H, Pyr-H), 6.49 (d, 2H, Ph-CH) ppm; $^{13}$C NMR (100 MHz, $CDCl_3$): δ 14.40 (Py-$CH_3$), 14.73 (Py-$CH_3$), 56.57 ($OCH_3$), 61.50 ($OCH_3$), 105.40, 121.40, 130.28, 131.52, 138.90, 141.54, 143.24, 154.41, 155.81 ppm; IR (KBr) 3117, 3007, 2954, 2837, 1739, 1578, 1462, 1408, 1384, 1248, 1186 $cm^{-1}$. MS ($EI^+$): $C_{22}H_{25}BF_2N_2O_3$. m/z. calcd. 414.2 (M). found. 414 ($M^+$).

4,4-Difluoro-8-(3,4,5-trimethoxyphenyl)-2,6-diiodo-1,3,5,7-tetramethyl-4-bora-3a,4a-diaza-s-indacene (10)

Iodic acid (176 mg, 1 mmol) dissolved in a minimal amount of water was added drop-wise over 20 min to a solution of compound 9 (207 mg, 0.5 mmol) and iodine (158 mg, 1.25 mmol) in EtOH (40 ml). This mixture was stirred at 60° C. for 30 min. After cooling, the mixture was evaporated under vacuum. The crude product was purified by silica gel column chromatography from ethyl acetate and n-hexane to afford a golden compound as pure 10 (287 mg, 430 mmol, yield 86%). $^1$H NMR (400 MHz, $CDCl_3$): δ 1.55 (s, 6H, 2×$CH_3$), 2.64 (s, 6H, 2×$CH_3$), 3.83 (s, 6H, 2×$OCH_3$-3,5), 3.93 (s, 3H, $OCH_3$-4), 6.48 (s, 2H) ppm. $^{13}$C NMR (100 MHz, $CDCl_3$): δ 16.22, 17.09, 56.63, 61.61, 85.40, 105.15, 129.91, 131.43, 139.32, 141.17, 145.47, 154.68, 157.11 ppm. IR (KBr) 2927, 2845, 2279, 1742, 1575, 1525, 1505, 1489, 1464, 1450, 1405, 1384, 1369, 1342, 1324, 1306, 1230, 1165, 1117, 1093, 1075, 1043 $cm^{-1}$. MS ($EI^+$): $C_{22}H_{23}BF_2I_2N_2O_3$. m/z. calcd. 666.0 (M). found. 666 ($M^+$).

Polymer III:

To a mixture of compound 10 (50 mg, 0.075 mmol, 1 equiv), $Pd(PPh_3)_4$ (tetrakis(triphenylphosphine)palladium) (2.6 mg, 0.005 mmol, 0.6%), and 9,9-dihexylfluorene-2,7-diboronic acid 11 (35 mg, 0.083 mmol, 1.1 equiv) was added a degassed mixture of toluene (10 mL), EtOH (4 mL) and $H_2O$ (4 mL) containing $Na_2CO_3$ (80 mg, 10 equiv) under a nitrogen atmosphere. The mixture was vigorously stirred at 85° C. for 72 hours and then the solvent was evaporated under vacuum. The residue was dissolved in 100 mL of ethyl acetate and washed with water three times. The organic layer was collected, dried over anhydrous $Na_2SO_4$ and filtered. The filtrate was concentrated and added to ethanol to precipitate the polymer. A red powder was obtained by filtration, further washed with ethanol and then dried under vacuum for 24 hours to afford polymer III in a yield of 69%. $^1$H NMR (400 MHz, $CDCl_3$): δ 0.72 (t, 6H, 2×$CH_3$), 1.04 (m, 16H, 8×$CH_2$), 1.52 (s, 6H, 2×$CH_3$), 1.95 (br, 2H, 2×$CH_2$), 2.58 (br, 6H, 2×$CH_3$), 3.86 (br, 6H, 2×$OCH_3$), 3.88 (br, 3H, $OCH_3$), 6.63 (2H, Bodipy-Ph-H), 7.15 (4H, Ph-H), 7.72 (d, 2H, Ph-H) ppm; $^{13}$C NMR (100 MHz, $CDCl_3$): δ 12.87 (1C, Pyr-$CH_3$), 13.69, 14.13, 22.61, 24.01, 29.75, 31.66, 36.68, 40.58, 55.34, 56.66, 61.53, 105.53, 119.76, 124.91, 129.05, 131.50, 132.46, 134.53, 139.06, 140.02, 141.77, 151.16, 154.59, 154.73, 162.76 ppm; IR (KBr) 2928, 2855, 2051, 1677, 1578, 1456, 1387, 1228, 1176 $cm^{-1}$.

4,4-Difluoro-8-(4-methoxyphenyl)-1,3,5,7-tetramethyl-4-bora-3a,4a-diaza-s-indacene (14)

Compound 14 was prepared from 4-methoxybenzaldehyde 12 in 28% yield according to the method for compound 9. $^1$H NMR (400 MHz, $CDCl_3$): δ 1.43 (s, 6H, 2×$CH_3$); 2.55 (s, 6H, 2×$CH_3$), 3.87 (s, 3H, 2×$OCH_3$-4), 5.97 (s, 2H, Pyr-H), 7.01 (d, 2H, Ph-CH, J=8.4), 7.17 (d, 2H, Ph-CH, J=8.4) ppm; $^{13}$C NMR (100 MHz, $CDCl_3$): δ 14.75, 55.50, 94.62, 114.73, 121.29, 127.26, 129.41, 132.07, 142.07, 143.36, 155.47, 160.35 ppm. IR (KBr) 3038, 2967, 2932, 2841, 1609, 1573, 1538, 1505, 1463, 1441, 1407, 1368, 1303, 1289, 1246, 1184, 1155, 1109, 1075, 1050, 1022 $cm^{-1}$. MS ($EI^+$): $C_{20}H_{21}BF_2N_2O_3$. m/z. calcd. 354.2 (M). found. 354 ($M^+$).[19]

4,4-Difluoro-8-(4-methoxyphenyl)-2,6-diiodo-1,3,5,7-tetramethyl-4-bora-3a,4a-diaza-s-indacene (15)

Compound 15 was prepared from 4,4-difluoro-8-(4-methoxylphenyl)-1,3,5,7-tetramethyl-4-bora-3a,4a-diaza-s-indacene 14 in 88% yield according to the method for compound 10. $^1$H NMR (400 MHz, $CDCl_3$): δ 1.43 (s, 6H, 2×$CH_3$), 2.62 (s, 6H, 2×$CH_3$), 3.87 (s, 3H, $OCH_3$-4), 7.02 (d, 2H, Ph-H, J=8.4), 7.12 (d, 2H, Ph-H, J=8.4) ppm. $^{13}$C NMR (100 MHz, $CDCl_3$): δ 16.21, 17.38, 55.61, 85.74, 115.08, 126.89, 129.30, 131.95, 141.80, 145.58, 156.78, 160.77 ppm. IR (KBr) 2953, 2925, 2837, 2041, 1723, 1609, 1572, 1458, 1397, 1345, 1290, 1174, 1117 cm$^{-1}$. MS (EI$^+$): $C_{20}H_{19}BF_2I_2N_2O_3$. m/z. calcd. 605.9 (M). found. 606 (M$^+$).

Polymer IV:

Polymer IV was prepared from compound 15 with 9,9-dihexylfluorene-2,7-diboronic acid in 54% yield according to the method for polymer III. $^1$H NMR (400 MHz, CDCl$_3$): δ 0.67 (d, 6H, 2×CH$_3$), 0.95 (m, 16H, 8×CH$_2$), 1.67 (s, 6H, 2×CH$_3$), 1.88 (4H, 2×CH$_2$), 2.16-2.60 (m, 6H, 2×CH$_3$), 3.80 (s, 3H, OCH$_3$), 6.99 (2H, Ph-H), 7.07 (4H, Ph-H), 7.66 (3H, Bodipy-Ph-H) ppm. IR (KBr) 2927, 2856, 1724, 1610, 1529, 1458, 1388, 1292, 1176 cm$^{-1}$.

4,4-Difluoro-8-(2,6-dimethylphenyl)-1,3,5,7-tetramethyl-4-bora-3a,4a-diaza-s-indacene (18)

Compound 18 was prepared from 2,6-dimethylbenzaldehyde 16 in 67% yield according to the method for compound 9. $^1$H NMR (400 MHz, CDCl$_3$): δ 1.36 (s, 6H, 2×CH$_3$); 2.15 (s, 6H, 2×CH$_3$), 2.56 (s, 6H, 2×CH$_3$-2,6), 5.97 (s, 2H, Pyr-H), 7.13-7.27 (m, 3H, Ph-H) ppm; $^{13}$C NMR (100 MHz, CDCl$_3$): δ 13.49 (Py-CH$_3$), 14.86 (Py-CH$_3$), 19.77 (Ph-CH$_3$), 121.08 (Py-C), 128.39, 129.09, 130.55, 134.30, 135.45, 141.40, 142.40, 155.49 ppm; MS (EI$^+$): $C_{21}H_{23}BF_2N_2$. m/z. calcd. 352.2 (M). found. 352 (M$^+$).[20] IR (KBr) 2962, 2923, 2856, 1541, 1466, 1369, 1258, 1189 cm$^{-1}$. Single crystals of compound 18 (0.40×0.40×0.40 mm) were grown by vapor diffusion of hexane into a solution of the compound in ethyl acetate. A suitable crystal was cut to size, rolled in epoxy resin and mounted on a glass fiber. Crystal data for compound 18: $C_{21}H_{23}BF_2N_2$, monoclinic, space group C2/c, a=20.442 (5) Å, b=7.847 (2) Å, c=25.831 (8) Å, β=112.49 (2)°, V=3828.4 (18) Å$^3$, Z=8, D$_c$=1.223 g cm$^{-1}$, μ(Mo—Kα)=0.09 mm$^{-1}$, T=293 (2) K. Independent reflections measured=2496, R$_1$=0.059, wR$_2$=0.190 for 2496 independent observed reflections [F>4σ(F)], S=1.04.

4,4-Difluoro-8-(2,6-dimethylphenyl)-2,6-diiodo-1,3,5,7-tetramethyl-4-bora-3a,4a-diaza-s-indacene (19)

Compound 19 was prepared from 4,4-difluoro-8-(2,6-dimethylphenyl)-1,3,5,7-tetramethyl-4-bora-3a,4a-diaza-s-indacene 18 in 90% yield according to the method for compound 10. $^1$H NMR (400 MHz, CDCl$_3$): δ 1.23 (s, 6H, 2×CH$_3$), 2.12 (s, 6H, 2×CH$_3$), 2.65 (s, 6H, 2×CH$_3$-2,6), 7.15-7.32 (m, 3H, Ph-H) ppm. $^{13}$C NMR (100 MHz, CDCl$_3$): δ 15.93, 16.28, 19.83, 85.63 (Py-C—I), 128.71, 129.70, 130.44, 133.99, 135.32, 141.37, 144.68, 156.82 ppm. IR (KBr) 3063, 3018, 2957, 2916, 2856, 1736, 1596, 1459, 1343, 1241, 1173, 1085 cm$^{-1}$. MS (EI$^+$): $C_{21}H_{21}BF_2I_2N_2O_3$. m/z. calcd. 603.99 (M). found. 604 (M$^+$).

Polymer V:

Polymer V was prepared from compound 19 with 9,9-dihexylfluorene-2,7-diboronic acid in 52% yield, according to the method for polymer III. $^1$H NMR (400 MHz, CDCl$_3$): δ 0.66 (m, 6H, 2×CH$_3$), 0.98 (m, 12H, 6×CH$_2$), 1.30 (t, 6H, 2×CH$_3$), 1.58 (broad, 4H, 2×CH$_2$), 1.90 (s, broad, 4H, 2×CH$_2$), 2.19 (t, 6H, 2×CH$_3$), 2.52 (d, 6H, 2×CH$_3$), 7.09 (broad, 6H, Ph-H), 7.65 (2H, Bodipy-Ph-H) ppm; $^{13}$C NMR (100 MHz, CDCl$_3$): δ 10.06 (1C, Pyr-CH$_3$), 11.82, 13.75, 14.15, 19.94, 20.11, 22.64, 24.01, 29.76, 31.67, 40.49, 55.35, 119.67, 124.92, 128.47, 129.09, 130.52, 132.51, 134.18, 135.51, 138.21, 139.93, 151.10, 154.36, 215.64 ppm. IR (KBr) 2925, 2855, 1598, 1535, 1457, 1392, 1225, 1176, 1073 cm$^{-1}$.

Photophysical Properties.

Figure 6:
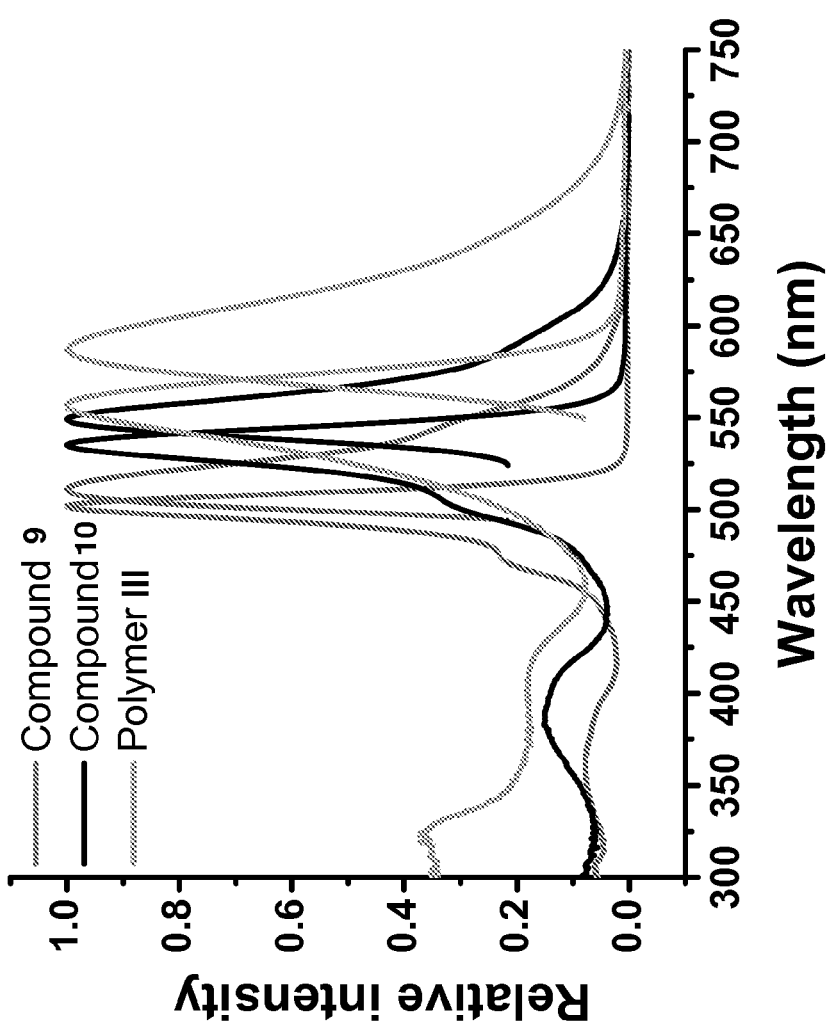
FIG. 6 shows normalized UV-Visible absorption and fluorescent spectra of compounds 9 and 10, and polymer III in methylene chloride solution.
Figure 7:
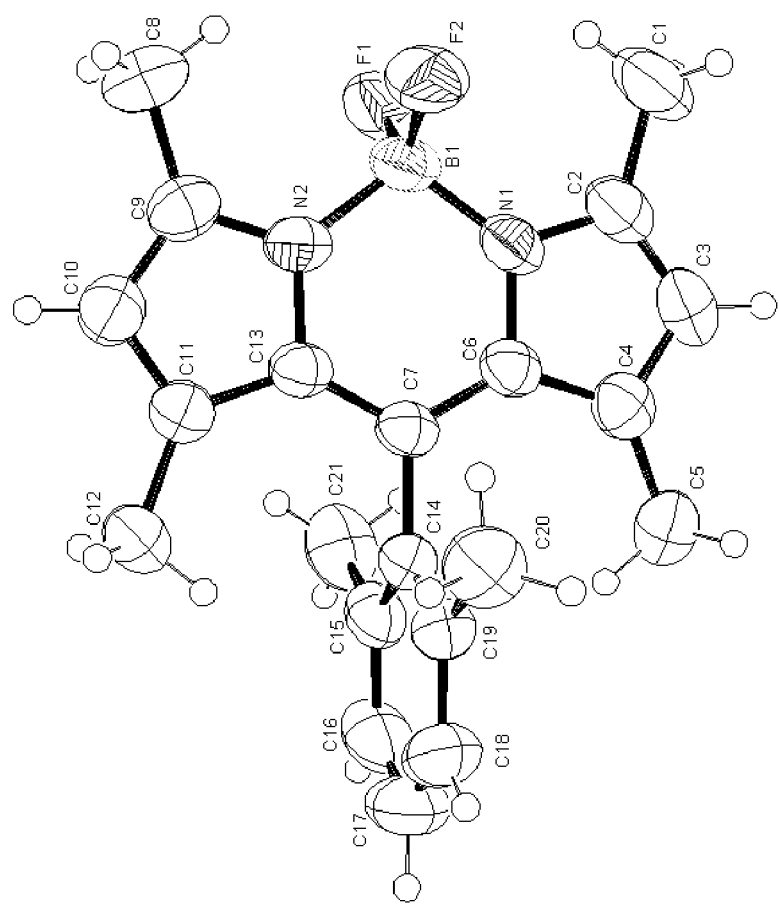
FIG. 7 shows an ORTEP representation of the molecular structure of compound 18. The non-H atoms are represented by thermal ellipsoids displayed at the 50% probability level and the H-atoms are indicated by circles of arbitrary radii.
Figure 8:
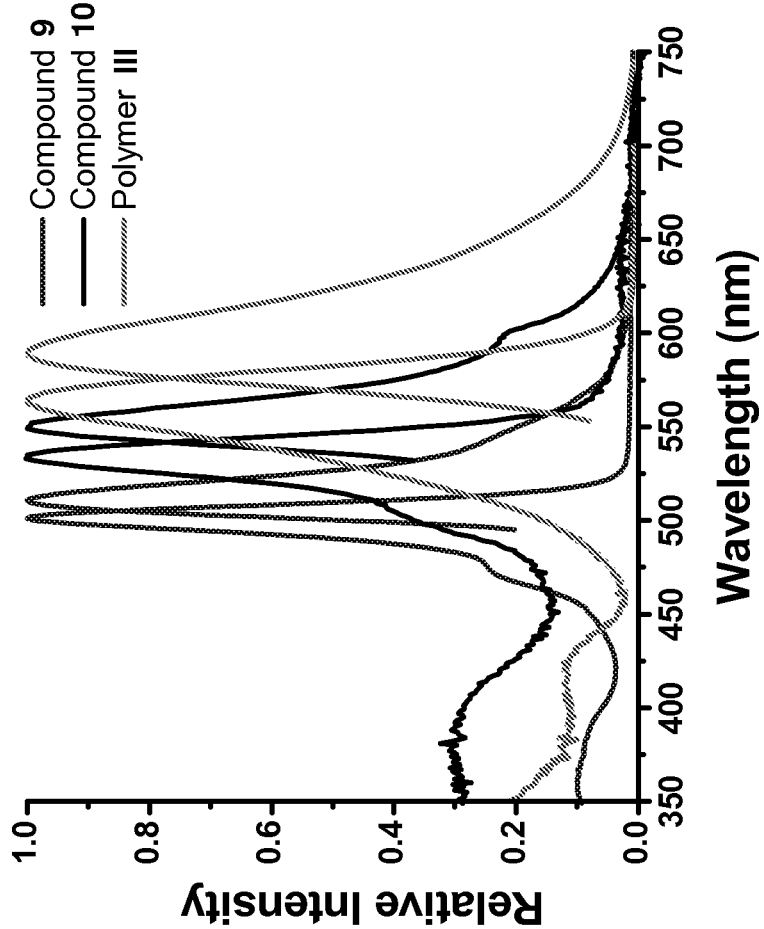
FIG. 8 shows normalized UV-Visible absorption and fluorescent spectra of compounds 9 and 10, and polymer III in DMF solution.
Figure 9:
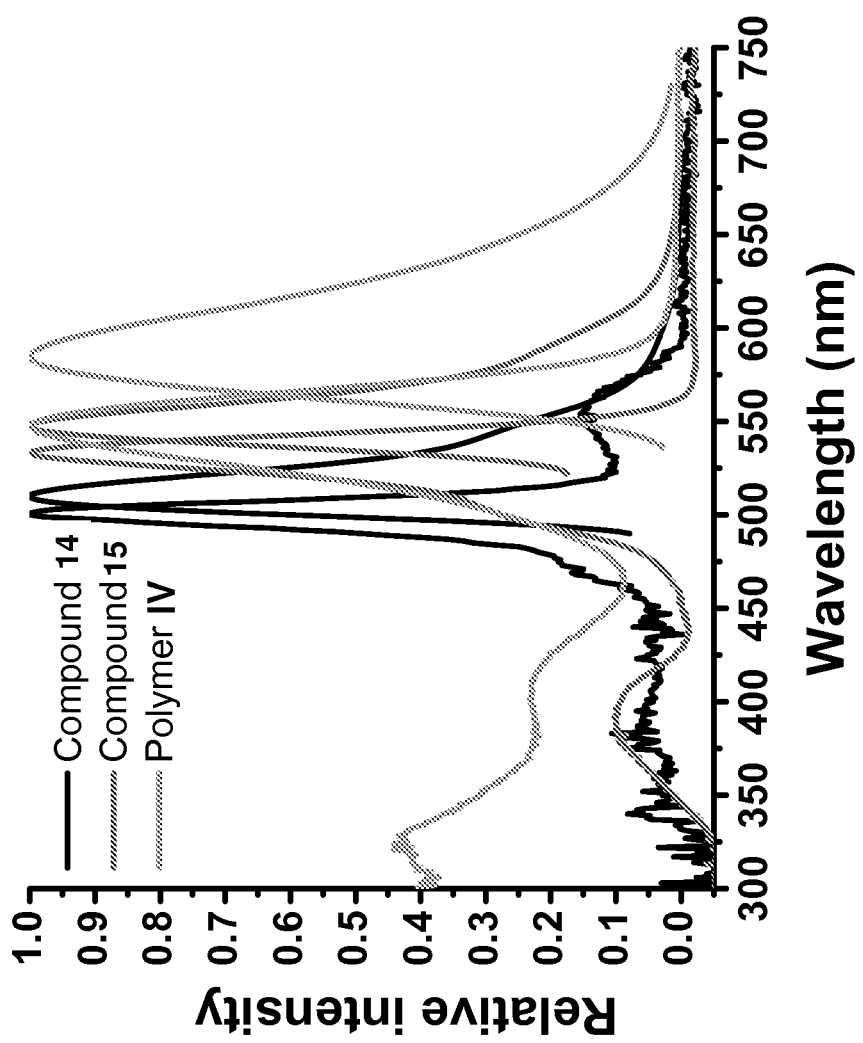
FIG. 9 shows normalized UV-Visible absorption and fluorescent spectra of compounds 14 and 15, and polymer IV in methylene chloride solution.
Figure 10:
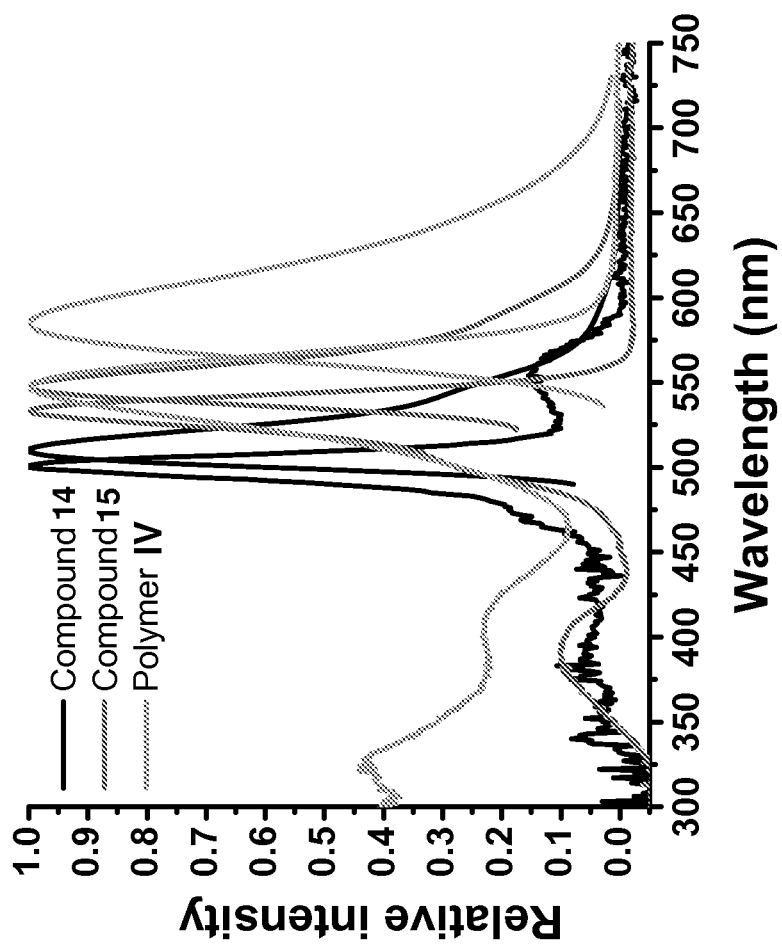
FIG. 10 shows normalized UV-Visible absorption and fluorescent spectra of compounds 14 and 15, and polymer IV in DMF solution.
Figure 11:
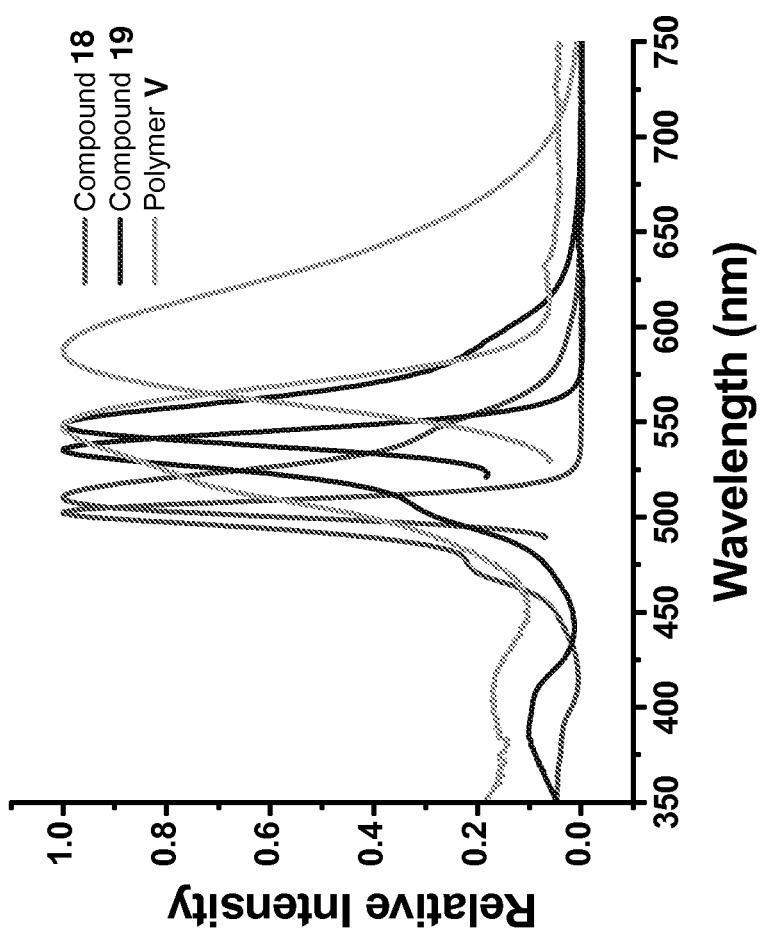
FIG. 11 shows normalized UV-Visible absorption and fluorescent spectra of compounds 18 and 19, and polymer V in methylene chloride solution.
Figure 12:
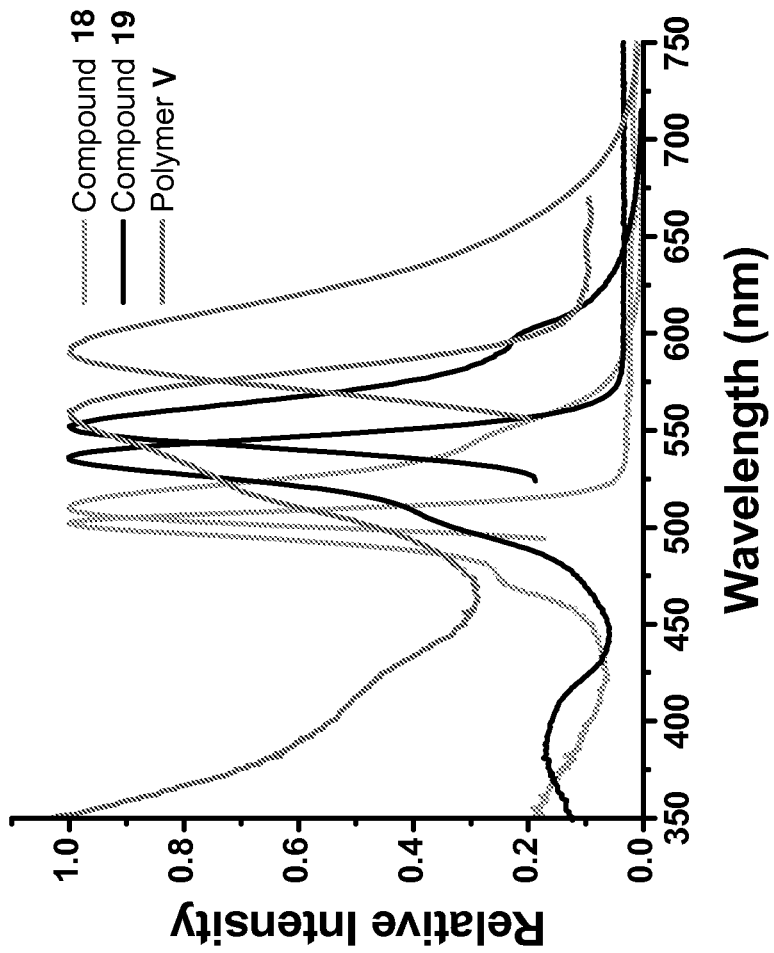
FIG. 12 shows normalized UV-Visible absorption and fluorescent spectra of compounds 18 and 19, and polymer V in DMF solution.

The photophysical characteristics of BODIPY dyes, monomers and polymers were investigated in methylene chloride and DMF solutions. The absorption properties of the BODIPY dye 9 are characterized by a strong $S_0 \rightarrow S_1$ (π–π*) transition at 502 nm and a weaker broad band at a shorter wavelength around 356 nm ascribed to the $S_0 \rightarrow S_2$ (π–π*) transition (FIG. 6). BODIPY dyes 14 and 18 display similar absorption features as BODIPY dye 9. The introduction of diiodo substituent to the dipyrromethene core (9, 14 or 18) results in a significant red shift (up to 33 nm and 38 nm) of both the UV-absorption and fluorescent maxima, respectively, and significantly quenches the fluorescence quantum yield because of the heavy atom effect (FIGS. 6-8 and Table 2). Absorption and fluorescence spectra of 2,6-diiodo-substituted BODIPY monomers (10, 15 and 19) exhibit good mirror symmetry with similar band shapes for the absorption and emission spectra which was also verified by measuring their full width at half-maximum (FIG. 6). When low-band-gap BODIPY units are incorporated into the polyfluorene backbone, the fluorescence corresponding to the fluorene segment completely disappears while the emission consists exclusively of one peak at longer wavelength responsible for the BODIPY units. The complete disappearance of the fluorene segment arises from an efficient photoinduced energy transfer from the fluorene segment to the BODIPY unit which functions as a powerful trap in the copolymer backbone. Extended π-conjugation of the polymer III results in significant red shifts (55 nm and 76 nm) of both the UV-absorption and fluorescent maxima, respectively, compared to its starting BODIPY dye 9. As shown in Table 2, the similar red shifts were also observed in polymers IV and V. In addition, fluorescent conjugated copolymers display slightly broader absorption and emission peaks due to extension of π-conjugation compared to their BODIPY monomers, as shown in FIG. 6.

TABLE 2

The UV-visible absorption and emission maxima, and fluorescent quantum yields of BODIPY derivatives and copolymers in CH$_2$Cl$_2$ solution.

| BODIPY | Absorption maxima (nm) | Emission maxima (nm) | Quantum yield |
|---|---|---|---|
| 9 | 502 | 511 | 71.5% |
| 10 | 535 | 549 | 7.52% |
| Polymer III | 557 | 587 | 63.8% |
| 14 | 500 | 510 | 80.1% |
| 15 | 533 | 548 | 5.72% |
| Polymer IV | 547 | 585 | 55.6% |
| 18 | 501 | 510 | 86.7% |
| 19 | 535 | 549 | 8.64% |
| Polymer V | 549 | 588 | 84.8% |

BODIPY dyes with different arylated moieties at the meso position (9, 14 and 18) only display a 1 nm to 2 nm difference between their UV-visible absorption maxima or emission maxima although the substitution position is structurally unique (Table 2). Iodization of BODIPY dyes (9, 14 and 18) at the 2 and 6 positions does not increase this minor difference (Table 1). This minor difference arises from the fact that the arylated moiety is not coplanar with the BODIPY core due to steric hindrance (FIG. 7). As a result, arylation at the meso position does not significantly affect the absorption and emission spectral maxima of BODIPY dyes. The extended π-conjugation of polymers III, IV and V also fails to amplify the minor difference of emission maxima of their monomers. However, as shown in Table 2, BODIPY dyes (9, 14 and 18)

possess different fluorescent quantum yields. BODIPY dye 18 is highly fluorescent with fluorescent quantum yield of 86.7% which is the highest among three BODIPY dyes (9, 14 and 18). Without wishing to be bound by a particular theory, this may be because the ortho-methyl groups on the meso-phenyl ring introduce steric constraints on the phenyl ring, and suppress non-radiative deactivation to increase quantum yield by restricting internal free rotation of the phenyl ring at the meso position relative to the BODIPY core in the excited state (FIG. 7). As a result, polymer V is highly fluorescent with a fluorescent quantum yield of 84.8% in methylene chloride solution, which is higher than those of polymers III and IV.

The UV-visible absorption and emission maxima of BODIPY dyes (9, 10, 14, 15, 18 and 19) are relatively insensitive to the solvent polarity with similar shapes of the UV-visible absorption and emission spectra in methylene chloride and DMF (Tables 2 and 3; FIGS. 6 and 8). The emission maxima of 2,6-diiodo-substituted BODIPY derivatives (10, 15 and 19) undergo bathochromically red shifts by 1-2 nm in more polar solvent, (such as DMF) (Tables 2 and 3). However, the fluorescent quantum yields of all BODIPY dyes (9, 10, 14, 15, 18 and 19) decrease in more polar solvent (DMF) (Tables 2 and 3). The UV-visible absorption and emission maxima of conjugated copolymers III, IV and V are also slightly red-shifted and their fluorescent quantum yields decrease significantly in a more polar solvent (DMF) (Tables 2 and 3; FIGS. 6 and 8). This might arise from increased π-π stacking interactions between the polymer backbones promoted in DMF solution.

TABLE 3

The UV-visible absorption and emission maxima, and fluorescent quantum yields of BODIPY derivatives and copolymers in DMF solution.

| BODIPY | Absorption maxima (nm) | Emission maxima (nm) | Quantum yield |
|---|---|---|---|
| 9 | 501 | 511 | 55.3% |
| 10 | 534 | 551 | 3.4% |
| Polymer III | 564 | 590 | 15.5% |
| 14 | 500 | 510 | 71.6% |
| 15 | 533 | 551 | 4.9% |
| Polymer IV | 554 | 589 | 15.6% |
| 18 | 502 | 510 | 73.8% |
| 19 | 536 | 552 | 4.4% |
| Polymer V | 558 | 590 | 16.4% |

Example 3

Synthesis of Highly Water-Soluble BODIPY-Based Conjugated Glycopolymers

The present Example discloses preparation of a new kind of fluorescent conjugated polymer, poly(2,6-BODIPY-ethynylene)s with deep-red emission at around 680 nm, by palladium-catalyzed Sonogashira polymerization of 2,6-diiodo BODIPY monomers with 2,6-diethynyl BODIPY monomers. Near-infrared emissive poly(2,6-BODIPY-ethynylene)s (XIII-XV) are prepared by 3,5-functionalization of BODIPY dyes with vinylphenyl groups.

Figure 13:
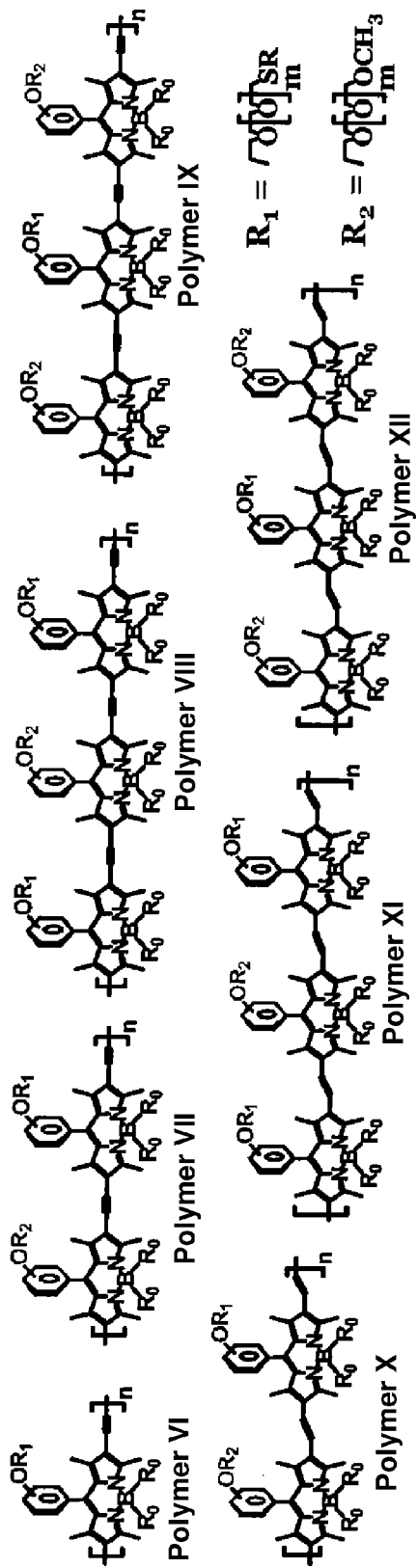
FIG. 13 shows chemical structures of BODIPY-based conjugated glycopolymers.
Figure 13:
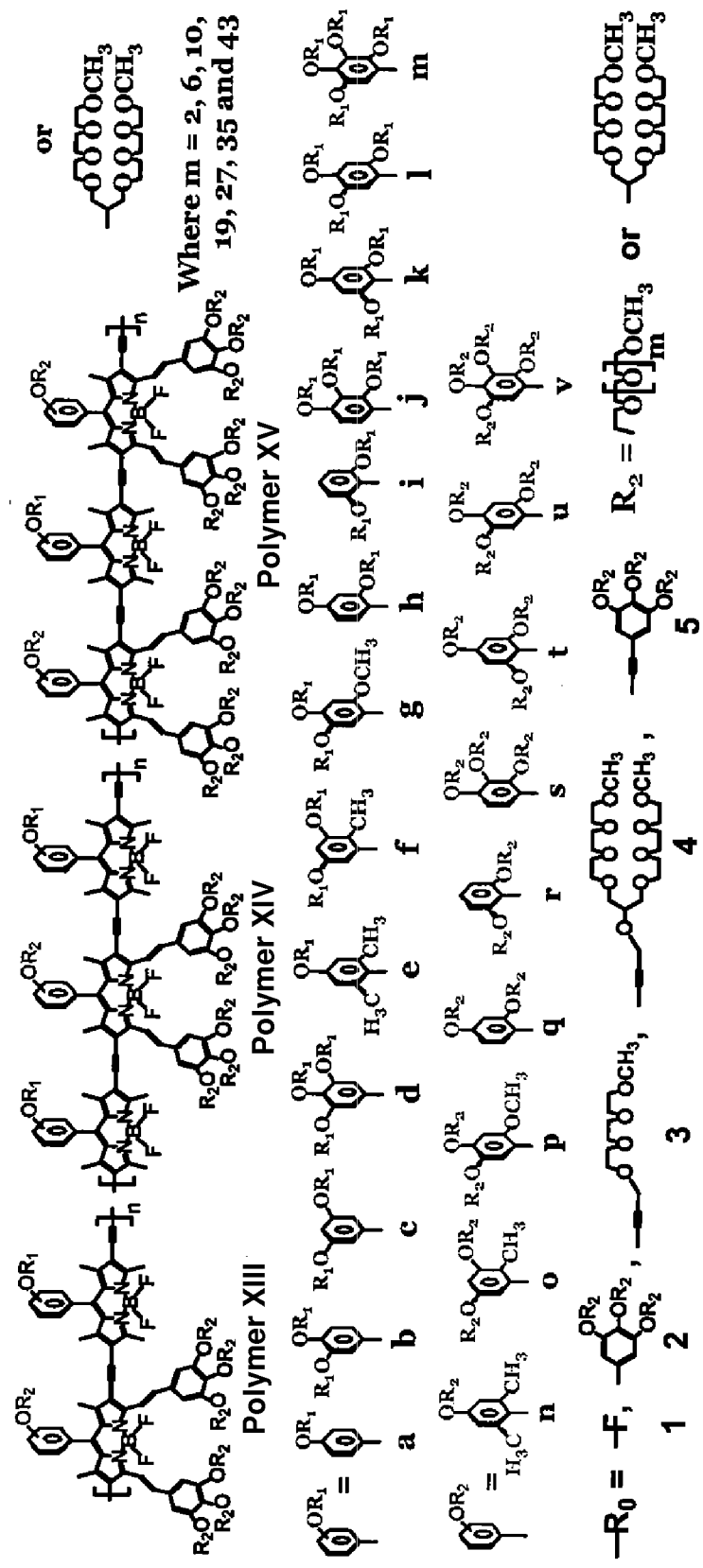

BODIPY-based conjugated glycopolymers are prepared by introducing a variety of carbohydrates (R groups) to the meso-phenyl groups relative to BODIPY cores through well-defined oligo(ethylene glycol) tethered spacers (its repeat unit (m) from 2, 6, 10, 19, 27, 35 to 43) via thioether bridges (FIG. 13).

Carbohydrate density and orientations of BODIPY-based glycopolymers is controlled by controlling functionalization of the meso-phenyl groups (a-m) relative to BODIPY cores with oligo(ethylene glycol) tethered spacers to address the fundamental issues of the multivalent effects in a given system (FIG. 13). In addition, the density, spacing and orientation of carbohydrate units of BODIPY-based conjugated glycopolymers (polymers VII-XV) is controlled by using diluting BODIPY monomers with meso-phenyl groups (n-v) bearing branched groups of oligo(ethylene glycol) monomethyl ether to optimize multivalent cooperative interactions between carbohydrates and pathogenic bacteria or influenza virus, investigate the influence of carbohydrate clustering and orientation on their multivalent interactions with specific receptors since the effectiveness of the chelate effect depends on the spatial match between the receptors and the carbohydrate residues and on the flexibility of the spacer arms (FIG. 13).

Although functionalization of the meso-phenyl groups will not significantly change absorption and emission spectral maxima of BODIPY-based conjugated glycopolymers since the meso-phenyl groups are not coplanar with BODIPY cores, it will affect fluorescence quantum yields of the glycopolymers. In order to enhance fluorescence quantum yields of the glycopolymers in aqueous solution, ortho-substituent groups on the meso-phenyl rings (e-v) are used to introduce steric constraints on the meso-phenyl rings, and suppress non-radiative deactivation by restricting internal free rotation of the phenyl ring at the meso position relative to the BODIPY core in the excited state (FIG. 13). In addition, the bulky ortho-substituent groups on the meso-phenyl ring preclude potential formation of aggregates of the conjugated glycopolymers by prevent π-π stacking interactions between polymer backbones through the enhanced steric hindrances.

In order to further increase stability and fluorescent quantum yields of BODIPY-based conjugated glycopolymers, C-BODIPY- (C for "carbocycle") and E-BODIPY-based (E for "ethynyl") conjugated glycopolymers are prepared by replacing the usual fluorine atoms of F-BODPY dyes with aryl, ethynyl and ethynylaryl subunits (FIG. 13). Although replacement of the usual fluorine atoms with aryl or ethynylaryl subunits will not considerably change absorption and emission spectral maxima of BODIPY-based conjugated glycopolymers, it will not only enhance stability of the glycopolymers in a strong acid or base because of stabilization of the tetrahedral boron center by the ethynyl donors, but also increase water-solubility of the glycopolymers in aqueous solution, and fluorescent quantum yields of the glycopolymers because the bulky aryl, ethynyl or ethynylaryl substituents bearing highly-branched groups of oligo(ethylene glycol)monomethyl ether will increase hydrophilicity of BODIPY dyes, and further prevent π-π stacking interactions between the polymer backbones due to their steric hindrances.

Example 4

Synthesis of BODIPY-Based Near-Infrared Emissive Conjugated Glyco-Copolymers

Figure 14:
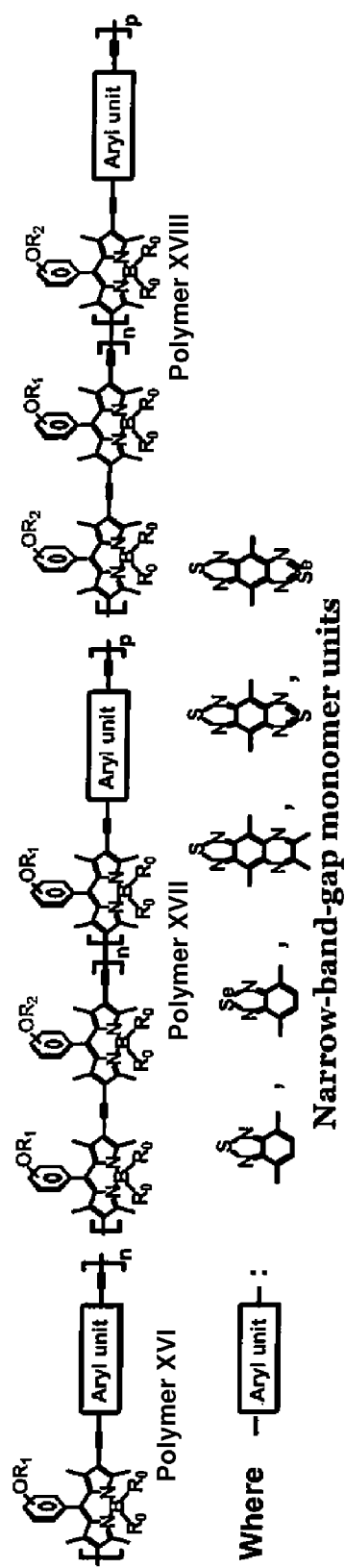
FIG. 14 shows chemical Structures of BODIPY-based conjugated glycol-copolymers.

Different amounts from 5% to 50% of narrow-band-gap monomer units such as 2,1,3-benzoselenadiazole, 6,7-dimethyl[1,2,5]thiadiazolo[3,4-g]quinoxaline and benzo[1,2-c:4,5-c']bis([1,2,5]thiadiazole) are incorporated into backbones of BODIPY-based conjugated glycopolymers to tune polymer fluorescence with near-infrared emissions ranging from 700 nm to 900 nm (FIG. 14).

Example 5

Synthesis of Highly Water-Soluble Conjugated Glycopolymers

Figure 15:
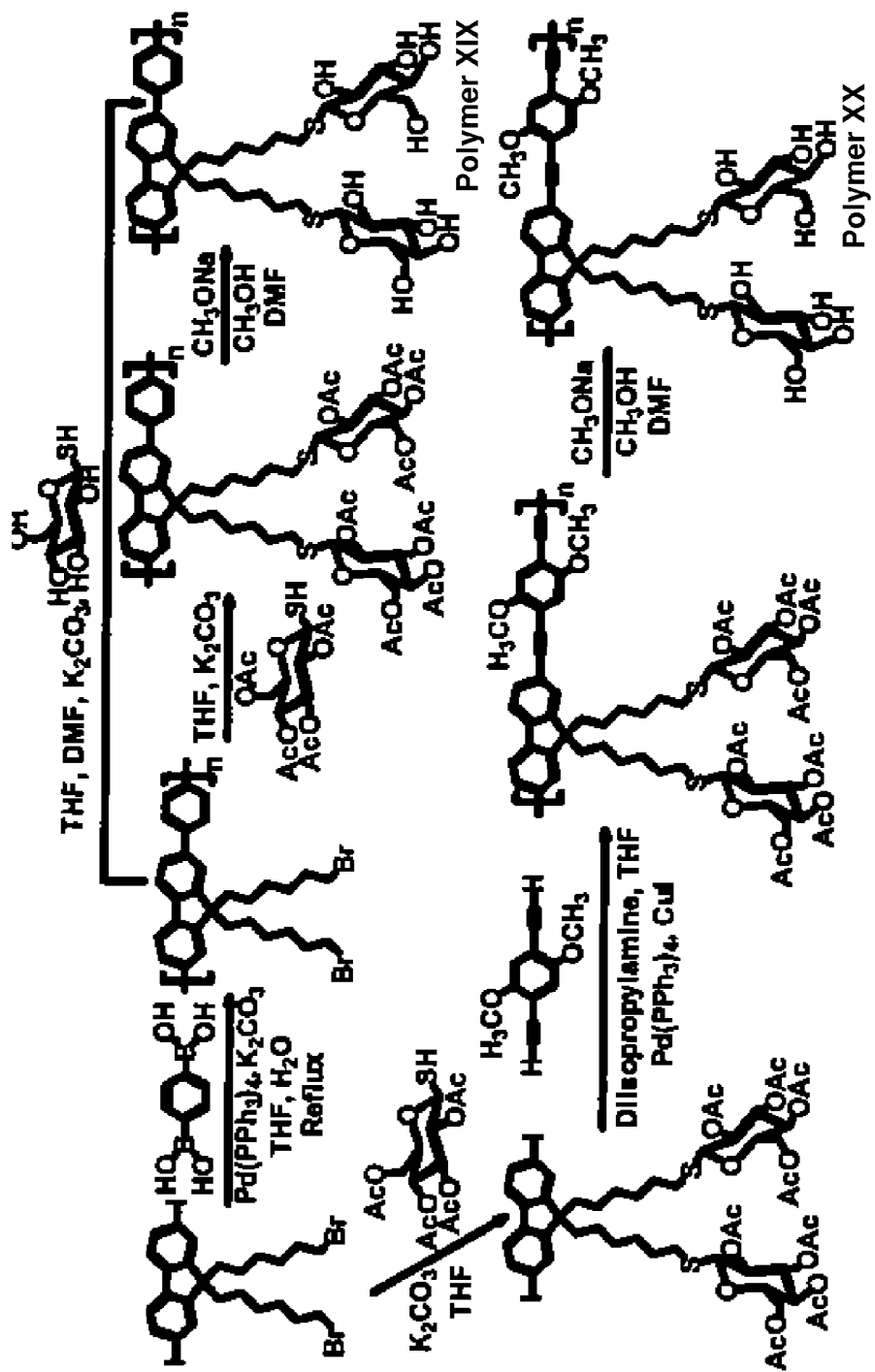
FIG. 15 shows a synthetic route to fluorescent conjugated glyopolymers XIX and XX.
Figure 16:
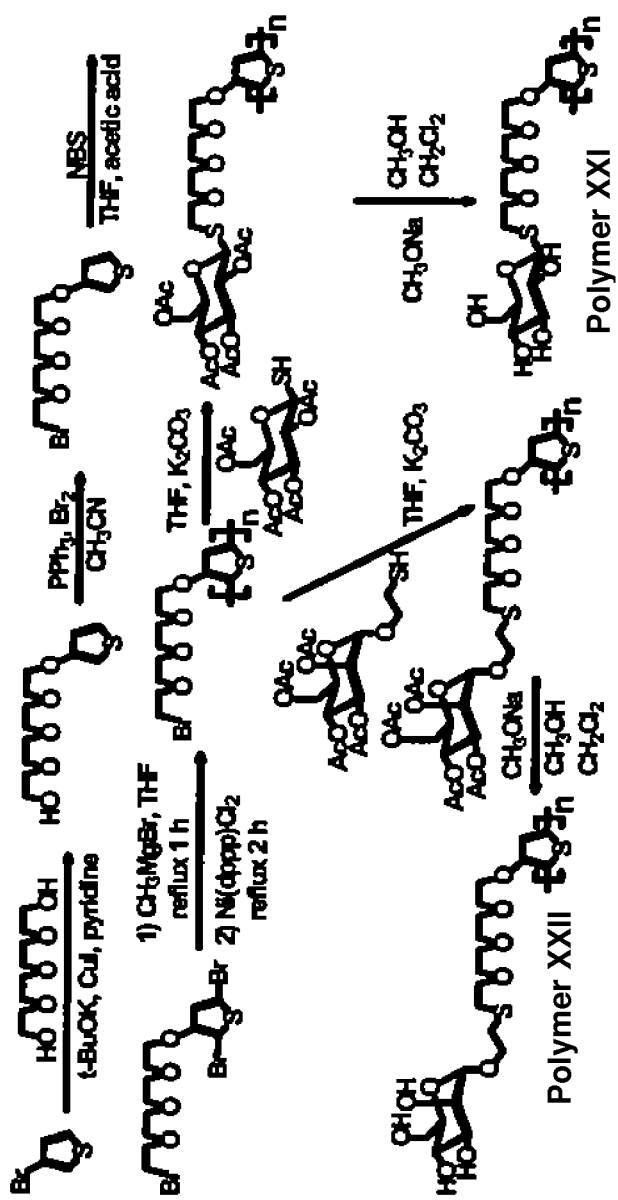
FIG. 16 shows a synthetic route to fluorescent conjugated glycopolythiophenes.
Figure 17:
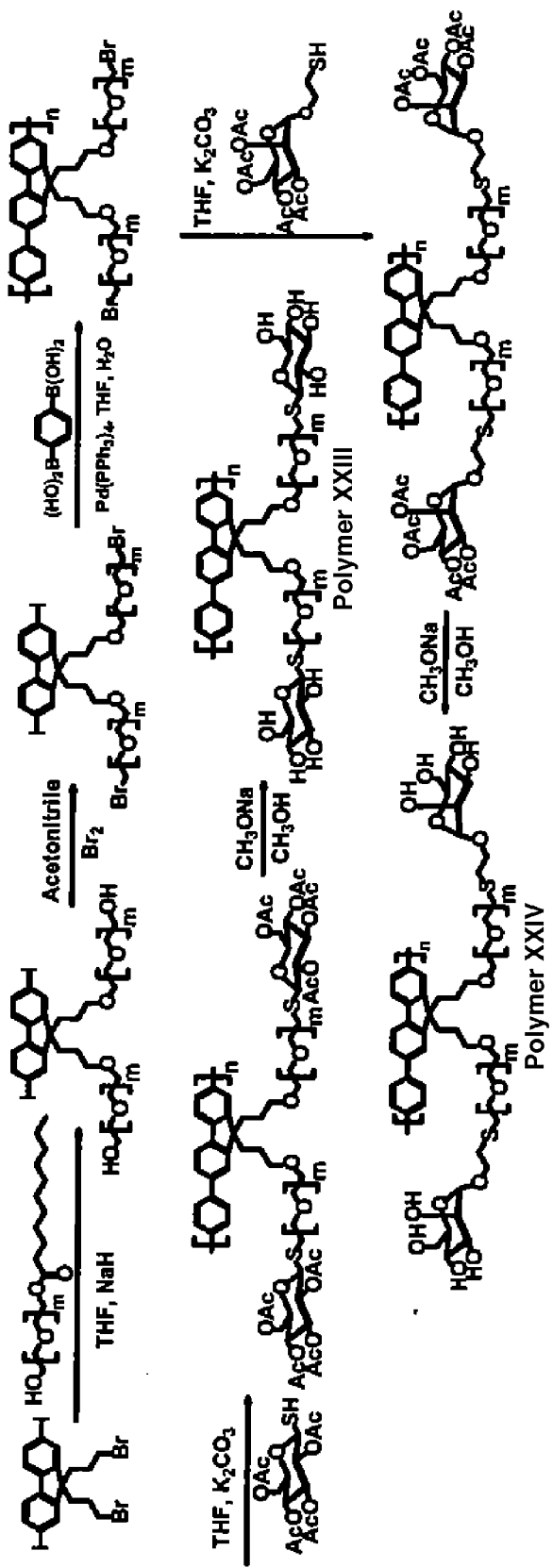
FIG. 17 shows a synthetic route to highly water-soluble fluorene-based β-glucose-bearing and α-mannose bearing conjugated glycopolymers with poly(ethylene glycol) tethered spacers (polymers XXIII and XXIV, respectively).

Facile, versatile pre-polymerization and post-polymerization functionalization approaches to prepare well-defined fluorene-based fluorescent conjugated polymers bearing β-glucose pendants (polymers XIX and XX), and regioregular head-to-tail conjugated glycopolythiophenes (polymers XXI and XXII) through thioether bridges (FIGS. 15 and 16) have been developed. The post-polymerization functionalization approach offers a very effective and fast way to synthesize well-defined fluorescent conjugated glycopolymers bearing a variety of carbohydrate pendants since the post-polymerization reaction of polymeric bromide groups with thiol-carbohydrates is 100% completed in a mild basic condition. Conjugated glycopolythiophenes with tetra(ethylene glycol) tethered spacers (polymers XXI and XXII) are highly soluble in water while the glycopolymers with hydrophobic hexyl tethered spacers (polymers XIX and XX) are insoluble in water. However, fluorene-based conjugated glycopolymers with poly(ethylene glycol) tethered spacers (polymers XXIII and XXIV) are highly soluble in water with high fluorescent quantum yield of 45% due to highly hydrophilic feature of poly(ethylene glycol) tethered spacers (FIG. 17). The repeated unit number (m) of poly(ethylene glycol) tethered spacer is 9.0 (FIG. 17).

Example 6

Synthesis of Deep-Red Emissive Conjugated Poly(BODIPY-Ethynylene)s

Figure 18:
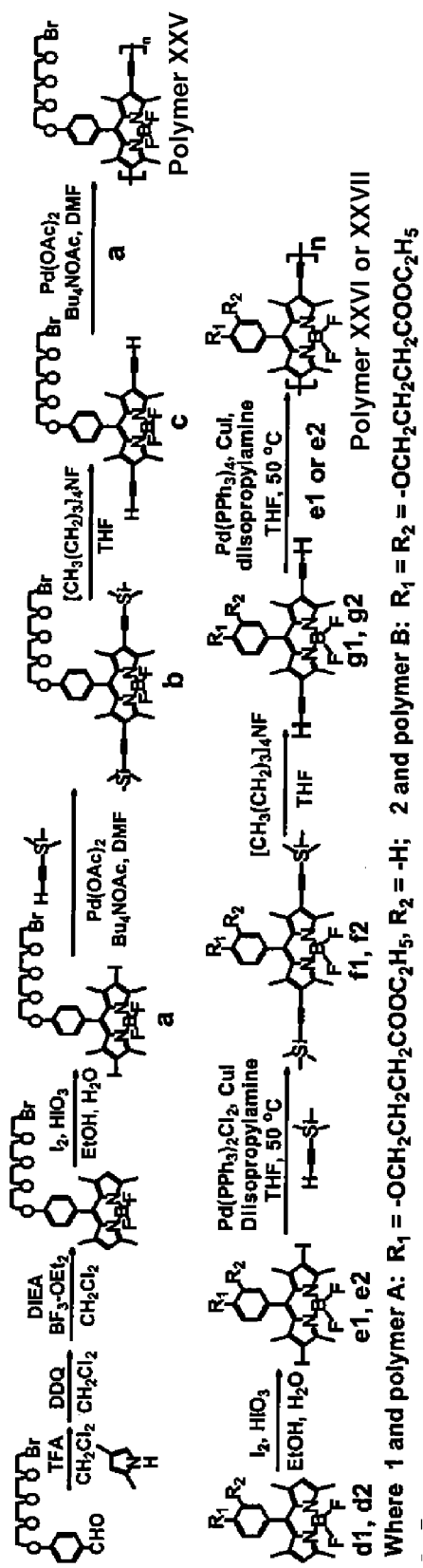
FIG. 18 shows a synthetic route to bromide-bearing poly (BODIPY-ethylene) (polymer I) and ester-bearing poly(BODIPY-ethynylene)s (Polymers) (XVI and XXVII).

Bromide-bearing poly(BODIPY-ethynylene) has been prepared for further functionalization with carbohydrates or peptides through thioether bridges (FIG. 18). The synthetic strategy to prepare bromide-bearing poly(BODIPY-ethynylene)s is detailed in Example 7. Bromide-bearing poly (BODIPY-ethynylene) (polymer XXV) was prepared by palladium-catalyzed Sonogashira polymerization of 2,6-diiodo BODIPY monomer (a) with 2,6-diethynyl BODIPY monomer (c) in DMF solution in presence of Pd(OAc)$_2$ and tetrabutylammonium acetate (FIG. 18).35

Figure 19:
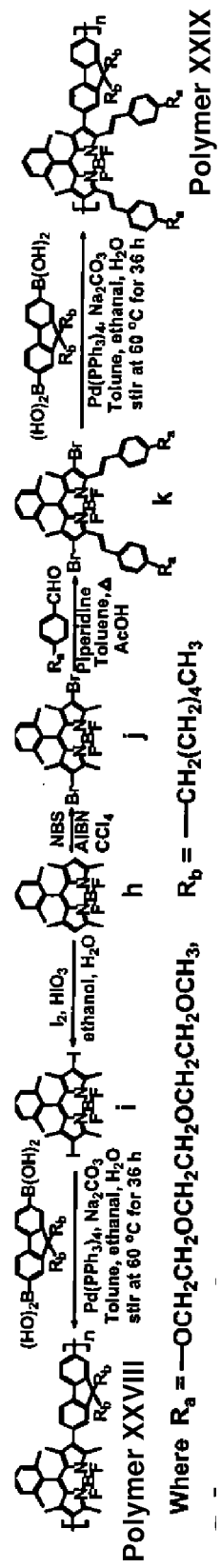
FIG. 19 shows a synthetic route to BODIPY-based copolymers (polymers XXVIII and XXIX).

Deep-red emissive poly(BODIPY-ethynylene)s bearing ethyl phenoxybutanoate groups at the meso-positions (polymers XXVI and XXVII) have also been prepared. (FIG. 18). Poly(BODIPY-ethynylene)s emit in deep-red region with fluorescent spectral maxima at around 680 nm and display significant red shifts (up to 163 nm and 172 nm) of both absorption and emission maxima compared with their starting BODIPY dyes (d1, d2) (Table 4). In addition, BODIPY-based copolymers have been prepared. (FIG. 19). Polymer XXVIII emits in orange region at 588 nm and shows significant red shifts to 48 nm and 78 nm) of both absorption and emission maxima compared with their starting BODIPY dye (h). Polymer XXIX emits at 616 nm (corresponding to fluorene moiety) and 680 nm (corresponding to BODIPY moiety), and show no shift in both absorption and emission maxima compared with BODIPY dye (K) in $CH_2Cl_2$. All BODIPY-based polymers are highly florescent with 84.8% of fluorescent quantum yield for polymer XXVIII.

TABLE 4

Absorption and emission maxima of BODIPY dyes and polymers in methylene chloride.

| BODIPY | d1 | e1 | f1 | g1 | Polymer XXVI | d2 | e2 | f2 | g2 | Polymer XXVII |
|---|---|---|---|---|---|---|---|---|---|---|
| Absorption maxima (nm) | 501 | 533 | 553 | 538 | 659 | 502 | 534 | 554 | 539 | 665 |
| Emission maxima (nm) | 510 | 548 | 569 | 552 | 678 | 511 | 549 | 570 | 553 | 683 |

Example 7

Synthesis of Highly Water-Soluble BODIPY-Based Conjugated Glycopolymers

Highly water-soluble BODIPY-based deep-red and near-infrared emissive fluorescent conjugated glycopolymers with controlled carbohydrate density and orientation, and apply these glycopolymers in detection of pathogenic bacteria and virus is described.

Synthesis of Deep-red Emissive Conjugated Glycopoly(F-BODIPY-ethynylene)s.

Figure 20:
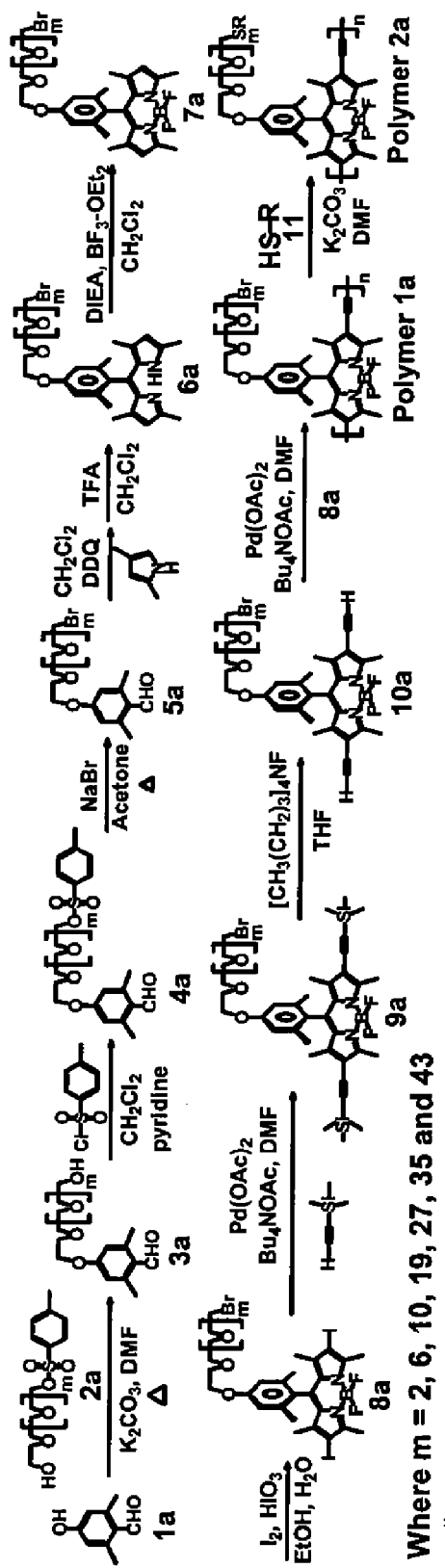
FIG. 20 shows a synthetic route to BODIPY dyes.

FIG. 20 outlines synthetic route to conjugated poly(F-BODIPY-ethynylene) through a well-developed postpolymerization functionalization approach. Monotosylate oligo(ethylene glycol) (2a) will be prepared by reacting oligo(ethylene glycol) with a stoichiometric amount of p-toluenesulfonyl chloride in the presence of silver(I) oxide and a catalytic amount of potassium iodide. Various well-defined oligo(ethylene glycol)s will be used and their repeated units (m) will be varied from 2, 6, 10, 19, 27, 35 to 43. Bromide-bearing formal benzene derivative (5a) will be prepared by reacting monotosylated oligo(ethylene glycol) (2a) with 4-hydroXY-2,6-dimethylbenzaldehyde (1a), and followed tosylation of an alcohol (3a), and replacement of tosylate group with bromide ion. Bromide-bearing BODIPY dye (7a) will be prepared through the reaction of the formyl benzene derivative (5a) with an excess of 2,4-dimethylpyrrole under acid catalysis, and followed by oxidization with 2,3-dichloro-5,6-dicyano-1,4-benzoquinone (DDQ) and treatment with $BF_3$-etherate in the presence of N,N-diisopropylethylamine (DIEA) (FIG. 20). Further iodination of BODIPY dye (7a) will afford 2,6-diiodo-tetramethyl BODIPY monomer (8a). 2,6-Diethynyl BODIPY monomer (10a) will be prepared by palladium-catalyzed Sonogashira reaction of monomer 8a with ethynyltrimethylsilane in DMF solution in the presence of Pd(OAc)$_2$ and tetrabutylammonium acetate, affording BODIPY dye (9a), and followed by hydrolysis of compound 9a in the presence of tetrabutylammonium fluoride. Bromide-bearing conjugated Poly(BODIPY-ethynylene) (polymer 1a) will be synthesized by palladium-catalyzed Sonogashira polymerization of 2,6-diiodo BODIPY monomers (8a) with 2,6-diethynyl BODIPY monomer (10a) in DMF solution in presence of Pd(OAc)$_2$ and tetrabutylammonium.

A series of well-defined glycopoly(BODIPY-ethynylene)s (polymer 2a) bearing different carbohydrate residues will be prepared by postpolymerization functionalization of polymer 1a with a little excess of thiol-functionalized carbohydrate (11) in DMF in a mild basic condition ($K_2CO_3$) through 100% thioether formation (Table 5). The glycopolymer will be put in a cellulose dialysis tube, dialysized against a large amount of water and lyophilized. Different oligo(ethylene glycol)s (m=2, 6, 10, 19, 27, 35 and 43) will be used as a tethered spacers between polymer backbone and carbohydrate residues. Long oligo(ethylene glycol) (m>10) will be needed to make polymer 2a soluble in water since polymer 2a will have only one tethered spacer and BODIPY unit is hydrophobic. Polymer 2a is expected to have high fluorescent quantum yield with emission maximum at 680 nm according to our preliminary results above because the ortho-methyl groups on the meso-phenyl ring introduce steric constraints on the phenyl ring, and suppress non-radiative deactivation to increase quantum yield by restricting internal free rotation of the phenyl ring at the meso position relative to the BODIPY core in the excited state.

A library of highly water-soluble deep-red emissive conjugated glycopoly(F-BODIPY-ethynylene)s with well-controlled carbohydrate density and orientation will be prepared by using different starting aldehyde derivatives (Ib-1m) and tosylated compound (2a-2C) according to the synthetic approach outlined in FIG. 20. Table 5 outlines a library of BODIPY-based conjugated glycopolymers with different lengths of tethered spacers, carbohydrate densities and orientations, and carbohydrate residues. Different numbers and positions of oligo(ethylene glycol) tethered spacers on the meso-phenyl ring relative to each BODIPY unit will be used to control carbohydrate density and orientation, and water-solubility and fluorescent quantum yields of the glycopolymers. The library of the glycopolymers will be prepared by Sonogashira polymerization of one or two (1.0 equivalent) of 2,6-diodio monomers (10a-10m) with one, or two (1.0 equivalent) of 2,5-diethynyl monomers (8a-8m, 8n-8v), and followed by postpolymerization functionalization of bromide-bearing polymers with different thiol-functionalized carbohydrates (11) (Tables 5 and 6). Monomers 8n-8v, and 10n-10v will be used as diluting co-monomers to control carbohydrate density of the glycopolymers, and facilitate water-solubility of the glycopolymers.

TABLE 5

Thiol-functionalized carbohydrates (R—SH) (11)[40-55] in FIGS. 20-24

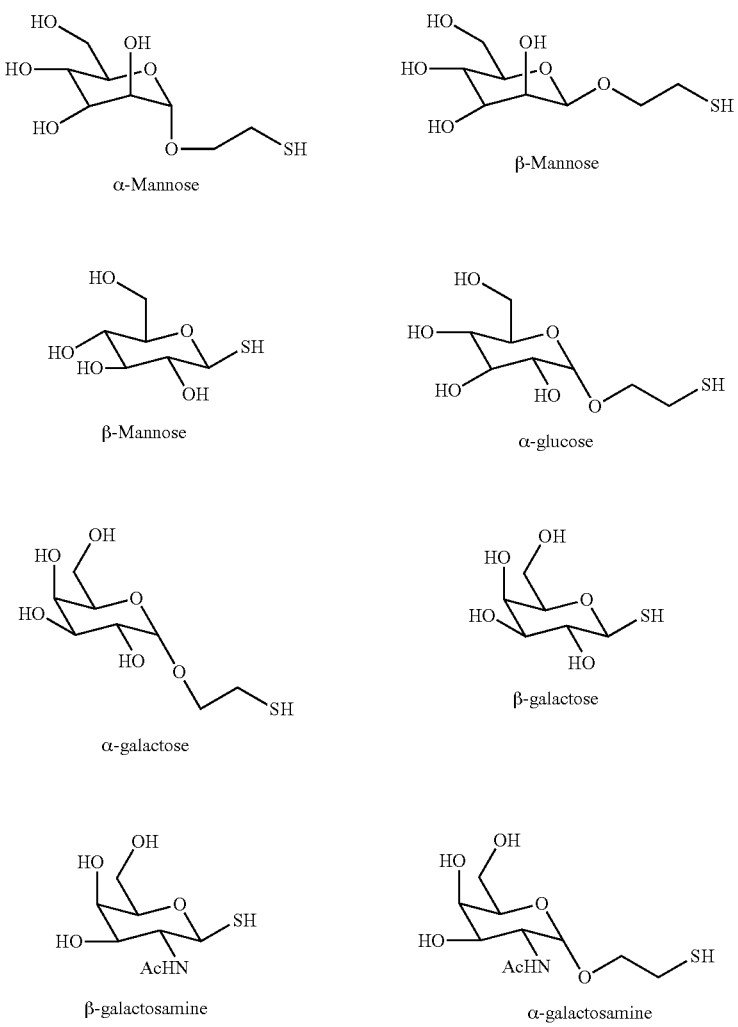

TABLE 5-continued
Thiol-functionalized carbohydrates (R—SH) (11)[40-55] in FIGS. 20-24
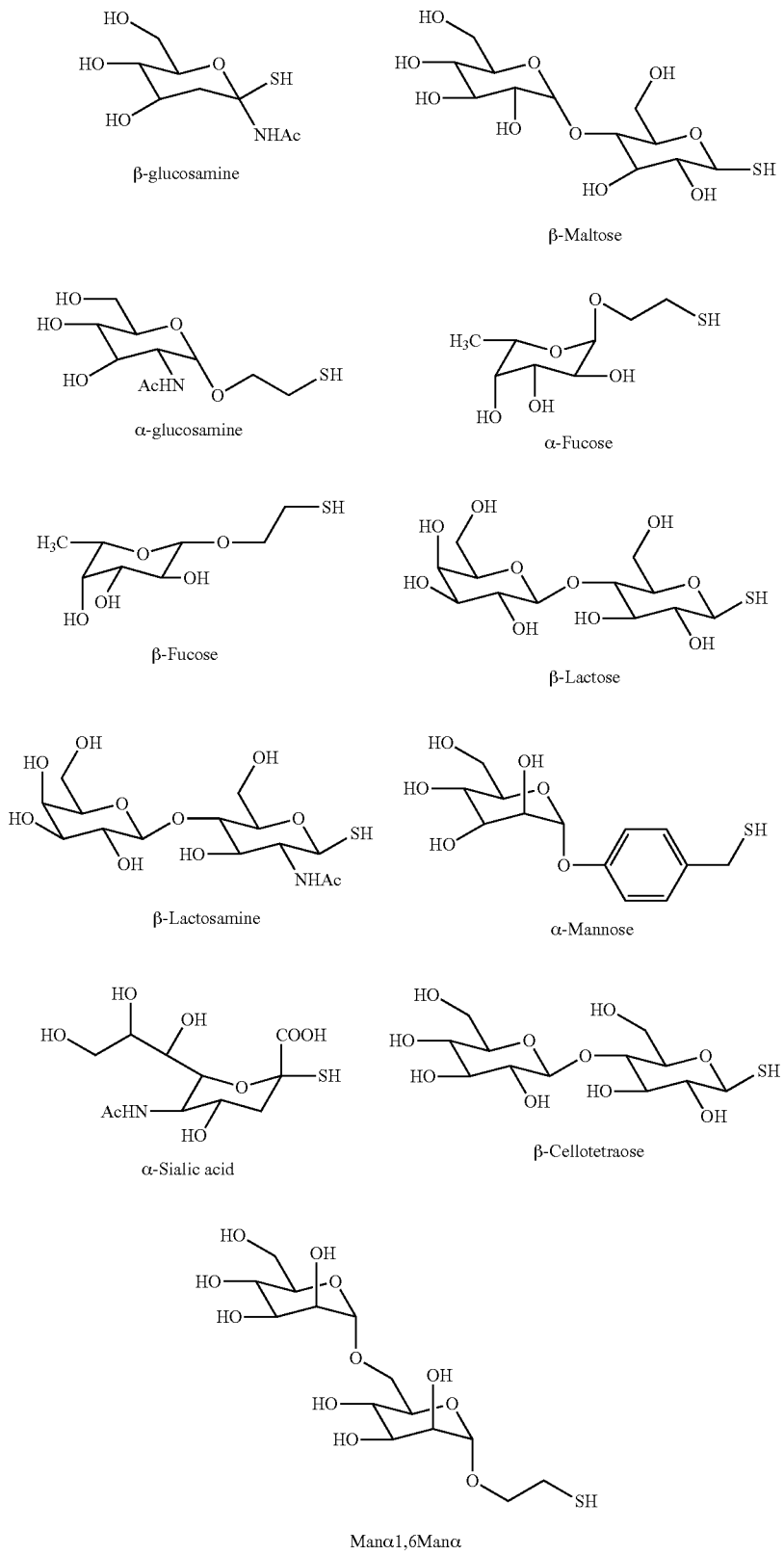

TABLE 5-continued
Thiol-functionalized carbohydrates (R—SH) (11)[40-55] in FIGS. 20-24
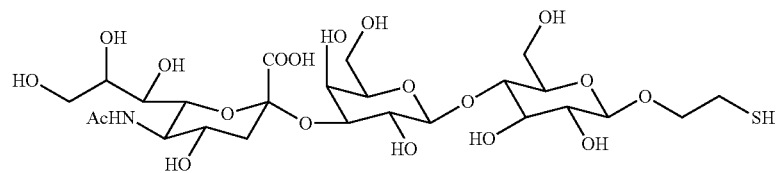
NeuAcα2,3Galβ1,4Glcβ
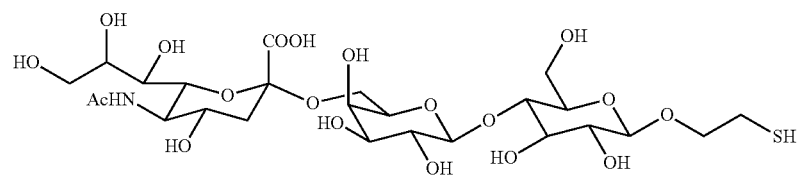
NeuAcα2,6Galβ1,4Glcβ
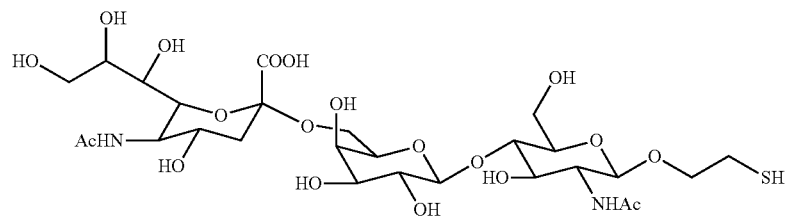
NeuAcα2,6Galβ1,4GlcNacβ
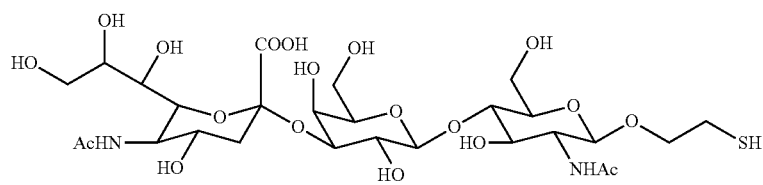
NeuAcα2,3Galβ1,4GlcNacβ
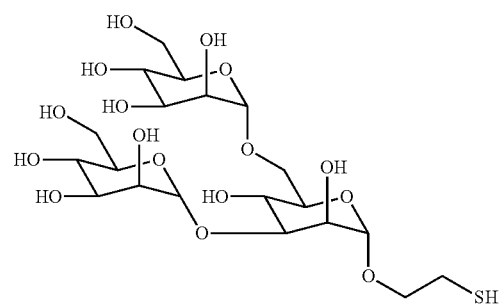
Manα1,3[Manα1,6]Manα

TABLE 6
Starting materials (1b-1m, and 2b-2c), bromide-bearing BODIPY monomers (8a-8m and 10a-10m), diluting monomers (8n-8v and 10n-10v), bromide-bearing poly(2,6-BODIPY-ethynylene)s (polymers) 1a-1m, 1n-1v, 3a-3z, and 4a-4z), and glycopoly(2,6-BODIPY-ethynylene)s (polymers VI, VII, VIII and IX).
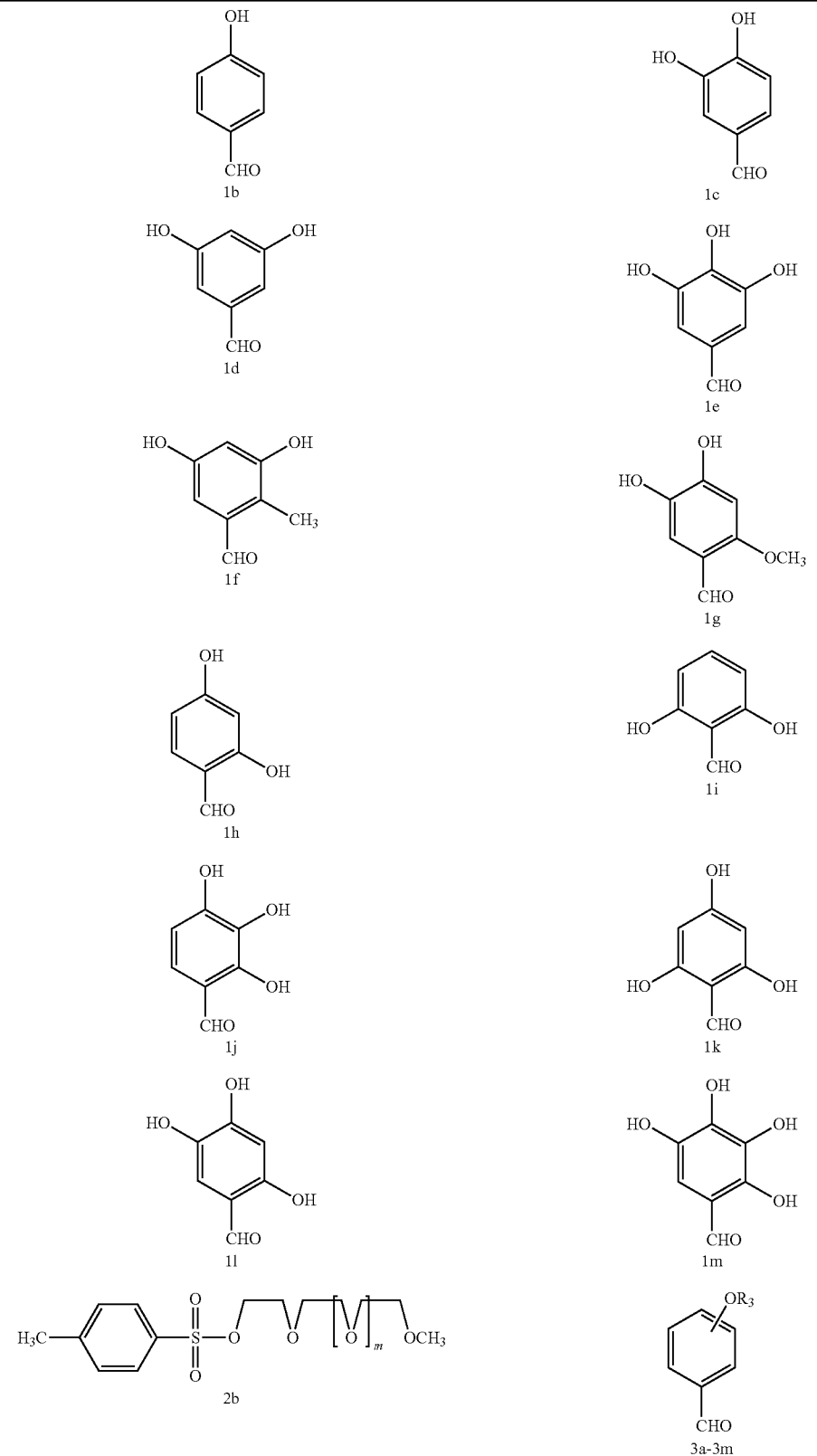

TABLE 6-continued
Starting materials (1b-1m, and 2b-2c), bromide-bearing BODIPY monomers (8a-8m and 10a-10m), diluting monomers (8n-8v and 10n-10v), bromide-bearing poly(2,6-BODIPY-ethynylene)s (polymers) 1a-1m, 1n-1v, 3a-3z, and 4a-4z), and glycopoly(2,6-BODIPY-ethynylene)s (polymers VI, VII, VIII and IX).
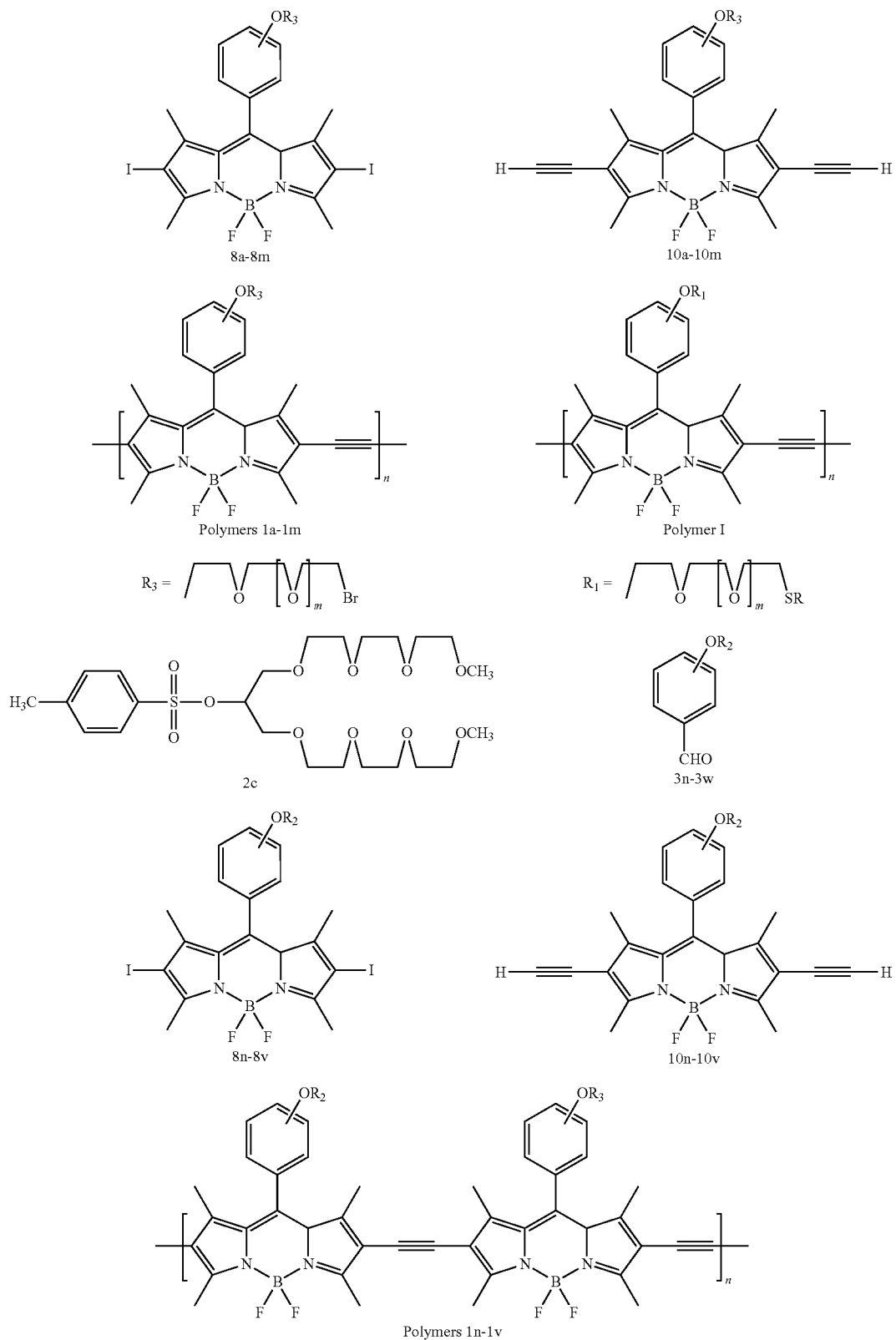

TABLE 6-continued
Starting materials (1b-1m, and 2b-2c), bromide-bearing BODIPY monomers (8a-8m and 10a-10m), diluting monomers (8n-8v and 10n-10v), bromide-bearing poly(2,6-BODIPY-ethynylene)s (polymers) 1a-1m, 1n-1v, 3a-3z, and 4a-4z), and glycopoly(2,6-BODIPY-ethynylene)s (polymers VI, VII, VIII and IX).
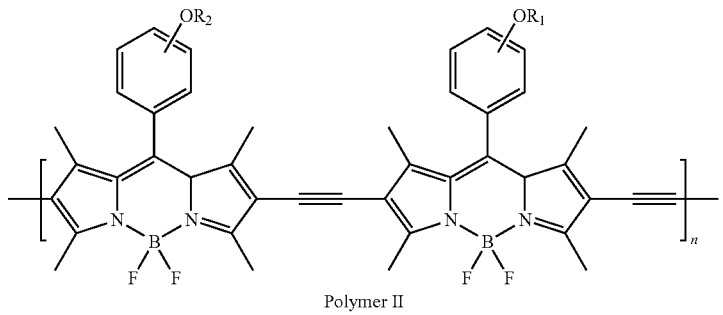
Polymer II
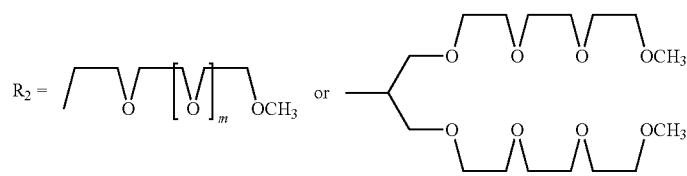
Where m = 2, 6, 10, 19, 27, 35 and 43
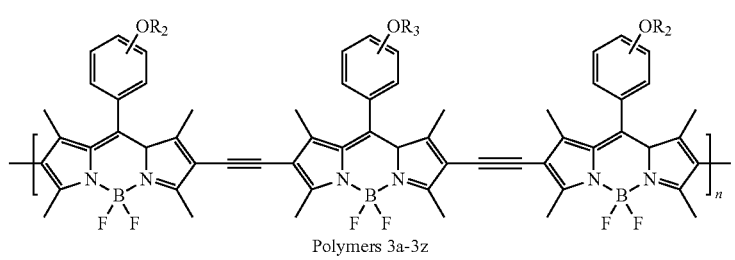
Polymers 3a-3z
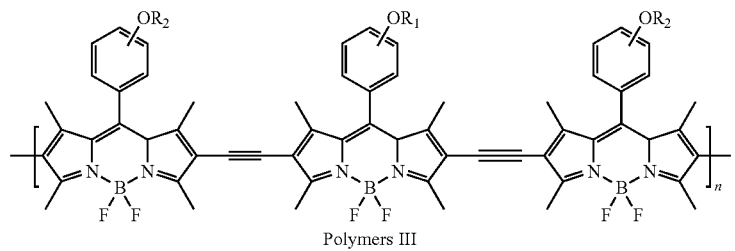
Polymers III
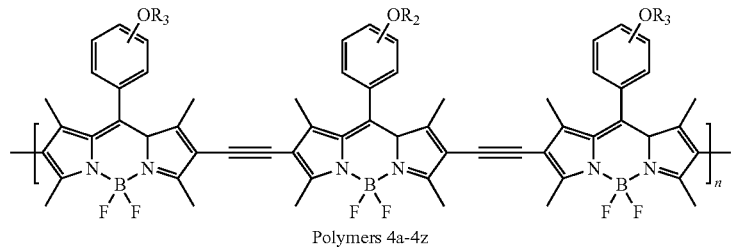
Polymers 4a-4z
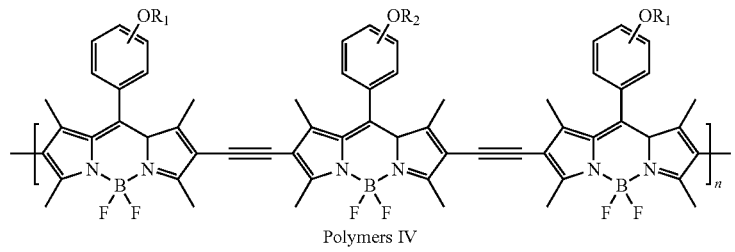
Polymers IV TABLE 6-continued
Starting materials (1b-1m, and 2b-2c), bromide-bearing BODIPY monomers (8a-8m and 10a-10m), diluting monomers (8n-8v and 10n-10v), bromide-bearing poly(2,6-BODIPY-ethynylene)s (polymers) 1a-1m, 1n-1v, 3a-3z, and 4a-4z), and glycopoly(2,6-BODIPY-ethynylene)s (polymers VI, VII, VIII and IX).
Where
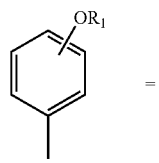 = 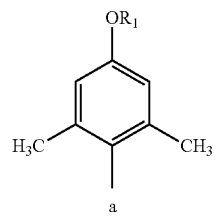
a
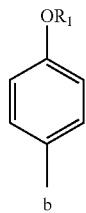
b
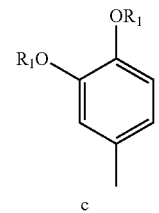
c
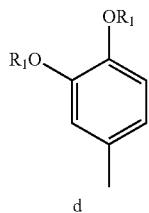
d
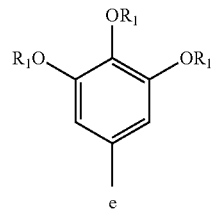
e
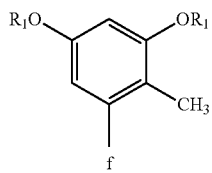
f
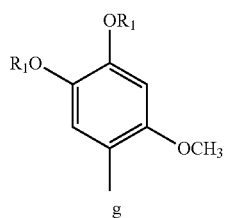
g
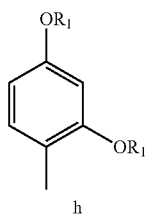
h
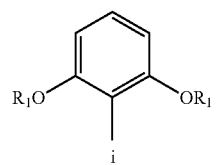
i
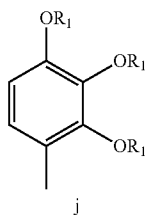
j
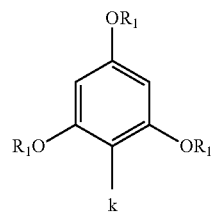
k TABLE 6-continued
Starting materials (1b-1m, and 2b-2c), bromide-bearing BODIPY monomers (8a-8m and 10a-10m), diluting monomers (8n-8v and 10n-10v), bromide-bearing poly(2,6-BODIPY-ethynylene)s (polymers) 1a-1m, 1n-1v, 3a-3z, and 4a-4z), and glycopoly(2,6-BODIPY-ethynylene)s (polymers VI, VII, VIII and IX).
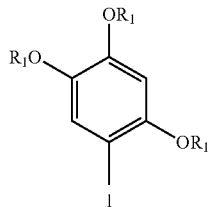
l
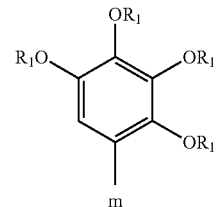
m
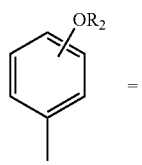
=
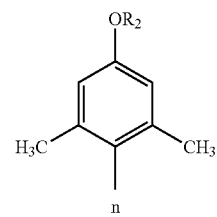
n
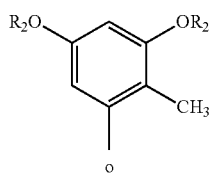
o
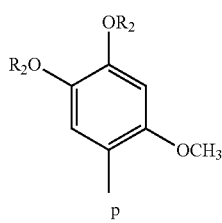
p
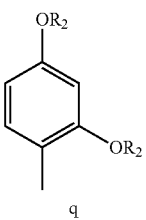
q
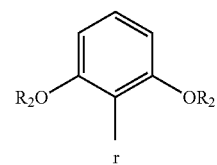
r
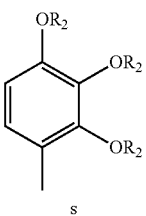
s
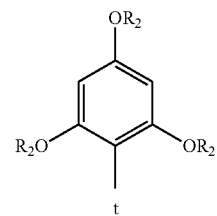
t
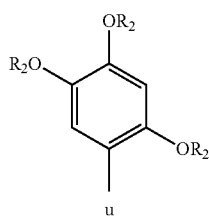
u
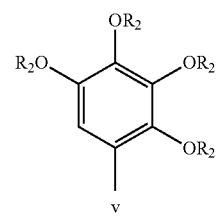
v
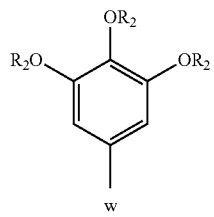
w Anticipated Results:

Multi-substituent groups of oligo(ethylene glycol) on each of meso-phenyl ring relative to BODIPY core will make BODIPY-based conjugated glycopolymers highly soluble in aqueous solution. Ortho-substituent groups on the meso-phenyl rings (e-v) will introduce steric constraints on the meso-phenyl rings, and suppress non-radiative deactivation by restricting internal free rotation of the phenyl ring at the meso position relative to the BODIPY core in the excited state to increase fluorescence quantum yields of the glycopolymers in aqueous solution. In addition, the bulky ortho-substituent groups on the meso-phenyl ring with preclude potential formation of aggregates of the conjugated glycopolymers by preventing π-π stacking interactions between polymer backbones through the enhanced steric hindrances. The polymerization time will be prolonged due to the bulky ortho-substituent groups on meso-phenyl ring relative to BODIPY core.

Example 8

Figure 21:
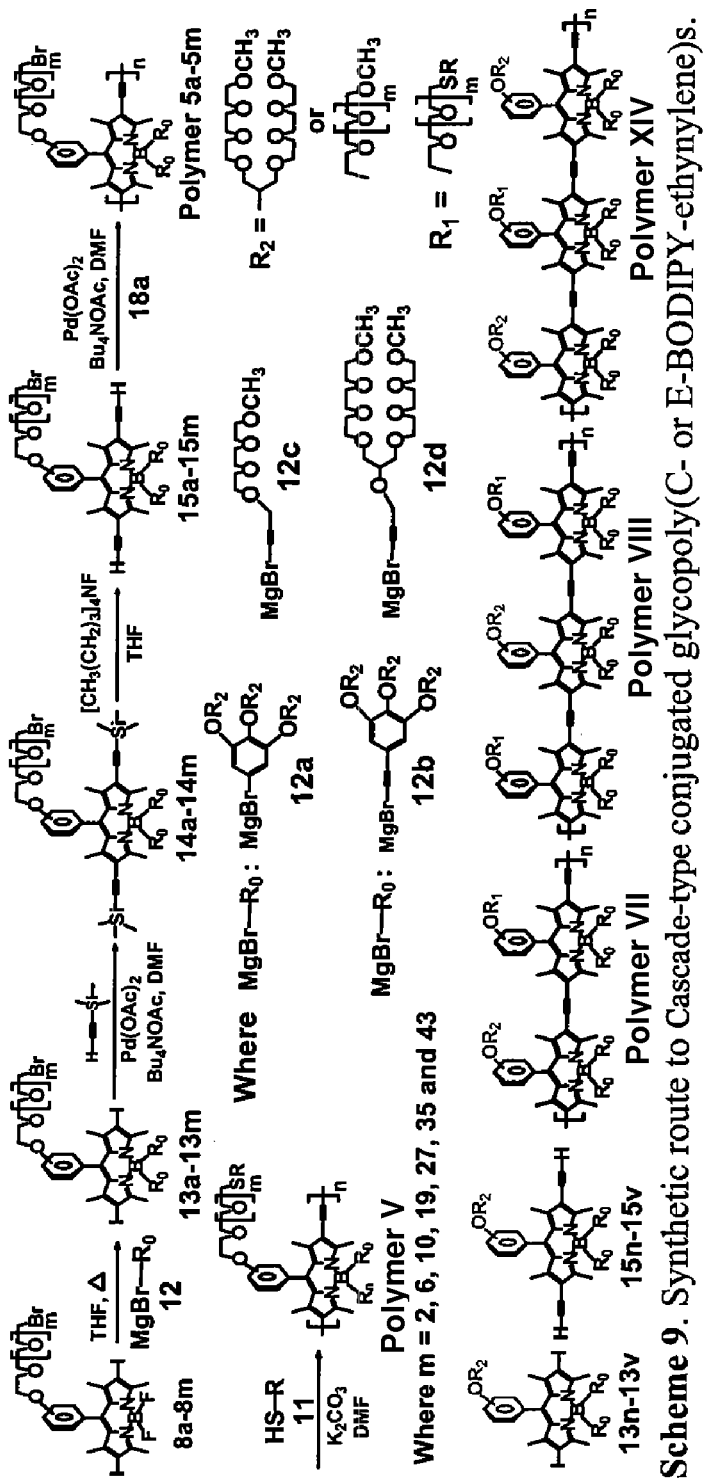
FIG. 21 shows a synthetic route to BODIPY dyes.

Synthesis of Cascade-type Deep-red Emissive Glycopoly(C-BODIPY-ethynylene)s and Glycopoly(E-BODIPY-ethynylene)s In order to further increase stability and fluorescent quantum yields of BODIPY-based conjugated glycopolymers, a library of cascade-type C-BODIPY (C for carbocycle) and E-BODIPY (E for ethynyl) dyads are prepared by replacing the fluorine atoms with aryl, ethynyl and ethynylaryl subunits to incorporate conjugated polymer backbones. Grignard reagents have been used to efficiently substitute the fluorine atoms and E-BODIPY dyes are reported to be very stable and insensitive to strong base or acid, as well as polar solvents and reagents, which is due to stabilization of the tetrahedral boron center by the ethynyl donors. A series of C- or E-BODIPY monomers (13a-13m, 13n-13v) are prepared by reacting 2,5-diiodo BODIPY monomers (8a-8m, 8n-8v) in Table 6 with Grignard reagents (12a, 12b, 12C or 12d) in dry THF at 60° C. The bromide groups of BODIPY dyes (8a-8m) will be intact under Grignards reaction condition. 2,6-Diethynyl C- or E-BODIPY monomers (15a-15m, 15n-15v) are prepared by palladium-catalyzed Sonogashira reaction of monomers (13a-13m, 13n-13v) with ethynyltrimethylsilane in DMF solution in the presence of Pd(OAc)$_2$ and tetrabutylammonium acetate, affording BODIPY dyes (14a-14m, 14n-14v), and followed by hydrolysis of intermediates (14a-14m, 14n-14v) in the presence of tetrabutylammonium fluoride. Bromide-bearing conjugated Poly(BODIPY-ethynylene)s (polymers 5a-5m) are synthesized by palladium-catalyzed Sonogashira polymerization of one of 2,6-diiodo C- or E-BODIPY monomers (13a-13m) with one of 2,6-diethynyl C- or E-BODIPY monomers (15a-15m) in DMF solution in the presence of Pd(OAc)$_2$ and tetrabutylammonium acetate (FIG. 21). Well-defined glycopoly(C- or E-BODIPY-ethynylene)s (polymers XXV) bearing different carbohydrate residues are prepared by post-polymerization functionalization of bromide-bearing polymers 5a-5m with a little excess of thiol-functionalized carbohydrate (11) in DMF in a mild basic condition (K$_2$CO$_3$) through 100% thioether formation (Table 5). Polymers VII, VIII, XIX with controlled density of carbohydrate residues will be prepared by polymerizing one or two (1.0 equivalent) of monomers 15a-15m with one or two (1.0 equivalent) of monomers 13n-13v according to the approach for polymer XXV (FIG. 21).

Anticipated Results:

Replacement of the fluoride atoms with aryl, ethynyl and ethynylaryl subunits will not only significantly enhance stability of glycopoly(C- or E-BODIPY-ethynylene)s in a strong acid or base because of stabilization of the tetrahedral boron centers by the ethynyl donors, but also further increase water-solubility of the glycopolymers in aqueous solution, and fluorescent quantum yields of the glycopolymers because the bulky aryl, ethynyl, ethynylaryl substituents bearing highly-branched groups of oligo(ethylene glycol)monomethyl ether will significantly increase hydrophilicity of BODIPY dyes, and further prevent π-π stacking interactions between the polymer backbones. Polymerization time may need to be prolonged due to introduction of bulky groups to the monomers.

Example 9

Synthesis of Near-infrared Emissive Glycopoly(F-, C- and E-BODIPV-vinylene)s

Figure 22:
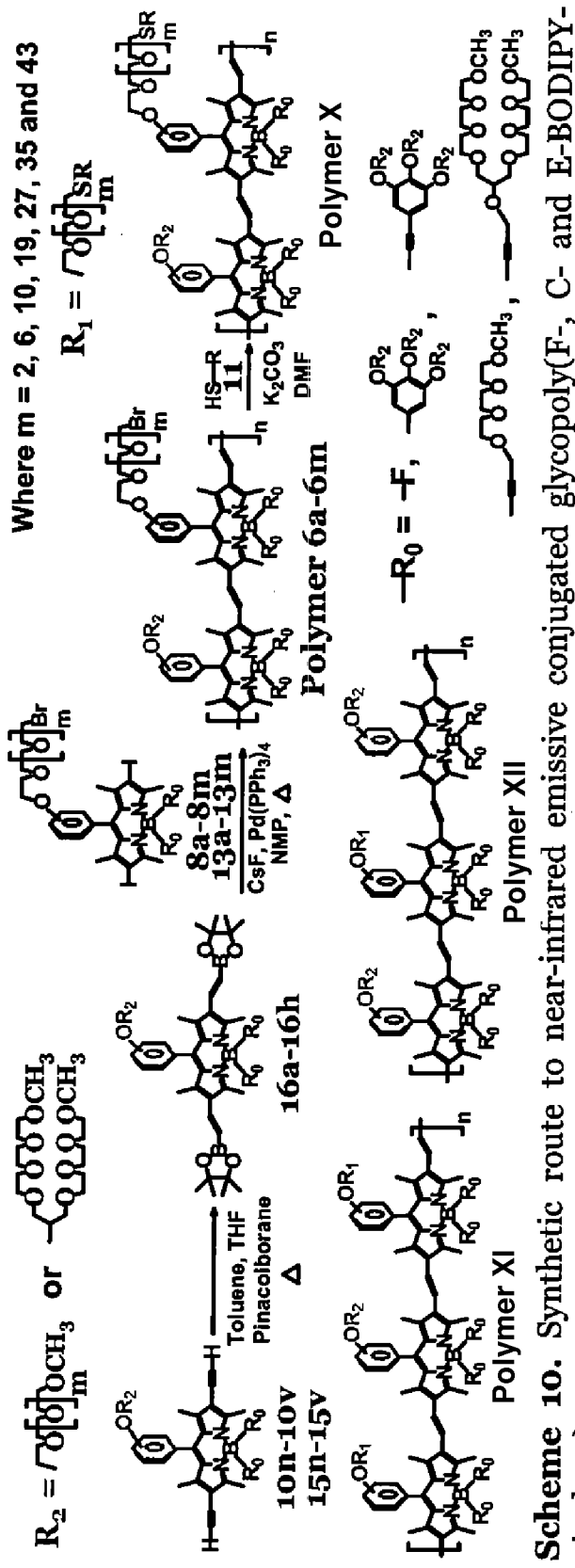
FIG. 22 shows a synthetic route to BODIPY dyes.

According to our preliminary results, poly(BODIPY-ethynylene)s emit deep-red emission with emission spectral maximum at 680 nm. In order to tune the fluorescence of conjugated glycopolymers with near-infrared emission, highly water-soluble glycopoly(BODIPY-vinylene)s are prepared which emit near-infrared emission due to more extended π-conjugation of their polymer backbones than those of poly(BODIPY-ethynylene)s (FIG. 22). 2,6-bis(4,4,5,5-tetramethyl-1,3,2-dioxoborolan-2-yl-ethenyl) BODIPY monomers (16a-16h) are obtained by reaction of one of 2,6-diethynyl F-, C- or E-BODIPY monomers (10n-10v, 15n-15v) in Table 6 and FIG. 21 with 4,4,5,5-tetramethyl-1,3,2-dioxaborolane (pinacolborane) in mixed solution of THF and toluene at 80° C. Glycopoly(BODIPY-vinylene)s (polymers X) are prepared by palladium-catalyzed Suzuki polymerization of one (1.0 equivalent) of BODIPY monomers (16a-16h) with one of bromide-bearing 2,6-diiodo BODIPY monomers (8a-8m, 13a-13m) in 1-methyl-2-pyrrolidinone (NMP) solution at 90° C., affording bromide-bearing poly(BODIPY-vinylene)s (polymers 6a-6m), and followed by postpolymerization functionalization of bromide-bearing poly(BODIPY-vinylene)s (polymers 6a-6m) with thiol-functionalized carbohydrates (11) in Table 4. A library of glycopoly(BODIPY-vinylene)s with various carbohydrate density and orientation (Polymers XI and XII) are prepared by polymerizing one or two (1.0 equivalent) of BODIPY monomers (16a-16h) with one or two (1.0 equivalent) of BODIPY monomers (8a-8m, 13a-13m) in Table 6 and FIG. 21 for a series of bromide-bearing poly(F-, C- and E-BODIPY-vinylene)s, and followed by functionalization of the bromide-bearing polymers with thiol-functionalized carbohydrates (11) in Table 5 (FIG. 22).

Anticipated Results:

Bromide groups of monomers (8a-8m, 13a-13m) will be intact in palladium-catalyzed Suzuki polycondensation. Glycopoly(F-, C- and E-BODIPY-vinylene)s (polymer X-XII) will emit in near-infrared region with emission maxima larger than 700 nm due to their more extended π-conjugation than deep-red emissive poly(F-, C-, E-BODIDPY-ethynylene)s (polymers X-XIV).

Example 10

Synthesis of Near-infrared Emissive Glycopoly(F-BODIPY-ethynylene)s

Figure 23:
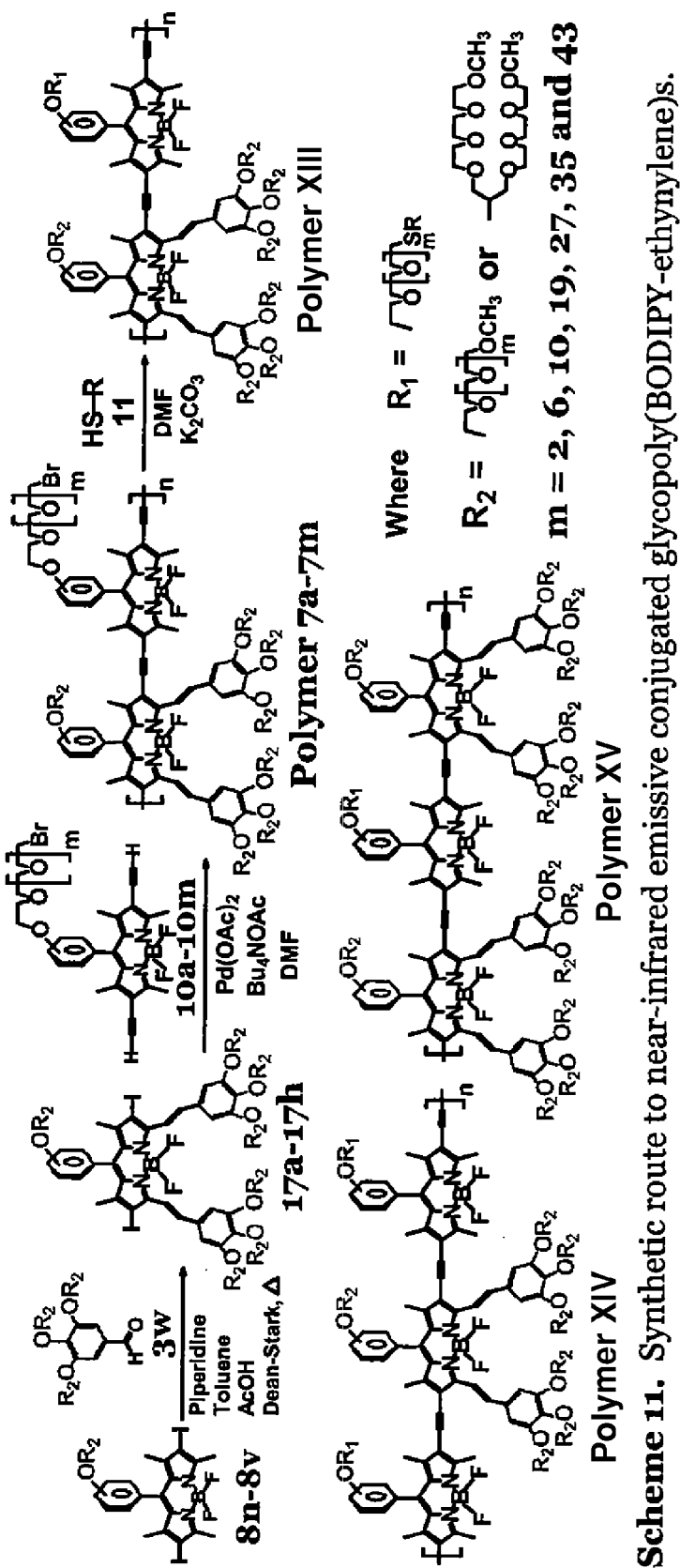
FIG. 23 shows a synthetic route to BODIPY dyes.

In order to further tune fluorescence of glycopoly(BODIPY-ethynylene)s with near-infrared emission, π-conjugation of BODIPY monomers is extended by condensation reactions of BODIPY monomers (8n-8v) with aldehyde derivative (3w), affording highly water-soluble BODIPY monomers (15a-15h) due to several highly branched oligo (ethylene glycol)monomethyl ether groups (FIG. 23). Highly water-soluble near-infrared emissive conjugated glycopoly (BODIPY-ethynylene)s (polymers XIII) are prepared by palladium-catalyzed Sonogashira polymerization of one of BODIPY monomers (17a-17h) with one of BODIPY monomers (10a-10m) in Table 6 in DMF in the presence of Pd(OAc)$_2$ and tetrabutylammonium acetate, resulting in bromide-bearing polymer 7a-7m, and followed by postpolymerization functionalization of polymer 7a-7m with thiol-functionalized carbohydrate (11) in Table 4 (FIG. 23). A library of the glycopolymers with various carbohydrate density and orientation (Polymers XIV and XV) are prepared by polymerizing one or two (1.0 equivalent) of BODIPY monomers (16a-16h) with one or two (1.0 equivalent) of BODIPY monomers (10a-10m) in Table 5 for a series of bromide-bearing poly(BODIPY-ethynylene)s, and followed by functionalization of the bromide-bearing polymers with thiol-functionalized carbohydrates (11) in Table (FIG. 23).

Anticipated Results:

The chemical transformation of the 3,5-methyl groups of 2,5-diiodo-BODIPY dyes (8n-8v) to two vinylphenyl groups will cause a dramatic bathochromic shift in emission of BODIPY dyes (17a-17h) relative to 2,5-diiodo-BODIPY dyes which emit around 548 nm. The enhanced delocalization imparted by a more conjugated and planar vinyl system will reduce the energy required to reach the excited state. As a result, the conjugated glycopoly(BODIPY-ethynylene)s (Polymer XIII-XV) will have significant bathochromic shift and emit in near-infrared region. The polymerization time may need to be prolonged due to the bulky monomers 16a-16h. In addition, water-solubility of glycopoly(BODIPY-ethynylene)s will be further enhanced by strong hydrophilic feature of monomers 17a-17h which will have more than six (up to twenty) hydrophilic groups of oligo(ethylene glycol)monomethyl ether (FIG. 23 and Table 6).

Example 11

Synthesis of BODIPY-Based Near-Infrared Emissive Glyco-Copolymers

Figure 24:
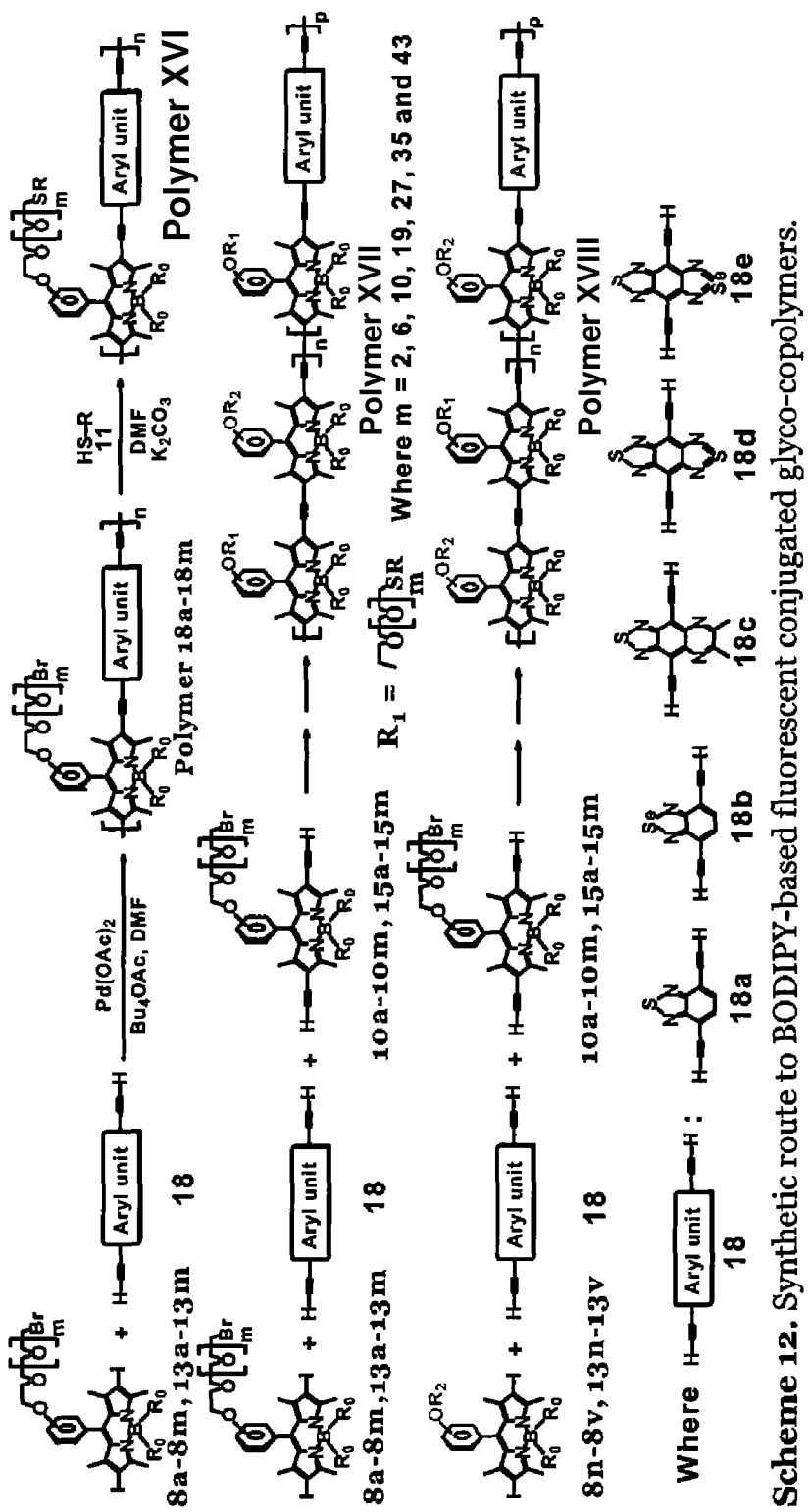
FIG. 24 shows a synthetic route to BODIPY dyes.

Glycopoly(BODIPY-ethynylene)s (polymers V-IX) will emit in deep-red region with emission spectra maxima at 680 nm according to our preliminary results. Narrow-band-gap monomer units are incorporated such as benzo[c][1,2,5]thiadiazole, 2,1,3-benzoselenadiazole, 6,7-dimethyl[1,2,s]thiadiazolo[3,4-g]quinoxaline and benzo[1,2-C:4,5-c']bis([1,2,5]thiadiazole) to backbones of poly(BODIPY-ethynylene)s to tune the polymer fluorescence with near-infrared emission ranging from 700 nm to 900 nm (FIG. 24). Bromide-bearing conjugated BODIPY-based copolymers (polymers 8a-8m) are synthesized by palladium-catalyzed Sonogashira polymerization of one of 2,6-diiodo F-, C- or E-BODIPY monomers (8a-8m, 13a-13m) with one of narrow-band-gap monomers (18a-18e) in DMF solution in the presence of Pd(OAc)$_2$ and tetrabutylammonium acetate (FIG. 21). Well-defined F-, C- or E-BODIPY-based near-infrared emissive copolymers (polymers XVII) bearing different carbohydrate residues are prepared by post-polymerization functionalization of bromide-bearing polymers 8a-8m with a little excess of thiol-functionalized carbohydrate (11) in DMF in a mild basic condition (K$_2$CO$_3$) through 100% thioether formation (Table 5). BODIPY-based glyco-copolymers with different amount of narrow-band-gap monomer units (polymer XVII) are prepared by polymerizing one (1.0 equivalent) of monomers (8a-8m, 13a-13m) with 1:0 equivalent of one of narrow-band-gap monomers (18a-18e) and one of monomer (10a-10, 15a-15m) according to the approach for polymer XVI (FIG. 24). BODIPY-based glyco-copolymers with less density of carbohydrate residues (polymer XVIII) are prepared by polymerizing one (1.0 equivalent) of monomers (8v-8v, 13n-13v) with 1.0 equivalent of one of narrow-band-gap monomers (18a-18e) and one of monomer (10a-10m, 15a-15m) according to the approach for polymer XVI (FIG. 24).

Anticipated results: Incorporation of small amount of narrow-band-gap monomers (from 5% to 50%) will efficiently tune fluorescence of poly(BODIPY-ethynylene)s to near-infrared emission at more than 700 nm due to very effective photoinduced energy transfer along π-conjugated polymer backbones. The amount of narrow-band-gap monomers will need to be optimized to have highly water-soluble BODIPY-based conjugated glycopolymers with near-infrared emission.

Example 12

Synthesis of Fluorescent Conjugated Glycopolymers A-E

Figure 25:
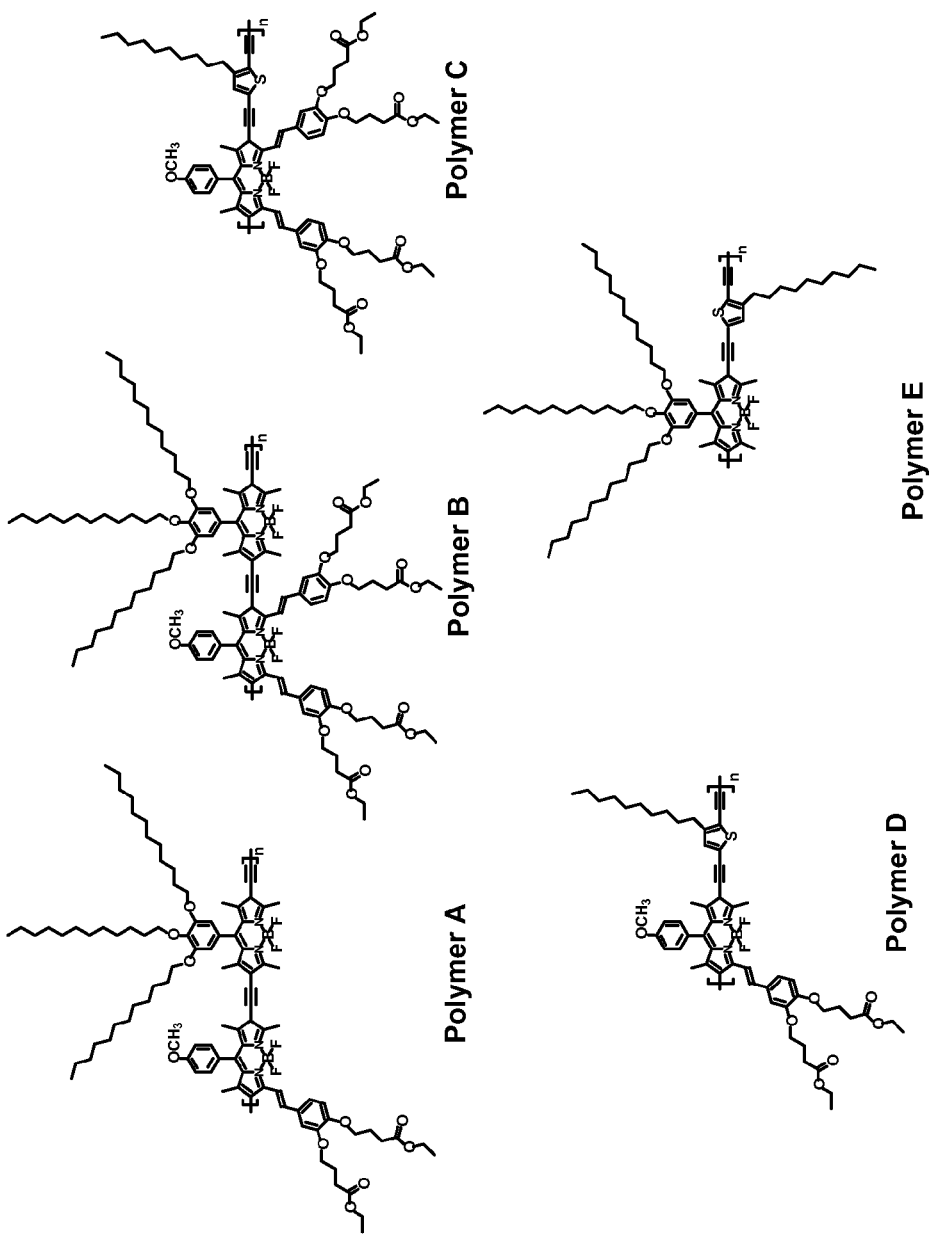
FIG. 25 shows chemical structures of BODIPY polymeric and copolymeric dyes.

Polymers A-E are shown in FIG. 25.

Instrumentation.

$^1$H NMR and $^{13}$C NMR spectra were taken on a 400 MHz Varian Unity Inova spectrophotometer instrument. $^1$H and $^{13}$C NMR spectra were recorded in CDCl$_3$, and chemical shifts (δ) are given in ppm relative to solvent peaks (at −7.24 ppm for $^1$H spectra and at 77.3 for $^{13}$C spectra) as internal standard. UV spectra were taken on a Hewlett-Packard 8452A Diode Array UV-visible spectrophotometer. Fluorescence spectra were recorded on a Spex Fluorolog 1681 0.22 m steady-state fluorometer. Fluorescence quantum yields of BODIPY dyes and polymers were measured in methylene chloride and calculated by using fluorescein excited at 490 nm in 0.1 N NaOH as the reference (its quantum efficiency of 85%). Fluorescence lifetimes were measured on a GL-3300 Nitrogen Laser laserstrobe PTI instrument and analyzed using FeliX32 software.

Materials.

Unless otherwise indicated, all reagents and solvents were obtained from commercial suppliers (Aldrich, Sigma, Fluka, Acros Organics, Fisher Scientific, Lancaster) and were used without further purification. Air- and moisture-sensitive reactions were conducted in oven-dried glassware using a standard Schlenk line or drybox techniques under an inert atmosphere of dry nitrogen. 4,4-Difluoro-8-(4-methoxyphenyl)-1,3,5,7-tetramethyl-4-bora-3a,4a-diaza-s-indacene (2) and 1,4-diethynyl-2,5-didecyloxybenzene (7) were prepared according to the reported procedure.

BODIPY Dyes 4 and 5

Figure 26:
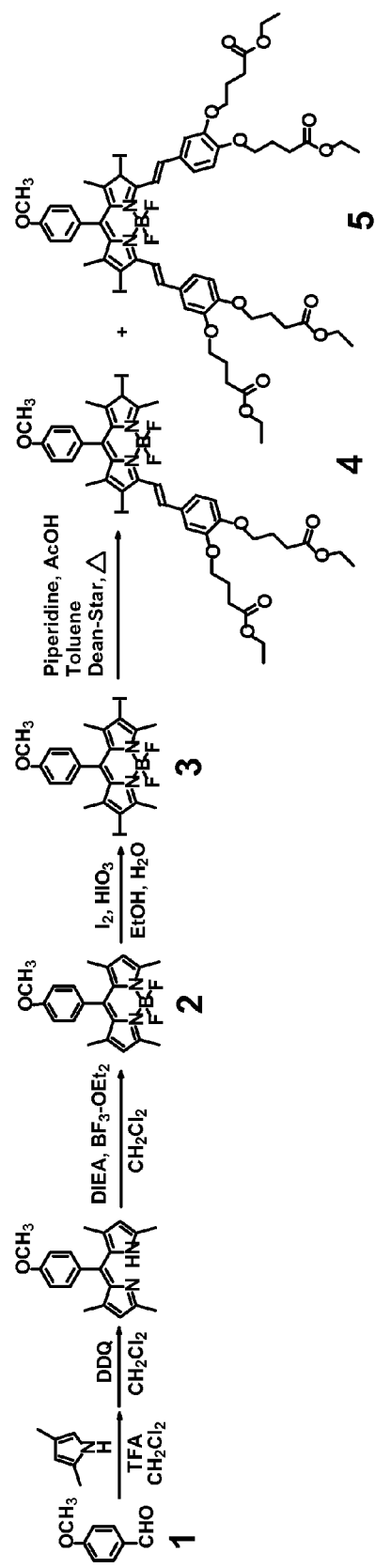
FIG. 26 shows a synthetic route to BODIPY dyes.

The synthetic scheme to the BODIPY dyes 4 and 5 is shown in FIG. 26 and detailed below.

4,4-Difluoro-8-(4-methoxyphenyl)-2,6-diiodo-1,3,5,7-tetramethyl-4-bora-3a,4a-diaza-s-indacene (3)

When iodic acid (11.26 mmol, 1.98 g) in 4 mL of water was added dropwise to the ethanol solution (50 mL) containing BODIPY dye (2) (5.63 mmol 2.0 g) and iodine (6.19 mmol 1.57 g) over 30 min, the mixture was stirred for 3 h. The mixture was concentrated under reduced pressure, dissolved in CH$_2$Cl$_2$, and washed twice with water and saturated sodium chloride solution. The organic layer was collected, dried over anhydrous Na$_2$SO$_4$, and concentrated under reduced pressure. The crude product was purified according to a reported procedure to yield compound 3 as red crystals (3.2 g, 94%).

2,6-diiodo-BODIPY Dye bearing monostyryl and distyryl groups (4, 5): Piperidine (2.88 mL) and acetic acid (2.44 mL) were added to the solution of benzene (120 mL) containing 2,6-diiodo BODIPY dye (3) (1.326 mmol, 0.80 g) and compound 3 (5.18 mmol, 1.93 g) in a 250-mL flask. After the mixture was stirred and refluxed by using a Dean Stark trap for 4 hours, it was cooled to room temperature and concentrated under reduced pressure. The crude product was dissolved in ethyl acetate and washed twice with water. The organic phase was collected, dried over Na$_2$SO$_4$, and filtered. After the filtrate was concentrated, the residue was purified by silica gel column chromatography using hexane/EtOAc (5/1 to 3/1, v/v) to afford dark blue solid compound 4 (540 mg, 43%), dark green solid compound 5 (410 mg, 24%). BODIPY Dye bearing monostyryl group (4): $^1$H NMR (400 MHz, CDCl$_3$): δ 8.05 (d, J=16.8 Hz, 1H), 7.49 (d, J=16.8 Hz, 1H), 7.26 (d, J=8.4 Hz, 1H), 7.14 (m, 2H), 7.02 (d, J=8.0 Hz, 2H), 6.88 (d, J=8.0 Hz, 1H), 4.18-4.06 (m, 8H), 3.87 (s, 3H), 2.68 (s, 3H), 2.59-2.53 (m, 4H), 2.18-2.13 (m, 4H), 1.48 (s, 3H), 1.44 (s, 3H), 1.26 (t, J=7.0 Hz, 6H). $^{13}$C NMR (100 MHz, CDCl$_3$): 173.4, 173.3, 160.7, 156.8, 150.5, 149.2, 146.3, 145.2, 140.5, 139.2, 132.8, 132.5, 130.4, 129.9, 129.5, 127.1, 121.9, 117.2, 115.1, 113.9, 113.2, 86.3, 82.6, 68.5, 68.2, 60.6, 55.6, 30.9, 24.9, 24.8, 17.9, 17.4, 16.4, 14.5. IR (cm$^{-1}$): 2924, 1728, 1511, 1468, 1346, 1246, 1164, 1109, 995, 706. ESI-MS: M$^+$ (C$_{41}$H$_{48}$BF$_2$I$_2$N$_2$O$_7$) Calcd: m/z=983.0. Found: m/z=980.3. The compound shows absorption maximum at 597 nm and emission maximum at 631 nm in CH$_2$Cl$_2$ solution; BODIPY Dye bearing distyryl group (5): $^1$H NMR (400 MHz, CDCl$_3$): δ 8.04 (d, J=16.8 Hz, 2H), 7.51 (d, J=16.4 Hz, 2H), 7.23 (d, J=9.2 Hz, 2H), 7.17 (d, J=8.4 Hz, 2H), 7.10 (s, 2H), 7.01 (d, J=8.4 Hz, 2H), 6.89 (d, J=8.4 Hz, 2H), 4.15-4.05 (m, 16H), 3.85 (s, 3H), 2.55-2.51 (m, 8H), 2.16-2.09 (m, 8H), 1.46 (s, 6H), 1.27-1.20 (m, 12H) ppm. $^{13}$C NMR (100 MHz, CDCl$_3$): δ 173.4, 173.3, 160.7, 150.5, 149.1, 145.9, 139.4, 138.9, 133.6, 130.5, 129.8, 127.4, 121.7, 117.3, 115.0, 114.0, 113.7, 83.3, 68.5, 68.2, 60.6, 60.5, 55.6, 30.9, 24.9, 24.8, 17.9, 14.4 ppm. IR (cm$^{-1}$): 2978, 2933, 1726, 1595, 1509, 1431, 1354, 1244, 1170, 1094, 1010, 770, 708. ESI-MS: M$^+$ (C$_{62}$H$_{76}$BF$_2$I$_2$N$_2$O$_{13}$+Na) Calcd: m/z=1382.0. Found: m/z=1381.8. The compound shows absorption maximum at 665 nm and emission maximum at 701 nm in CH$_2$Cl$_2$ solution.

Polymers A and B

Figure 27:
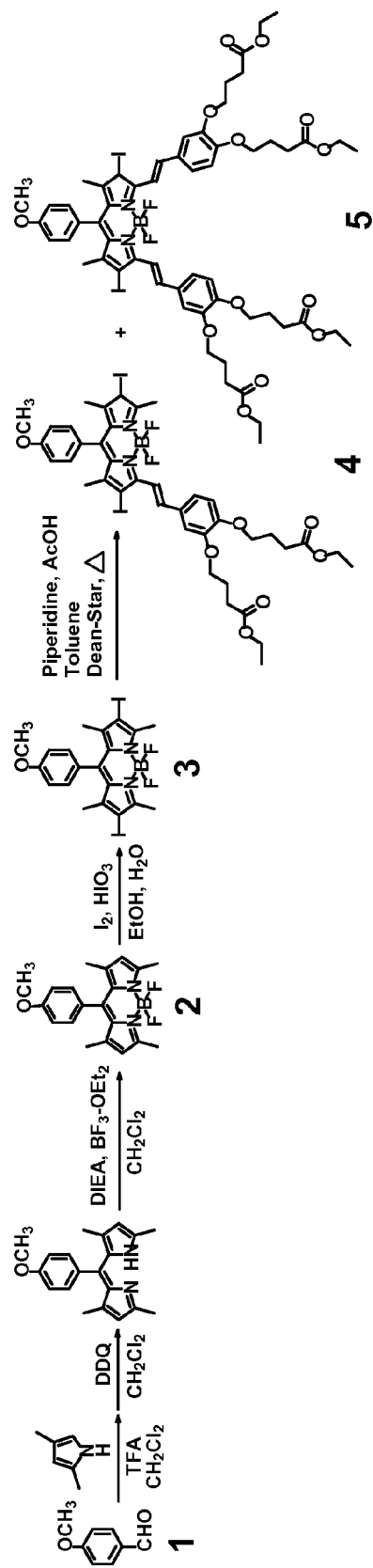
FIG. 27 shows a synthetic route to BODIPY copolymeric dyes.

The synthetic scheme to Polymers A and B is shown in FIG. 27 and detailed below.

Polymer A:

BODIPY dye bearing monostyryl group (4) (0.15 mmol, 150 mg), 2,6-diethynyl BODIPY dye (6) (0.18 mmol, 169 mg), and CuI (3 mg) were added to a 100-mL three-neck flask under a nitrogen atmosphere. Pd(PPh$_3$)$_4$ (6 mg) was added to the flask in a glove box under a nitrogen atmosphere. When degassed anhydrous THF (40 mL) and diisopropylamine (40 mL) were added to the flask under a nitrogen atmosphere, the resulting mixture was stirred under reflux for 24 h. After removal of the solvent, the residue was dissolved in 250 mL of methylene chloride and washed with water three times. After the organic layer was collected, dried over anhydrous MgSO$_4$, and filtered, the filtrate was concentrated under reduced pressure and added to 250 mL of ethanol to precipitate the polymer. The precipitated solid was collected, washed with ethanol and hexane, and dried under vacuum for 24 h at room temperature to obtain dark-violet solid (0.202 g). $^1$H NMR (400 MHz, CDCl$_3$): δ 8.19 (br.d, 1H), 7.56 (br.d, 1H), 7.16-7.10 (br.m, 4H), 7.02-7.00 (br. m, 2H), 6.84 (br. d, 1H), 6.42 (br. s, 2H), 4.14-4.06 (br. m, 8H), 3.98 (br.m, 2H), 3.86 (br. m, 7H), 2.68-2.64 (br. m, 9H), 2.57-2.52 (br. m, 4H), 2.18-2.13 (br. m, 4H), 1.76 (br. m, 6H), 1.66 (br. s, 6H), 1.54-1.23 (br. m, 66H), 0.86-0.85 (br. m, 9H). IR (cm$^{-1}$): 2922, 2852, 1734, 1509, 1313, 1228, 1164, 1086, 1000, 759; The compound shows absorption maximum at 697 nm and emission maximum at 715 nm in CH$_2$Cl$_2$ solution.

Polymer B:

2,6-diiodo BODIPY dye bearing distyryl groups (5) (0.11 mmol, 150 mg), 2,6-diethynyl BODIPY dye (6) (0.13 mmol, 122 mg), and CuI (3 mg) were added to a 100-mL three-neck flask under a nitrogen atmosphere. Pd(PPh$_3$)$_4$ (6 mg) was added to the flask in the glove box under a nitrogen atmosphere. After degassed anhydrous THF (40 mL) and diisopropylamine (40 mL) were added to the flask under a nitrogen atmosphere, the mixture was stirred under reflux for 24 h. Polymer B was purified by using the procedure for polymer A to obtain dark-violet solid (0.182 g). $^1$H NMR (400 MHz, CDCl$_3$): δ 8.20 (br.d, 2H), 7.63 (br.d, 2H), 7.16-7.10 (br. m, 4H), 7.03 (br. s, 2H), 7.02 (br. d, 2H), 6.88 (br. d, 2H), 6.43 (br. s, 2H), 4.15-4.08 (br.m, 16H), 3.99 (br. m, 2H), 3.87 (br. m, 7H), 2.66 (br. s, 6H), 2.57-2.52 (br.m, 8H), 2.18-2.14 (m, 8H), 1.76 (br. m, 6H), 1.66 (br. s, 12H), 1.56-1.23 (br. m, 66H), 0.86-0.85 (br.m, 9H) ppm. $^{13}$C NMR (100 MHz, CDCl$_3$): δ 173.4, 173.3, 160.7, 154.5, 152.3, 150.7, 149.2, 144.6, 143.4, 139.1, 133.5, 131.5, 130.4, 125.2, 122.1, 117.4, 114.9, 113.9, 113.2, 106.3, 94.6, 91.5, 74.0, 69.8, 68.6, 68.2, 60.6, 60.5, 55.5, 32.1, 31.8, 30.9, 30.5, 29.9, 29.8, 29.5, 26.4, 26.2, 24.9, 24.8, 23.6, 22.9, 14.4, 14.3 ppm. IR (cm$^{-1}$): 2921, 2852, 1733, 1506, 1313, 1238, 1179, 1082, 1004, 758, 709; The compound shows absorption maximum at 738 nm and emission maximum at 760 nm in CH$_2$Cl$_2$ solution.

Polymers C and D

Figure 28:
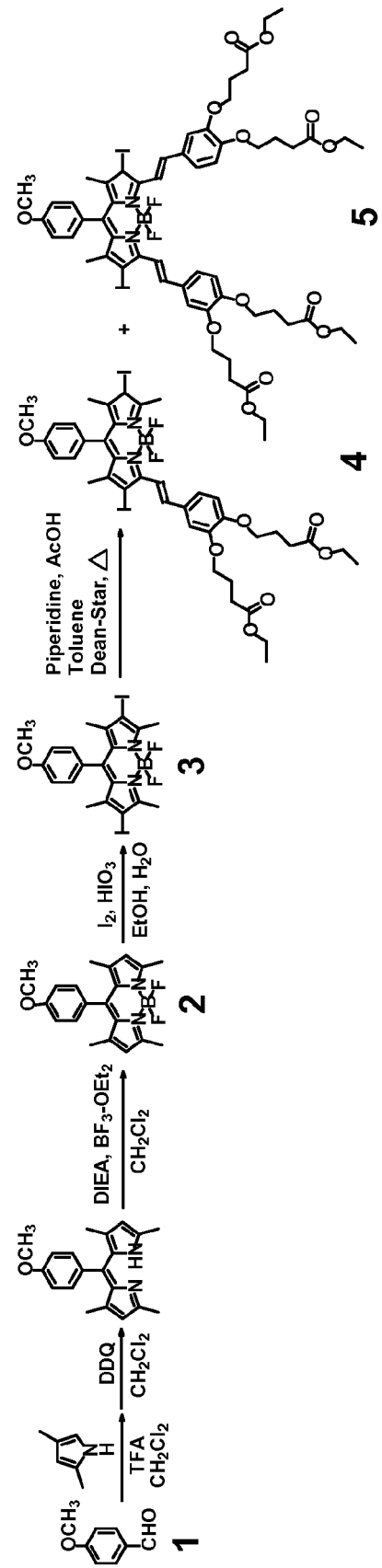
FIG. 28 shows a synthetic route to BODIPY copolymeric dyes.

The synthetic route to Polymers C and D is shown in FIG. 28 and detailed below.

Compound 8.

2,5-diiodo-3-decylthiophene (7) (4.20 mmol, 2 g), CuI (4 mg), and Pd(PPh$_3$)$_2$Cl$_2$ (10 mg) were added to a 100-mL three-neck flask under a nitrogen atmosphere. After degassed anhydrous THF (20 mL), diisopropylamine (20 mL), and trimethylsilylacetylene (12.6 mmol, 1.2 g) were added to the flask under a nitrogen atmosphere, the mixture was stirred at room temperature for 12 h. The mixture was concentrated, dissolved in 50 mL of CH$_2$Cl$_2$ and washed twice with water and saturated saline solution. When the organic layer was collected, dried over anhydrous MgSO$_4$, and filtered, the filtrate was concentrated under reduced pressure. The product was purified by silica gel column chromatography using hexane/EtOAc (98/2 v/v) to yield thick liquid (1.46 g, 84%). $^1$H NMR (400 MHz, CDCl$_3$): δ6.94 (s, 1H), 2.59 (t, J=7.6 Hz, 2H), 1.56 (t, J=6.8 Hz, 2H), 1.31-1.26 (m, 14H), 0.87 (t, J=6.8 Hz, 3H), 0.19 (s, 18H) ppm. $^{13}$C NMR (100 MHz, CDCl$_3$): δ 148.6, 133.6, 122.9, 120.1, 101.9, 99.6, 97.6, 97.1, 32.1, 30.1, 29.8, 29.7, 29.5, 29.3, 22.9, 14.3, 0.09 ppm.

2,5-diethynyl-3-decylthiophene (9)

When tetrabutylamine fluoride (5.63 mmol 2.0 g) was added to the degassed solution of compound 8 (12.1 mmol, 0.50 g) in dry THF (50 mL) at −70° C. through syringe, the resulting mixture was stirred at room temperature for two hours. After the reaction was quenched with dilute acetic acid and 50 mL of dichloromethane was added to the flask, the mixture was washed twice with water and saturated saline solution. When the organic layer was collected, died over anhydrous MgSO$_4$, and filtered, the filtrate was concentrated. The residue was purified by column chromatography using hexane/EtOAc (95/5 v/v) to yield yellow liquid (0.28 g, 87%). The compound was immediately stored at 4° C. $^1$H NMR (400 MHz, CDCl$_3$): δ 7.00 (s, 1H), 3.42 (d, J=1.2 Hz, 1H), 3.30 (d, J=0.8 Hz, 1H), 2.63 (t, J=7.0 Hz, 2H), 1.58 (t, J=7.0 Hz, 2H), 1.31-1.27 (m, 14H), 0.89 (t, J=6.4 Hz, 3H) ppm. $^{13}$C NMR (100 MHz, CDCl$_3$): δ 148.8, 133.9, 122.3, 119.1, 84.2, 81.9, 76.9, 76.2, 32.2, 30.2, 29.9, 29.8, 29.6, 29.5, 29.4, 22.9, 14.4 ppm.

Polymer C.

2,5-Diiodo BODIPY dye bearing distyryl groups (5) (0.11 mmol, 150 mg), 2,5-diethynyl-3-decylthiophene (9) (0.14 mmol, 36 mg), and CuI (3 mg) were added to a 100-mL three-neck flask under a nitrogen atmosphere. Pd(PPh$_3$)$_4$ (6 mg) was added to the flask in the glove box under a nitrogen atmosphere. When degassed anhydrous THF (40 mL) and diisopropylamine (40 mL) were added to the flask under a nitrogen atmosphere, the mixture was stirred under reflux for 24 h. The mixture was concentrated and added dropwise to 250 mL of ethanol under stirring to precipitate the polymer. The precipitated polymer was collected, washed with water, ethanol, acetone and hexane and dried under vacuum for 24 h at room temperature to afford dark-violet solid (0.113 g). $^1$H NMR (400 MHz, CDCl$_3$): δ 8.22 (br. d, 2H), 7.65 (br. d, 2H), 7.16-7.10 (br. m, 4H), 7.05 (br. s, 2H), 7.02 (br. m, 3H), 6.89 (br. d, 2H), 4.15-4.08 (br. m, 16H), 3.87 (br. s, 3H), 2.67-2.63 (br. m, 10H), 2.16-2.09 (br.m, 8H), 1.58 (br.t, 2H), 1.46 (br.s, 6H), 1.30-1.20 (br. m, 26H), 0.87 (br. t, 3H) ppm. IR (cm$^{-1}$): 2921, 2852, 1732, 1509, 1457, 1262, 1249, 1175, 1135, 1044, 958, 750, 723; The compound shows absorption maximum at 713 nm and emission maximum at 758 nm in CH$_2$Cl$_2$ solution.

Polymer D.

2,5-Diiodo BODIPY dye bearing monostyryl group (4) (0.10 mmol, 100 mg), diethynyl-3-decylthiophene (9) (0.12 mmol, 34 mg), and CuI (3 mg) were added to a 100-mL three-neck flask under a nitrogen atmosphere. Pd(PPh$_3$)$_4$ (6 mg) was added to the flask in the glove box under a nitrogen atmosphere. When degassed anhydrous THF (40 mL) and anhydrous diisopropylamine (40 mL) were added to the flask under a nitrogen atmosphere, the mixture was stirred under reflux for 24 h. The polymer D was purified by using the same procedure for polymer C to afford dark-violet solid (0.082 g). $^1$H NMR (400 MHz, CDCl$_3$): δ 8.17 (br.d, 1H), 7.54 (br.d, 1H), 7.15-7.08 (br.m, 4H), 7.02-6.98 (br.m, 3H), 6.82 (br.d, 1H), 4.12-4.03 (br.m, 8H), 3.87 (br.s, 3H), 2.67-2.63 (br.m, 5H), 2.58-2.51 (br.m, 4H), 2.16-2.13 (br.m, 4H), 1.58 (br.t, 2H), 1.48-1.24 (br.m, 26H), 0.88 (br.t, 3H) ppm. IR (cm$^{-1}$): 2921, 2851, 1732, 1509, 1403, 1247, 1178, 1022, 1007, 835; The compound shows absorption maximum at 649 nm and emission maximum at 694 nm in CH$_2$Cl$_2$ solution.

Polymer E

Figure 29:
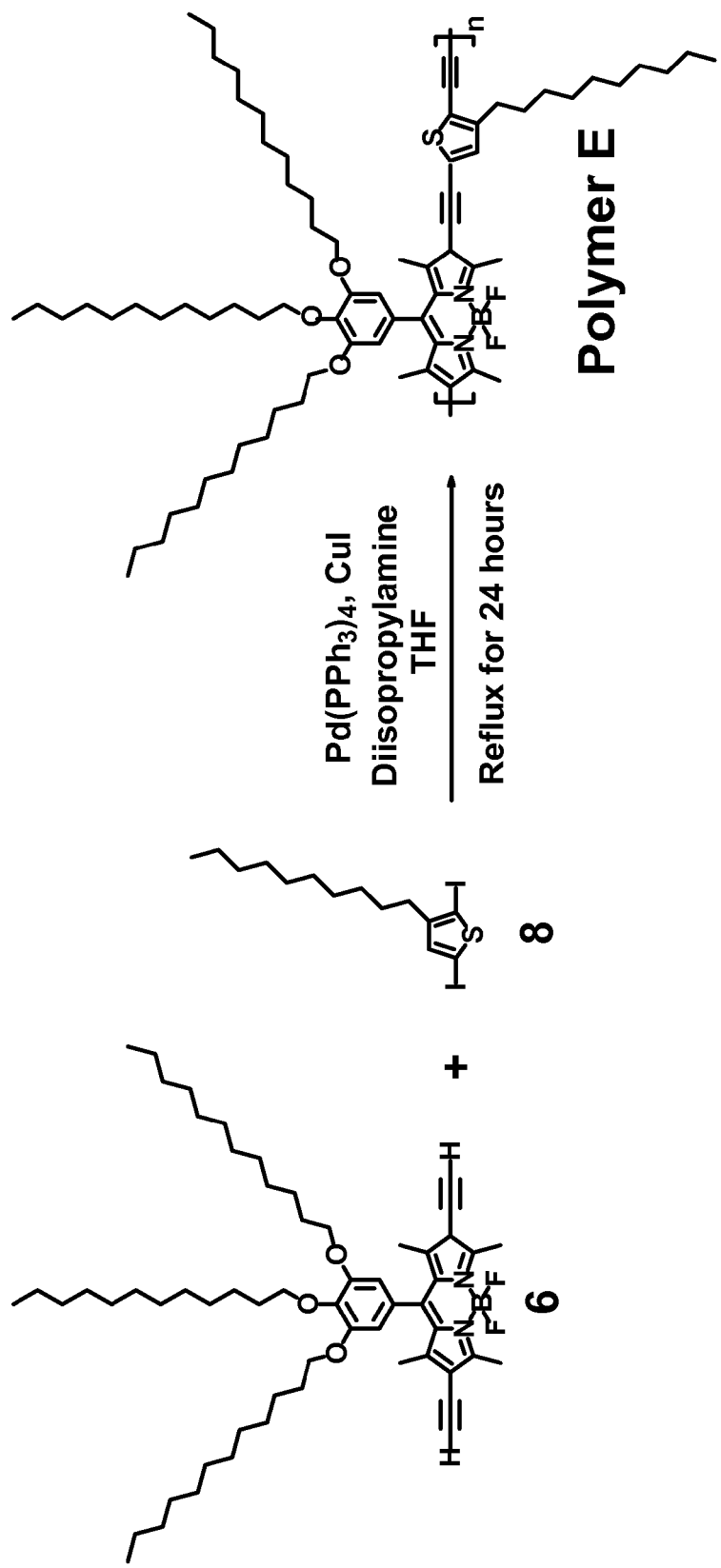
FIG. 29 shows a synthetic route to BODIPY copolymeric dyes.

The synthetic route to Polymer E is shown in FIG. 29 and detailed below.

Polymer E.

2,6-diethynyl-BODIPY dye (6) (0.14 mmol, 150 mg), 2,5-diiodo-3-decylthiophene (8) (0.12 mmol, 60 mg), and CuI (3 mg) were added to a 100-mL three-neck flask under a nitrogen atmosphere. Pd(PPh$_3$)$_4$ (6 mg) was added to the flask in the glovebox under a nitrogen atmosphere. Anhydrous THF (40 mL) and diisopropylamine (40 mL) were added to the flask in a nitrogen atmosphere. When the mixture was stirred under reflux for 24 h, the mixture was added dropwise to 500 mL of ethanol to precipitate the polymer. The precipitated polymer was collected, washed with water, ethanol, acetone and hexane and dried under vacuum for 24 h at room temperature to obtain dark-violet solid (0.132 g). $^1$H NMR (400 MHz, CDCl$_3$): δ6.95 (br.s, 1H), 6.45 (br. s, 2H), 4.02 (br. s, 2H), 3.91 (br. s, 4H), 2.67 (br. s, 6H), 1.77 (br. t, 4H), 1.64 (br.s, 6H), 1.49-1.44 (br. m, 6H), 1.24 (br. m, 72H), 0.85 (br. t, 12H) ppm. $^{13}$C NMR (100 MHz, CDCl$_3$): δ 158.7, 154.6, 147.5, 143.2, 142.5, 139.2, 132.4, 131.5, 115.8, 106.3, 90.2, 88.8, 73.9, 69.7, 32.2, 32.1, 30.5, 30.3, 29.9, 29.8, 29.6, 29.5, 26.3, 26.2, 22, 9, 14.3, 13.9, 13.5 ppm. IR (cm$^{-1}$): 2921, 2852, 1525, 1315, 1229, 1111, 1004, 759, 720. The compound shows absorption maximum at 634 nm and emission maximum at 669 nm in CH$_2$Cl$_2$ solution.

Optical Properties of BODIPY Polymeric and Copolymeric Dyes.

Figure 30:
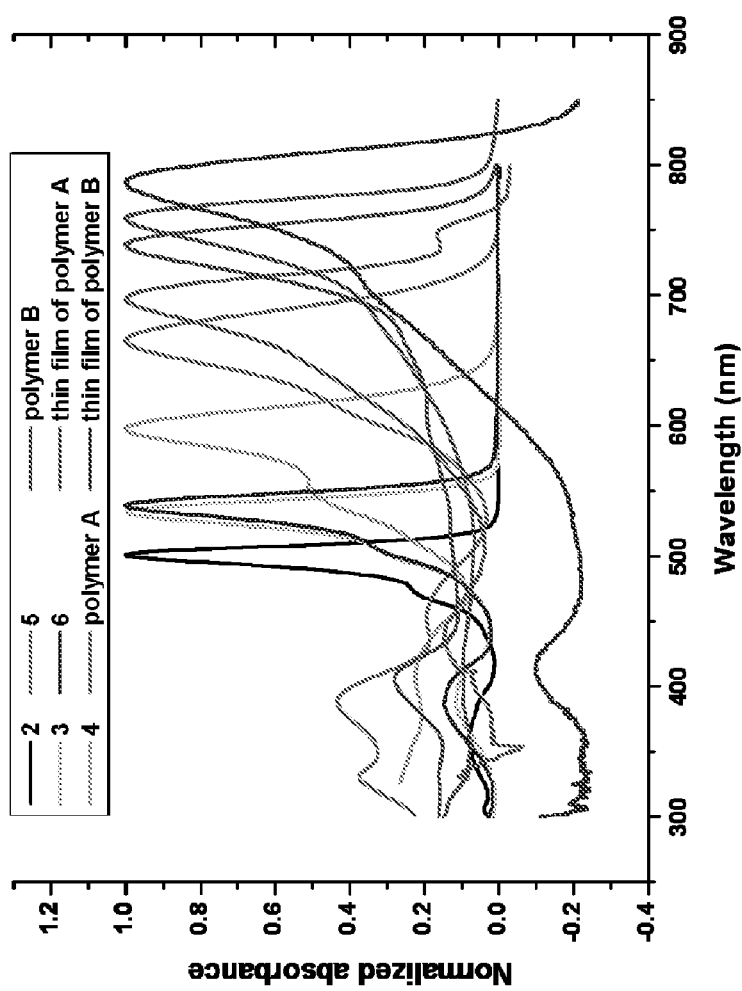
FIG. 30 shows absorption spectra of BODIPY dyes and polymeric dyes.
Figure 31:
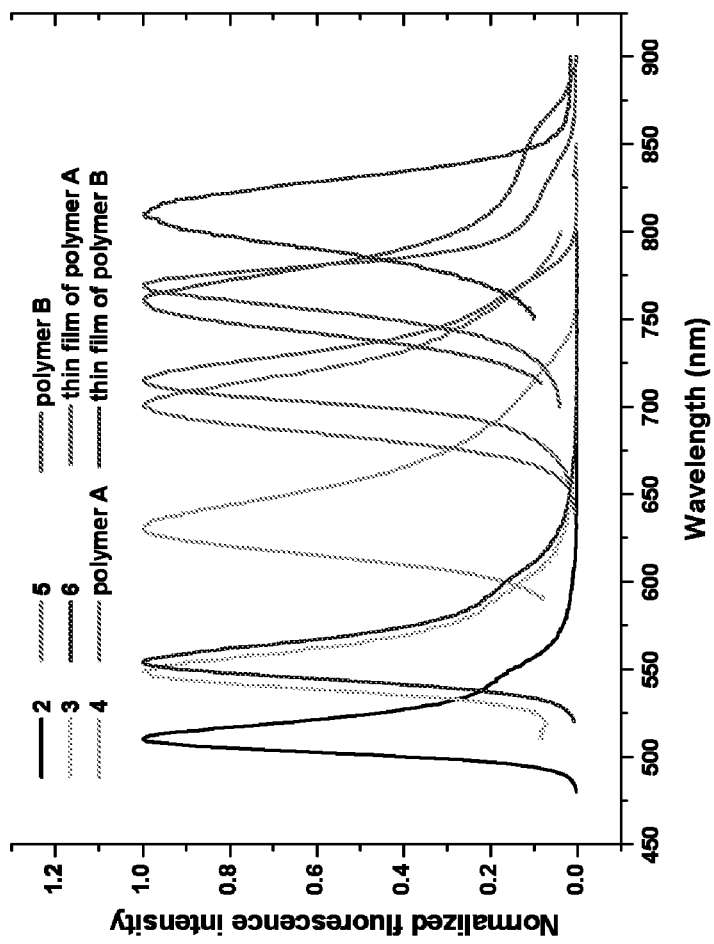
FIG. 31 shows fluorescence spectra of BODIPY dyes and polymeric dyes.

The photophysical characteristics of BODIPY intermediate, monomeric and polymeric dyes were investigated in methylene chloride. The absorption properties of the BODIPY dye 2 in methylene chloride solution are characterized by a strong S$_0$→S$_1$ (π-π*) transition at 502 nm and a weaker broad band at a shorter wavelength around 356 nm due to the S$_0$→S$_2$ (π-π*) transition (FIG. 30). The introduction of diiodo substituent to the dipyrromethene core (2) results in a significant red shift (up to 33 nm and 38 nm) of both the UV-absorption and fluorescent maxima, respectively (FIGS. 30 and 31), and significantly quenches the fluorescence quantum yield because of the heavy atom effect (Table 7). Absorption and fluorescence spectra of 2,6-diiodo-substituted BODIPY dye 2 exhibit good mirror symmetry with similar band shapes for the absorption and emission spectra which was also verified by measuring their full width at half-maximum (FIGS. 30 and 31). Further condensation of 2,6-diiodo BODIPY dye bearing methyl substituents at 3 and 5 positions (3) with aldehyde derivative gave longer wavelength absorbing BODIPY dyes bearing alkoxymonostyryl and alkoxydistyryl (4,5). The extended π-conjugation in these dyes results in significant red shifts in both absorption and emission spectra compared with their precursor BODIPY dye (3). Alkoxymonostyryl-bearing BODIPY dye (4) shows absorption and emission maxima at 579 nm and 631 nm with red shifts of 79 nm and 121 nm in absorption and emission spectra, respectively, compared with its starting BODIPY dye (2). Alkoxydistyryl-bearing BODIPY dye (5) displays red shifts of 165 nm and 170 nm in absorption and emission spectra with absorption and emission maxima of 665 nm and 701 nm, respectively, compared with its starting BODIPY dye (2) (Table 7). Both alkoxymonostyryl- and alkoxydistyryl-substituted BODIPY dyes (4,5) exhibit low fluorescence quantum yields because of heavy atom effect. Palladium-catalyzed Sonogashira polymerization of alkoxymonostyryl- and alkoxydistyryl-substituted BODIPY dyes (4,5) with 2,6-diethynyl-substituted BODIPY (6) resulted in near-infrared emissive BODIPY polymeric dyes (polymers A and B) with the further extended π-conjugation, respectively. Polymer A shows significant red shifts of 100 nm and 84 nm in absorption and emission with absorption and emission maxima of 679 nm and 715 nm, respectively, compared with its alkoxymonostyryl-substituted BODIPY monomeric dye (4). Polymer B display absorption and emission maxima at 738 nm and 760 nm with significant red shifts of 73 nm and 59 nm in absorption and emission with, respectively, compared with its alkoxydistyryl-substituted BODIPY monomeric dye (5) (FIGS. 30 and 31).

Figure 32:
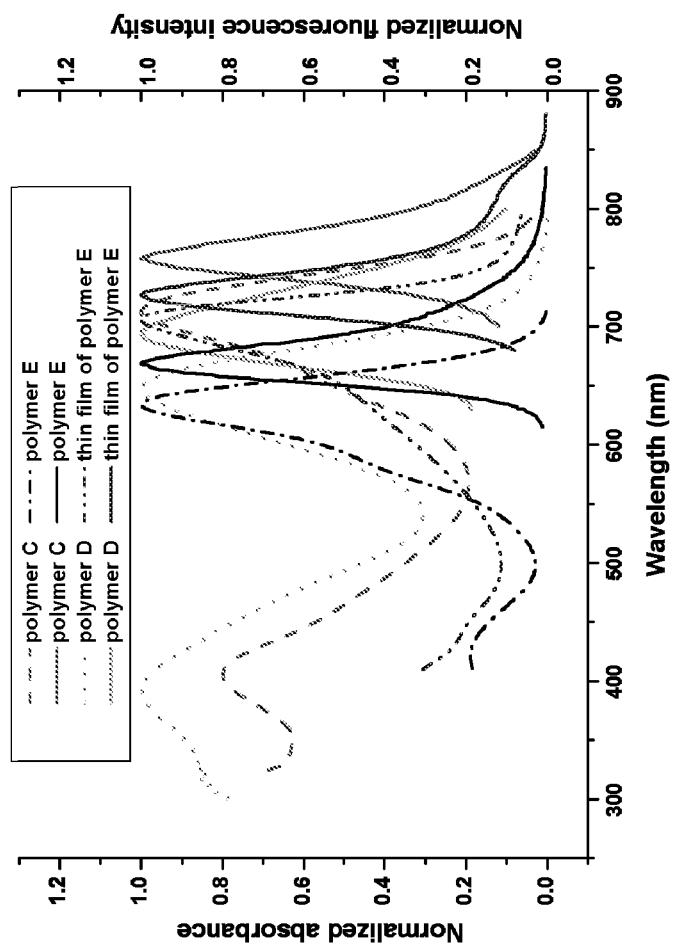
FIG. 32 shows absorption and fluorescence spectra of BODIPY copolymeric dyes.

Palladium-catalyzed Sonogashira polymerization of alkoxydistyryl- and alkoxymonostyryl-substituted BODIPY dyes (5,4) with 2,5-diethynyl-3-decylthiophene (10) resulted in near-infrared and deep-red emissive BODIPY copolymeric dyes with emission maxima of 758 nm and 694 nm (polymers C and D), respectively (FIG. 32). Palladium-catalyzed Sonogashira polymerization of 2,6-diethynyl-substituted BODIPY dyes (6) with 2,5-diiodo-3-decylthiophene (8) resulted in red emissive BODIPY copolymeric dye with emission maxima of 634 nm and 669 nm (polymers E), respectively. All BODIPY copolymeric dyes display low fluorescence quantum yields because of heavy sulfur atom effect (Table 7).

Solid-state absorption and emission spectra were collected to evaluate effect of the polymer aggregation on their optical properties as the absorption and emission spectra of the film reflect polymer π-π stacking effects. The solid state film was prepared by spin-casting methylene chloride solutions of the polymers onto quartz discs. The absorption spectra of the polymers in thin films became a little broader, and maximum peaks were obviously red-shifted compared with those in methylene chloride solutions. The fluorescence spectra of the polymers in solid state thin films retain most of the spectra features in solution and exhibit further red shifts with their absorption and emission maxima in near-infrared region compared with those in methylene chloride solution, indicating the presence of intermolecular electronic interaction and/or increase in coplanarity of the polymer in the solid state (Table 8).

Example 13

Synthesis of Fluorescent Conjugated Glycopolymers A-C

Figure 34:
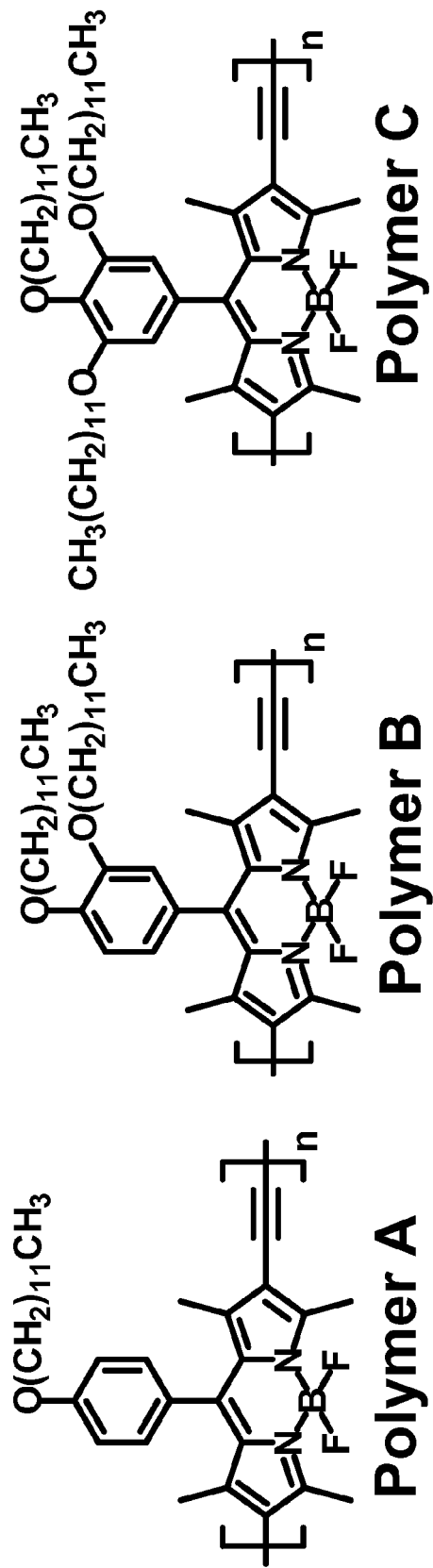
FIG. 34 shows chemical structures of conjugated polymers with BODIPY backbone.

The structures of Polymers A-C are shown in FIG. 34.

Experimental Section

Instrumentation.

$^1$H NMR and $^{13}$C NMR spectra were taken on a 400 MHz Varian Unity (nova spectrophotometer instrument. $^1$H and $^{13}$C NMR spectra were recorded in $CDCl_3$, chemical shifts (δ) are given in ppm relative to solvent peaks ($^1$H: δ 7.26; $^{13}$C: δ 77.3) as internal standard. UV spectra were taken on a Hewlett Packard 8452A Diode Array UV-visible spectrophotometer. Fluorescence spectra were recorded on a Spex Fluorolog 1681 0.22 m steady-state fluorometer. Fluorescence quantum yields of BODIPY dyes and polymers were measured in methylene chloride and DMF, and calculated by using fluorescein excited at 490 nm in 0.1°N NaOH as the reference quantum efficiency ($\phi_n$=85%).[30, 31] Molecular weights of the polymers were determined by gel permeation chromatography (GPC) by using a Waters Associates Model 6000A liquid chromatograph. Three American Polymer Stan-

TABLE 7

Absorption and emission maxima, fluorescence quantum yields and lifetimes of BODIPY dyes and polymeric dyes in methylene chloride solution

| | BODIPY dyes or polymers | | | | | | | | | |
|---|---|---|---|---|---|---|---|---|---|---|
| | 2 | 3 | 4 | 5 | 6 | A | B | C | D | E |
| absorption maxima (nm) | 500 | 533 | 597 | 665 | 539 | 697 | 738 | 713 | 649 | 634 |
| emission maxima (nm) | 510 | 548 | 631 | 701 | 554 | 715 | 760 | 758 | 694 | 669 |
| Quantum yield (%) | 80 | 5.7 | 2.6 | 4 | 52 | 11 | 13 | 1.3 | 1.1 | 1.2 |
| fluorescence lifetime (ns) | 3.8 | 1.7 | 1.75 | 2.32 | 3 | 0.86 | 0.71 | 0.52 | 0.69 | 0.41 |

TABLE 8

Absorption and Emission Maxima of thin films on quartz surface

| BODIPY polymers | Thin film Polymer A | Thin film Polymer B | Thin film Polymer E |
|---|---|---|---|
| absorption maxima (nm) | 759 | 784 | 706 |
| emission maxima (nm) | 769 | 810 | 727 |

Thermal Stabilities of the Polymers.

Figure 33:
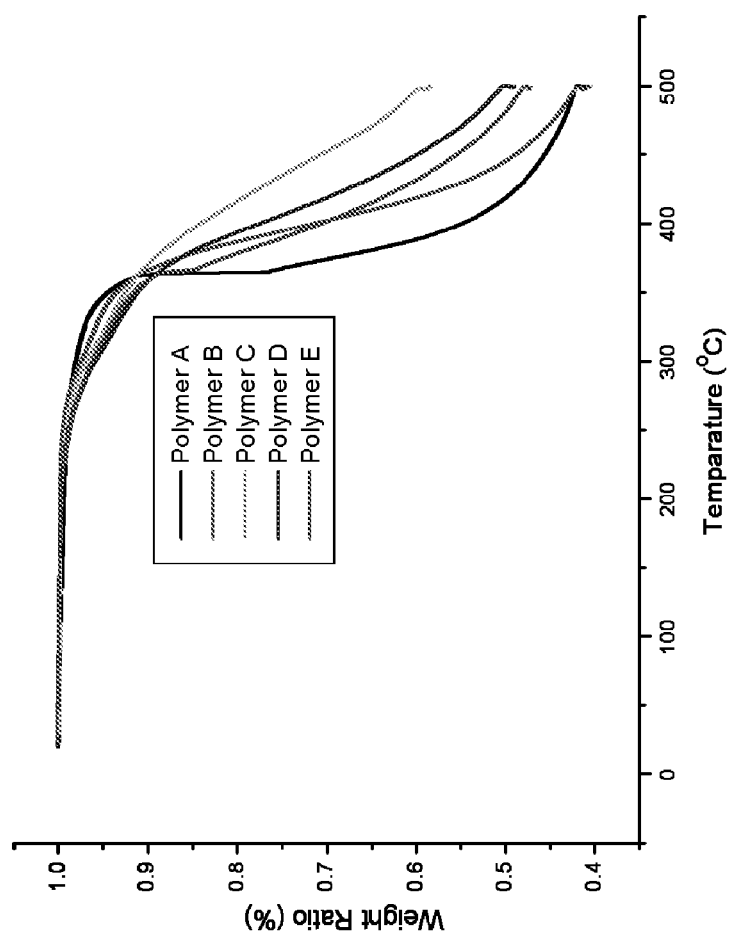
FIG. 33 shows TGA curves for BODIPY based polymers.

Thermal stabilities of BODIPY polymeric and copolymeric dyes were evaluated by thermogravimetrc analysis (TGA) at the heating rate of 20° C./min under nitrogen atmosphere. The thermograms show that polymers A, B and C lost 5% of their weight at 250° C. (the decomposition temperature ($T_d$) that corresponds to weight loss of 5%), respectively, which suggests their good thermal stability (FIG. 33). Differential scanning calorimetry (DSC) of polymers did not give a clear phase, may be because of rigid backbone of the BODIPY.

dards Corp. Ultrastyragel columns in series with porosity indices of $10^3$, $10^4$, and $10^5$ Å were used and housed in an oven thermostated at 30° C. Mobile phase was HPLC grade THF which was filtered and degassed by vacuum filtration through a 0.5 μm fluoropore filter prior to use. The polymers were detected by a Waters Model 440 ultraviolet absorbance detector at a wavelength of 254 nm and a Waters Model 2410 refractive index detector. Molecular weights were measured relative to polystyrene standards.

Materials.

Unless otherwise indicated, all reagents and solvents were obtained from commercial suppliers (Aldrich, Sigma, Fluka, Acros Organics, Fisher Scientific, Lancaster), and were used without further purification. Air- and moisture-sensitive reactions were conducted in oven-dried glassware using standard Schlenk line or dry box techniques under an inert atmosphere of dry nitrogen.

Polymer A

Figure 35:
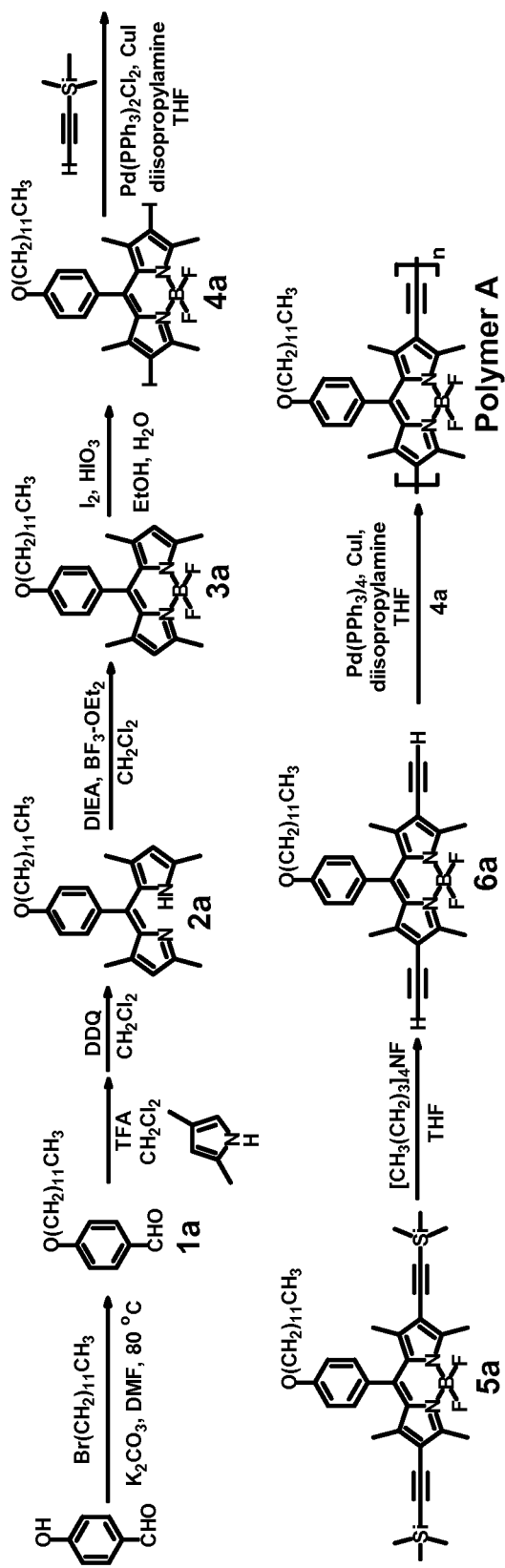
FIG. 35 shows a synthetic route to a BODIPY based polymer.

The synthetic route to Polymer A is shown in FIG. 35 and detailed below.

Compound 1a:

When 150 mL of degassed DMF was added to in a 500 mL three-neck round-bottom flask containing 4-hydroxybezaldehyde (40.9 mmol, 5 g), 1-bromododecane (49.2 mmol, 12.2 g) and $K_2CO_3$ (122 mmol, 16.8 g) under a nitrogen atmosphere, the mixture was stirred for 4 hours at 80° C. under a nitrogen atmosphere. After completion of the reaction (which was monitored by TLC), the reaction mixture was concentrated under reduced pressure, added to water and extracted with EtOAc. The organic layer was washed twice with water and saturated NaCl solution, dried over anhydrous $MgSO_4$ and concentrated under reduced pressure. The resulting crude product was purified by silica gel column chromatography using hexane/EtOAc (80/20, v/v) to obtain brown liquid (11.6 g, 98%). $^1$H NMR (400 MHz, $CDCl_3$) δ 9.86 (s, 1H), 7.81 (d, J=8.8 Hz, 2H), 6.97 (d, J=8.8 Hz, 2H), 4.01 (t, J=6.6 Hz, 2H), 1.81-1.77 (m, 2H), 1.46-1.44 (m, 2H), 1.42-1.25 (m, 16H), 0.86 (t, J=6.8 Hz, 3H); $^{13}$C NMR (100 MHz, $CDCl_3$) δ 191.0, 164.9, 132.2, 130.0, 115.0, 68.6, 32.1, 29.8, 29.7, 29.5, 29.2, 26.1, 22.9, 14.3.

Compound 3a:

1a (17.4 mmol, 5.06 g) and 2,4-dimethylpyrrole (34.9 mmol, 3.32 g) were dissolved in 1200 mL of dry $CH_2Cl_2$ in a 2000-mL three-neck flask. Eight drops of TFA were added to the reaction mixture, and resulting mixture was stirred in dark for 12 hours under nitrogen atmosphere at room temperature. After the complete consumption of aldehyde (1a) (which was conformed by TLC), DDQ (2,3-dichloro-5,6-dicyano-1,4-benzoquinone) (17.4 mmol 3.95 g) in 100 mL of $CH_2Cl_2$ was added to the reaction mixture. When the mixture was stirred for 30 minutes, 35 mL of diisopropylethylamine (DIEA) and 35 mL of $BF_3.OEt_2$ were added to the mixture. After the mixture was further stirred for 30 minutes, it was concentrated to 200 mL and filtered. The filtrate was washed once with sodium bicarbonate solution and twice with water, dried over anhydrous $MgSO_4$ and concentrated under reduced pressure. The crude product was purified by column chromatography using hexane/EtOAc (90/10 to 70/30, v/v) to obtain dark brown crystalline solid (3.15 g, 36%). $^1$H NMR (400 MHz, $CDCl_3$) δ 7.13 (d, J=8.4 Hz, 2H), 6.97 (d, J=8.4 Hz, 2H), 5.95 (s, 2H), 3.99 (t, J=6.6 Hz, 2H), 2.53 (s, 6H), 1.82-1.78 (m, 2H), 1.49-1.42 (m, 8H), 1.36-1.26 (m, 16H), 0.87 (t, J=6.6 Hz, 3H); $^{13}$C NMR (100 MHz, $CDCl_3$) δ 159.9, 155.4, 143.4, 142.2, 132.1, 129.3, 127.0, 121.3, 115.3, 68.4, 32.1, 29.9, 29.8, 29.6, 29.5, 29.4, 26.3, 22.9, 14.8, 14.3. IR ($cm^{-1}$): 2922, 2850, 1540, 1508, 1465, 1408, 1306, 1247, 1182, 1155, 1084, 971, 832, 811, 704. ESI-MS. $M^+$ ($C_{31}H_{43}BF_2N_2O$) Calcd: m/z=508.5. Found: m/z=509.2.

Compound 4a:

When iodic acid (12.3 mmol, 2.18 g) in 5 mL of water was added dropwise to the ethanol solution (50 mL) containing compound 3a (5.9 mmol 3.0 g) and iodine (12.9 mmol 1.65 g) over 30 minutes, the mixture was stirred for 2 hours. After the completion of the reaction, the unreacted iodine was quenched with sodium thiosulphate and the mixture was concentrated under reduced pressure and dissolved in $CH_2Cl_2$, and washed twice with water and saturated saline solution. The organic layer was collected, dried over anhydrous $MgSO_4$ and concentrated under reduced pressure. The crude product was purified by column chromatography to yield 4a as red crystals (4.4 g, 98%). $^1$H NMR (400 MHz, $CDCl_3$) δ 7.10 (d, J=8.8 Hz, 2H), 7.00 (d, J=8.8 Hz, 2H), 4.00 (t, J=6.6 Hz, 2H), 2.62 (s, 6H), 1.84-1.80 (m, 2H), 1.48-1.43 (m, 8H), 1.38-1.26 (m, 16H), 0.87 (t, J=6.6 Hz, 3H); $^{13}$C NMR (100 MHz, $CDCl_3$) δ 160.4, 156.7, 145.6, 142.0, 132.0, 129.2, 126.6, 115.6, 85.8, 68.5, 32.2, 29.9, 29.8, 29.7, 29.6, 29.5, 26.3, 22.9, 17.4, 16.2, 14.4; IR ($cm^{-1}$): 2923, 2853, 1528, 1465, 1398, 1344, 1307, 1248, 1178, 998. $M^+$ ($C_{31}H_{41}BF_2I_2N_2O$) Calcd: m/z=760.3. Found: m/z=760.0.

Compound 5a:

Compound 4a (3.28 mmol, 2.5 g), CuI (0.02 mmol, 0.004 g) and $Pd(PPh_3)_2Cl_2$ (0.02 mmol, 0.015 g) were added to a 250-mL three-neck round-bottom flask under a nitrogen atmosphere. When 20 mL of anhydrous degassed THF, 30 mL of anhydrous diisopropylamine, and trimethylsilylacetylene (8.2 mmol, 0.8 g) were added to the flask, the mixture was stirred under reflux for 12 hours. After the completion of the reaction (which was monitored by TLC), the reaction mixture was concentrated and dissolved in 50 mL of $CH_2Cl_2$, washed twice with water and saturated saline solution. The organic layer was collected, dried over anhydrous $MgSO_4$, and concentrated under reduced pressure. The product was purified by neutralized silica gel column chromatography using hexane/EtOAc (95/5 to 80/20, v/v) to yield orange-red solid (1.86 g, 81%). $^1$H NMR (400 MHz, $CDCl_3$) δ 7.08 (d, J=8.8 Hz, 2H), 6.98 (d, J=8.8 Hz, 2H), 4.00 (t, J=6.6 Hz, 2H), 2.61 (s, 6H), 1.83-1.79 (m, 2H), 1.47-1.46 (m, 8H), 1.36-1.25 (m, 16H), 0.87 (t, J=6.6 Hz, 3H), 0.19 (s, 18H); $^{13}$C NMR (100 MHz, $CDCl_3$) 160.3, 158.7, 145.2, 143.3, 131.7, 129.2, 126.3, 116.2, 115.4, 101.8, 97.4, 68.5, 32.1, 29.9, 29.8, 29.6, 29.5, 29.4, 29.2, 26.3, 22.9, 14.4, 13.8, 0.28. $^{11}$B NMR (400 MHz, $CDCl_3$): 3.82 (t, J=97.6 MHz). IR ($cm^{-1}$): 2922, 2853, 2150, 1608, 1526, 1469, 1393, 1365, 1316, 1247, 1195, 1093, 833, 703. ESI-MS. $M^+$ ($C_{41}H_{59}BF_2N_2OSi_2$) Calcd: m/z=700.9. Found: m/z=700.9.

Compound 6a:

When compound 5a (2.1 mmol, 1.50 g) was dissolved in degassed THF (8 mL) in a 100-mL flask at −70° C., tetrabutylammonium fluoride (TBAF) (5.2 mmol, 1.3 g, 5.2 mL of 1M solution) was added dropwise to the mixture via syringe. The reaction temperature was brought to the room temperature and the mixture was further stirred for 2 hours. After completion of the reaction, the mixture was acidified with acetic acid and extracted with $CH_2Cl_2$. The extracted organic layer washed twice with water and saturated saline solution, dried over anhydrous $MgSO_4$, and concentrated under reduced pressure. The crude product was purified by column chromatography using hexane/EtOAc (20/80, v/v) to give the desired product as orange-pink crystalline solid (0.84 g, 72%). $^1$H NMR (400 MHz, $CDCl_3$) δ 7.11 (d, J=8.8 Hz, 2H), 7.00 (d, J=8.8 Hz, 2H), 4.00 (t, J=6.6 Hz, 2H), 3.3 (s, 2H), 2.63 (s, 6H), 1.83-1.79 (m, 2H), 1.51-1.46 (m, 8H), 1.44-1.26 (m, 16H), 0.87 (t, J=6.6 Hz, 3H); $^{13}$C NMR (100 MHz, $CDCl_3$) δ 160.3, 158.8, 145.8, 143.3, 131.6, 129.2, 126.2, 115.5, 115.2, 84.2, 76.2, 68.5, 32.1, 29.9, 29.8, 29.6, 29.5, 29.4, 26.2, 22.9, 14.3, 13.7; $^{11}$B NMR (400 MHz, $CDCl_3$): 3.82 (t, J=97.6 MHz). IR ($cm^{-1}$): 3299, 2921, 2852, 2105, 1726, 1602, 1532, 1468, 1392, 1313, 1288, 1248, 1161, 1125, 1070, 1007, 833, 800, 708. ESI-MS. $M^+$ ($C_{35}H_{43}BF_2N_2O$) Calcd: m/z=556.5. Found: m/z=557.2.

Polymer A:

Compound 4a (0.133 mmol, 0.100 g), compound 6a (0.144 mmol, 0.080 g), CuI (0.01 mmol, 0.002 g) were added to 100-mL flask under a nitrogen atmosphere. In the glove box, $Pd(PPh_3)_4$ (0.01 mmol, 0.012 g) was added to the flask. When a degassed mixed solution of anhydrous THF (20 mL) and anhydrous diisopropylamine (20 mL) were added to the flask, the mixture was stirred under reflux for 24 hours. After removal of the solvent, the residue was dissolved in methylene chloride (5 mL) added to 400 mL of ethanol and stirred for 2 hrs to precipitate the polymer. The precipitated solid was filtered and washed with excess ethanol and hexane. The obtained solid dried under vacuum for 24 h at room temperature to obtain dark-violet solid (0.150 g). $^1$H NMR (400 MHz, $CDCl_3$) δ 7.09 (br, 2H), 6.99 (br, 2H), 3.99 (br, 2H), 2.62 (s, 6H), 1.82 (br, 2H), 1.66 (br, 6H), 1.51 (br, 4H), 1.26 (br, 14H), 0.87 (br, 3H); $^{13}$C NMR (100 MHz, $CDCl_3$) δ 160.3, 158.8, 145.7, 142.3, 131.7, 129.1, 126.2, 115.5, 113.6, 88.9, 68.5, 32.1, 29.9, 29.8, 29.6, 29.5, 29.4, 26.2, 22.9, 14.3, 13.7; IR (cm$^{-1}$): 3675, 2988, 2972, 2902, 1406, 1394, 1383, 1249, 1242, 1230, 1075, 1066, 1057, 892, 880.

Polymer B

Figure 36:
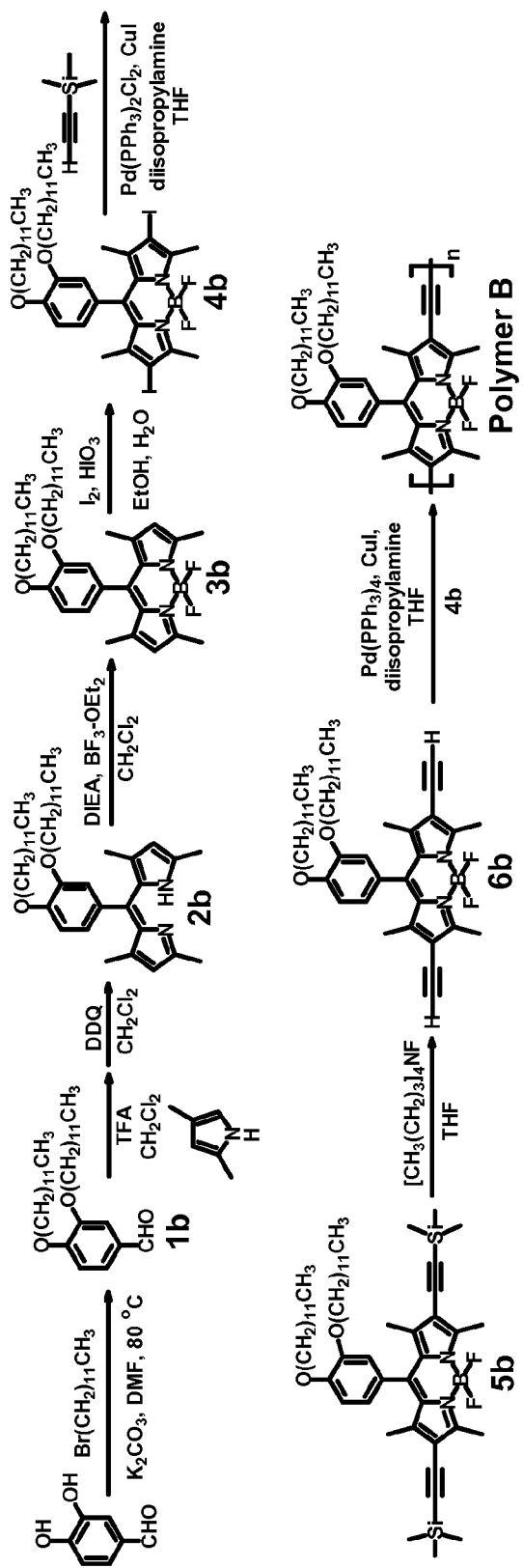
FIG. 36 shows a synthetic route to a BODIPY based polymer.

The synthetic route to Polymer B is shown in FIG. 36 and detailed below.

Compound 1b:

When 150 mL of degassed DMF was added to in a 500 mL three-neck round-bottom flask containing 3,4-dihydroxybezaldehyde (22.3 mmol, 3 g), 1-bromododecane (49.2 mmol, 12.2 g) and K$_2$CO$_3$ (122 mmol, 16.8 g) under a nitrogen atmosphere, the mixture was stirred for 4 hours at 80° C. under a nitrogen atmosphere. After completion of the reaction (which was monitored by TLC), the reaction mixture was concentrated under reduced pressure, added to water and extracted with EtOAc. The organic layer was washed twice with water and saturated NaCl solution, dried over anhydrous MgSO$_4$ and concentrated under reduced pressure. The resulting crude product was purified by silica gel column chromatography using hexane/EtOAc (80/20, v/v) to obtain white solid (10.3 g, 98%). $^1$H NMR (400 MHz, CDCl$_3$) δ 9.81 (s, 1H), 7.41-7.37 (m, 2H), 6.93 (d, J=8.4 Hz, 1H), 4.08-4.02 (m, 4H), 1.86-1.80 (m, 4H), 1.47-1.44 (m, 4H), 1.34-1.24 (m, 32H), 0.86 (t, J=6.8 Hz, 6H); $^{13}$C NMR (100 MHz, CDCl$_3$) δ 191.2, 154.9, 149.7, 130.1, 126.8, 112.0, 111.2, 69.3, 32.1, 29.9, 29.8, 29.7, 29.6, 29.5, 29.3, 29.2, 26.2, 26.1, 22.9, 14.3.

Compound 3b.

1b (17.4 mmol, 8.25 g) and 2,4-dimethylpyrrole (34.88 mmol, 3.32 g) were dissolved in 1200 mL of dry CH$_2$Cl$_2$ in a 2000-mL three-neck flask. Eight drops of TFA were added to the reaction mixture, and resulting mixture was stirred in dark for 12 hours under nitrogen atmosphere at room temperature. After the complete consumption of aldehyde (1b) (which was conformed by TLC), DDQ (2,3-dichloro-5,6-dicyano-1,4-benzoquinone) (17.4 mmol 3.95 g) in 100 mL of CH$_2$Cl$_2$ was added to the reaction mixture. When the mixture was stirred for 30 minutes, 35 mL of diisopropylethylamine (DIEA) and 35 mL of BF$_3$.OEt$_2$ were added to the mixture. After the mixture was further stirred for 30 minutes, it was concentrated to 200 mL and filtered. The filtrate was washed once with sodium bicarbonate solution and twice with water, dried over anhydrous MgSO$_4$ and concentrated under reduced pressure. The crude product was purified by column chromatography using hexane/EtOAc (90/10 to 80/20, v/v) to obtain dark brown crystalline solid (4.2 g, 35%). $^1$H NMR (400 MHz, CDCl$_3$) δ 6.94 (d, J=8.8 Hz, 1H), 6.77-6.75 (m, 2H), 5.96 (s, 2H), 4.02 (t, J=6.8 Hz, 2H), 3.93 (t, J=6.8 Hz, 2H), 2.53 (s, 6H), 1.86-1.77 (m, 4H), 1.46 (s, 6H), 1.43-1.24 (m, 32H), 0.88-0.85 (m, 6H); $^{13}$C NMR (100 MHz, CDCl$_3$) δ 155.5, 150.0, 149.8, 143.4, 142.1, 132.2, 127.3, 121.2, 120.6, 115.0, 113.6, 69.7, 69.4, 32.1, 29.9, 29.8, 29.7, 29.6, 29.5, 29.4, 29.1, 26.3, 26.1, 22.9, 14.8, 14.6, 14.3; IR (cm$^{-1}$): 2921, 2852, 1543, 1509, 1467, 1412, 1372, 1306, 1263, 1156, 1136, 1121, 1084, 979, 817, 760, 723. ESI-MS. M$^+$ (C$_{43}$H$_{62}$BF$_2$N$_2$O$_2$) Calcd: m/z=692.8. Found: m/z=693.1.

Compound 4b.

When iodic acid (12.1 mmol, 2.13 g) in 5 mL of water was added dropwise to the ethanol solution (50 mL) containing compound 3b (5.7 mmol 4.0 g) and iodine (12.9 mmol 1.62 g) over 30 minutes, the mixture was stirred for 2 hours. After the completion of the reaction, the unreacted iodine was quenched with sodium thiosulphate solution and the mixture was concentrated under reduced pressure and dissolved in CH$_2$Cl$_2$, and washed twice with water and saturated saline solution. The organic layer was collected, dried over anhydrous MgSO$_4$ and concentrated under reduced pressure. The crude product was purified by column chromatography to yield 4b as red crystals (5.2 g, 98%). $^1$H NMR (400 MHz, CDCl$_3$) δ 6.96 (d, J=8.4 Hz, 1H), 6.73-6.71 (m, 2H), 4.04 (t, J=6.8 Hz, 2H), 3.92 (t, J=6.8 Hz, 2H), 2.62 (s, 6H), 1.87-1.77 (m, 4H), 1.48 (s, 6H), 1.45-1.24 (m, 32H), 0.88-0.84 (m, 6H); $^{13}$C NMR (100 MHz, CDCl$_3$) δ 156.8, 150.3, 150.2, 145.6, 141.8, 131.9, 127.0, 120.5, 114.1, 113.2, 85.7, 69.7, 69.5, 32.1, 29.9, 29.8, 29.7, 29.6, 29.5, 29.4, 26.2, 26.1, 22.9, 17.2, 16.2, 14.3; IR (cm$^{-1}$): 2917, 2849, 1542, 5122, 1508, 1463, 1397, 1345, 1311, 1263, 1243, 1213, 1184, 1140, 1119, 1082, 992:915, 759, 724. ESI-MS. M$^+$ (C$_{43}$H$_{65}$BF$_2$I$_2$N$_2$O$_2$) Calcd: m/z=944.6. Found: m/z=944.7.

Compound 5b.

Compound 4b (3.2 mmol, 3.0 g), CuI (0.02 mmol, 0.004 g) and Pd(PPh$_3$)$_2$Cl$_2$ (0.02 mmol, 0.015 g) were added to a 250-mL three-neck round-bottom flask under a nitrogen atmosphere. When 20 mL of anhydrous degassed THF, 30 mL of anhydrous diisopropylamine, and trimethylsilylacetylene (8.0 mmol, 0.78 g) were added to the flask, the mixture was stirred under reflux for 12 hours. After the completion of the reaction (which was monitored by TLC), the reaction mixture was concentrated and dissolved in 50 mL of CH$_2$Cl$_2$, washed twice with water and saturated saline solution. The organic layer was collected, dried over anhydrous MgSO$_4$, and concentrated under reduced pressure. The product was purified by neutralized silica gel column chromatography using hexane/EtOAc (95/5 to 80/20, v/v) to yield orange-red solid (2.2 g, 80%). $^1$H NMR (400 MHz, CDCl$_3$) δ 6.95 (d, J=8.4 Hz, 1H), 6.73-6.70 (m, 2H), 4.02 (t, J=6.8 Hz, 2H), 3.92 (t, J=6.8 Hz, 2H), 2.62 (s, 6H), 1.87-1.78 (m, 4H), 1.55 (s, 6H), 1.52-1.24 (m, 32H), 0.88-0.84 (m, 6H), 0.19 (s, 18H); $^{13}$C NMR (100 MHz, CDCl$_3$) δ 158.8, 150.2, 145.1, 143.1, 131.5, 126.6, 120.4, 116.3, 114.1, 113.2, 101.8, 97.4, 69.7, 69.5, 32.1, 29.9, 29.8, 29.8, 29.7, 29.6, 29.5, 29.4, 26.3, 26.2, 22.9, 14.3, 13.7, 0.28; $^{11}$B NMR (400 MHz, CDCl$_3$): 3.82 (t, J=97.6 MHz). IR (cm$^{-1}$): 2919, 2850, 246, 1531, 1517, 1470, 1391, 1316, 1268, 1249, 1197, 1139, 1092, 1072, 1013, 1003, 840, 761, 725, 700. ESI-MS. M$^+$ (C$_{53}$H$_{83}$BF$_2$N$_2$O$_2$Si$_2$) Calcd: m/z=885.2. Found: m/z=885.3.

Compound 6b.

When compound 5b (2.2 mmol, 2.0 g) was dissolved in degassed THF (50 mL) in a 250-mL flask at −70° C., tetrabutylammonium fluoride (TBAF) (5.6 mmol, 1.47 g, 5.6 mL of 1M solution) was added dropwise to the mixture via syringe. The reaction temperature was brought to the room temperature and the mixture was further stirred for 2 hours. After completion of the reaction, the mixture was acidified with acetic acid and extracted with CH$_2$Cl$_2$. The extracted organic layer washed twice with water and saturated saline solution, dried over anhydrous MgSO$_4$, and concentrated under reduced pressure. The crude product was purified by column chromatography using hexane/EtOAc (20/80, v/v) to give the desired product as orange-pink crystalline solid (1.1 g, 70%). $^1$H NMR (400 MHz, CDCl$_3$) δ 6.96 (d, J=8.4 Hz, 1H), 6.73-6.72 (m, 2H), 4.04 (t, J=6.8 Hz, 2H), 3.92 (t, J=6.8 Hz, 2H), 3.3 (s, 2H), 2.63 (s, 6H), 1.87-1.61 (m, 4H), 1.51 (s, 6H), 1.49-1.24 (m, 32H), 0.88-0.84 (m, 6H); $^{13}$C NMR (100 MHz, CDCl$_3$) δ 158.8, 150.2, 145.8, 143.6, 131.5, 126.4, 120.4, 115.2, 114.0, 113.1, 84.3, 76.2, 69.7, 69.4, 32.1, 29.9, 29.8, 29.7, 29.6, 29.4, 26.3, 26.1, 22.9, 14.3, 13.7, 13.6; $^{11}$B NMR (400 MHz, CDCl$_3$): 3.82 (t, J=97.6 MHz). IR (cm$^{-1}$): 3309, 2921, 2852, 2107, 1526, 1468, 1403, 1390, 1366, 1312, 1263, 1180, 1137, 1080, 1003, 761, 725. ESI-MS. M$^+$ (C$_{47}$H$_{67}$BF$_2$N$_2$O$_2$) Calcd: m/z=740.8. Found: m/z=739.1.

Polymer B.

Compound 4b (0.105 mmol, 0.100 g), compound 6b (0.115 mmol, 0.085 g), CuI (0.01 mmol, 0.002 g) were added to 100-mL flask under a nitrogen atmosphere. In the glove box, Pd(PPh$_3$)$_4$ (0.01 mmol, 0.012 g) was added to the flask. When a degassed mixed solution of anhydrous THF (20 mL) and anhydrous diisopropylamine (20 mL) were added to the flask, the mixture was stirred under reflux for 24 hours. After removal of the solvent, the residue was dissolved in methylene chloride (5 mL) added to 400 mL of ethanol and stirred for 2 hrs to precipitate the polymer. The precipitated solid was filtered and washed with excess ethanol and hexane. The obtained solid dried under vacuum for 24 h at room temperature to obtain dark-violet solid (0.155 g). $^1$H NMR (400 MHz, CDCl$_3$) δ 6.94 (br, 1H), 6.73 (br, 2H), 4.02 (br, 2H), 3.92 (br, 2H), 2.62 (s, 6H), 1.84 (br, 2H), 1.79 (br, 2H), 1.56 (s, 6H), 1.49-1.24 (m, 32H), 0.88-0.86 (m, 6H); $^{13}$C NMR (100 MHz, CDCl$_3$) δ 157.9, 150.0, 143.2, 142.5, 134.8, 131.6, 120.3, 116.3, 113.8, 113.1, 88.8, 69.5, 69.3, 31.9, 29.7, 29.6, 29.5, 29.4, 29.2, 26.0, 22.7, 16.9, 14.1, 13.5; IR (cm$^{-1}$): 2921, 2852, 1514, 1467, 1435, 1389, 1310, 1262, 1227, 1162, 1083, 995, 813, 760, 724.

Polymer C

Figure 37:
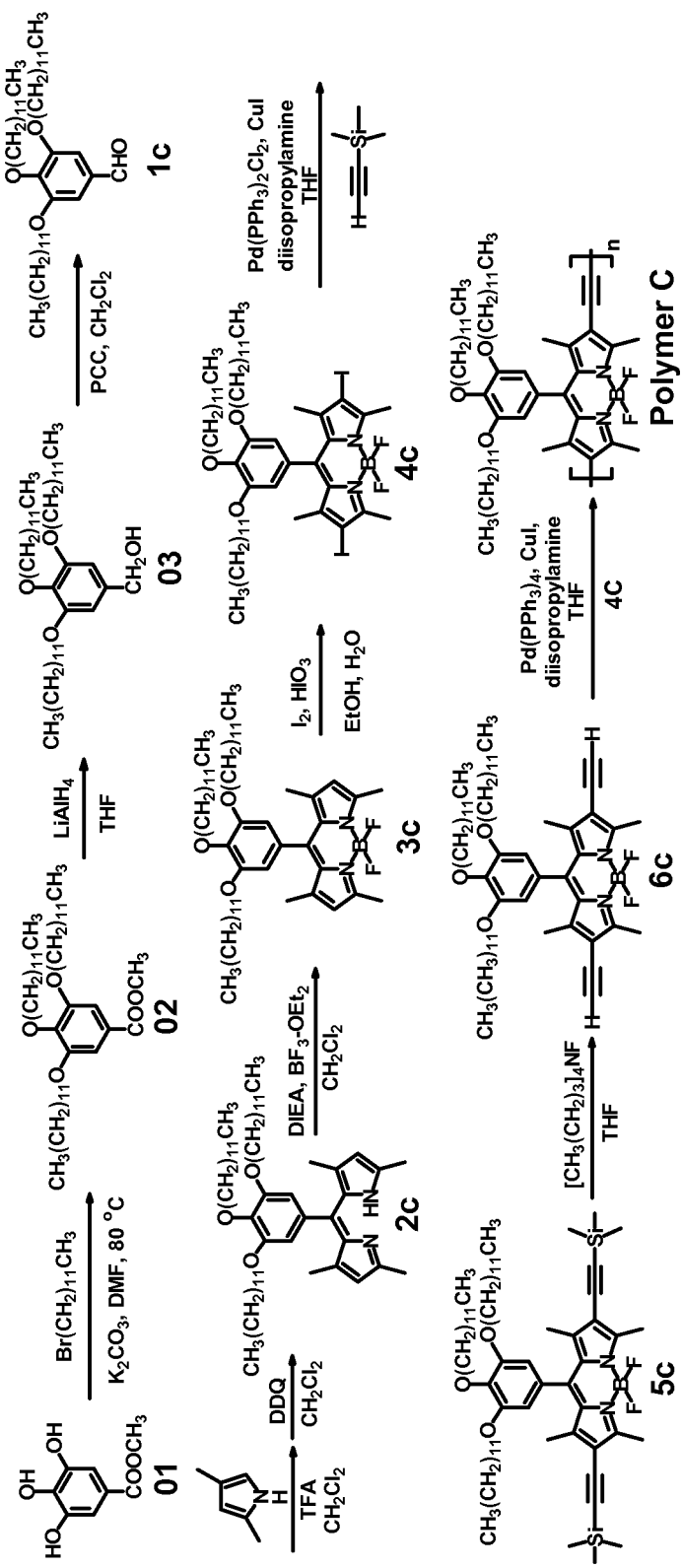
FIG. 37 shows synthetic route to a BODIPY based polymer.

The synthetic route to Polymer C is shown in FIG. 37 and detailed below.

Compound 02.

When 200 mL of degassed DMF was added to in a 500 mL three-neck round-bottom flask containing methyl-3,4,5-trihydroxybenzoate (13.6 mmol, 2.5 g), 1-bromododecane (47.6 mmol, 11.8 g) and K$_2$CO$_3$ (54 mmol, 7.5 g) under a nitrogen atmosphere, the mixture was stirred for 4 hours at 80° C. under a nitrogen atmosphere. After completion of the reaction (which was monitored by TLC), the reaction mixture was concentrated under reduced pressure, added to water and extracted with hexane. The organic layer was washed twice with water and saturated NaCl solution, dried over anhydrous MgSO$_4$ and concentrated under reduced pressure. The resulting crude product was purified by silica gel column chromatography using hexane/EtOAc (98/2, v/v) to obtain white solid (9.2 g, 98%). $^1$H NMR (400 MHz, CDCl$_3$) δ 7.23 (s, 2H), 4.02-4.00 (m, 6H), 3.86 (s, 3H), 1.80 (q, J=6.8 Hz, 6H), 1.49-1.44 (m, 6H), 1.33-1.25 (m, 48H), 0.88-0.84 (m, 9H); $^{13}$C NMR (100 MHz, CDCl$_3$) δ 167.1, 153.0, 142.6, 124.9, 108.2, 73.7, 69.4, 52.3, 32.1, 30.5, 29.9, 29.8, 29.7, 29.6, 29.5, 26.3, 26.1, 22.9, 14.3.

Compound 03.

Compound 02 (13.1 mmol, 9 g) in 50 ml of dry diethylether was added to LiAlH4 (26.2 mmol, 1 g) suspended in 100 ml diethylether in a dry 250 mL three-neck round-bottom flask. After stirring for 24 hrs, the reaction was quenched with ethanol and water at 0° C. the resulting solution was filtered and washed twice with water, dried over anhydrous MgSO$_4$ and concentrated under reduced pressure. The resulting crude product was purified by silica gel column chromatography to obtain white solid (5.6 g, 65%). $^1$H NMR (400 MHz, CDCl$_3$) δ 6.52 (s, 2H), 4.55 (s, 2H), 3.96-3.91 (m, 6H), 3.60 (t, J=6.4 Hz, 1H), 1.79-1.68 (m, 6H), 1.50-1.41 (m, 6H), 1.40-1.25 (m, 48H), 0.90-0.85 (m, 9H); $^{13}$C NMR (100 MHz, CDCl$_3$) δ 153.4, 137.7, 136.3, 105.5, 73.6, 69.3, 65.8, 63.2, 33.0, 32.1, 30.5, 29.9, 29.6, 26.3, 26.0, 22.9, 14.3.

Compound 1c.

Compound 03 (8.3 mmol, 5.5 g) and pyridiniumchlorocromate (PCC) (12.4 mmol, 2.6 g) were taken in a 250 ml round bottom flask and 100 ml of dry CH$_2$Cl$_2$ was added in nitrogen atmosphere. After refluxing for 4 hrs the mixture was filtered and the organic layer was washed with brine, dried over anhydrous MgSO$_4$ and concentrated under reduced pressure. The resulting crude product was purified by silica gel column chromatography to obtain white solid (5.1 g, 95%). $^1$H NMR (400 MHz, CDCl$_3$) δ 9.81 (s, 1H), 7.06 (s, 2H), 4.06-4.00 (m, 6H), 1.84-1.77 (m, 6H), 1.46-1.42 (m, 6H), 1.33-1.25 (m, 48H), 0.88-0.85 (m, 9H); $^{13}$C NMR (100 MHz, CDCl$_3$) δ 191.4, 153.7, 144.1, 131.7, 108.1, 73.8, 69.4, 32.1, 30.6, 29.9, 29.8, 29.6, 29.5, 26.3, 26.2, 22.9, 14.3.

Compound 3c.

1c (17.4 mmol, 11.4 g) and 2,4-dimethylpyrrole (34.88 mmol, 3.32 g) were dissolved in 1200 mL of dry CH$_2$Cl$_2$ in a 2000-mL three-neck flask. Eight drops of TFA were added to the reaction mixture, and resulting mixture was stirred in dark for 12 hours under nitrogen atmosphere at room temperature. After the complete consumption of aldehyde (1c) (which was conformed by TLC), DDQ (2,3-dichloro-5,6-dicyano-1,4-benzoquinone) (17.4 mmol 3.95 g) in 100 mL of CH$_2$Cl$_2$ was added to the reaction mixture. When the mixture was stirred for 30 minutes, 35 mL of diisopropylethylamine (DIEA) and 35 mL of BF$_3$.OEt$_2$ were added to the mixture. After the mixture was further stirred for 30 minutes, it was concentrated to 200 mL and filtered. The filtrate was washed once with sodium bicarbonate solution and twice with water, dried over anhydrous MgSO$_4$ and concentrated under reduced pressure. The crude product was purified by column chromatography using hexane/EtOAc (95/5 v/v) to obtain dark brown crystalline solid (4.5 g, 30%). NMR (400 MHz, CDCl$_3$) δ 6.45 (s, 2H), 5.97 (s, 2H), 3.99 (t, J=6.4 Hz, 2H), 3.90 (t, J=6.4 Hz, 4H), 2.53 (s, 6H), 1.75 (q, J=6.8 Hz, 6H), 1.52 (s, 6H), 1.48-1.42 (m, 6H), 1.40-1.24 (m, 48H), 0.88-0.85 (m, 9H); $^{13}$C NMR (100 MHz, CDCl$_3$) δ 155.6, 154.3, 143.3, 142.0, 138.9, 131.6, 129.8, 121.2, 106.6, 73.9, 69.6, 32.1, 30.5, 29.9, 29.8, 29.6, 29.5, 26.3, 26.2, 22.9, 14.7, 14.4, 14.3; IR (cm$^{-1}$): 2922, 2853, 1544, 1509, 1467, 1417, 1373, 1327, 1307, 1156, 1113, 1086, 1026, 977, 834, 804, 758, 721. ESI-MS. M$^+$ (C$_{55}$H$_{91}$BF$_2$N$_2$O$_3$) Calcd: m/z=877.1. Found: m/z=877.5.

Compound 4c.

When iodic acid (9.5 mmol, 1.6 g) in 5 mL of water was added dropwise to the ethanol solution (50 mL) containing compound 3c (4.5 mmol 4.0 g) and iodine (9.9 mmol 1.3 g) over 30 minutes, the mixture was stirred for 2 hours. After the completion of the reaction, the unreacted iodine was quenched with sodium thiosulphate solution and the mixture was concentrated under reduced pressure and dissolved in CH$_2$Cl$_2$, and washed twice with water and saturated saline solution. The organic layer was collected, dried over anhydrous MgSO$_4$ and concentrated under reduced pressure. The crude product was purified by column chromatography to yield 4c as red crystals (4.8 g, 96%). $^1$H NMR (400 MHz, CDCl$_3$) δ 6.41 (s, 2H), 4.01 (t, J=6.4 Hz, 2H), 3.89 (t, J=6.4 Hz, 4H), 2.62 (s, 6H), 1.75 (q, J=6.8 Hz, 6H), 1.53 (s, 6H), 1.49-1.43 (m, 6H), 1.40-1.24 (m, 48H), 0.88-0.84 (m, 9H); $^{13}$C NMR (100 MHz, CDCl$_3$) δ 156.9, 154.6, 145.6, 141.7, 139.2, 131.5, 129.4, 106.3, 85.7, 74.0, 70.0, 32.1, 30.5, 29.9, 29.8, 29.6, 29.5, 26.3, 26.2, 22.9, 17.1, 16.2, 14.3; IR (cm$^{-1}$): 2920, 2851, 1523, 1466, 1419, 1378, 1368, 1343, 1330, 1305, 1166, 1115, 993, 918, 831. ESI-MS. M$^+$ (C$_{55}$H$_{89}$BF$_2$I$_2$N$_2$O$_3$) Calcd: m/z=1128.9. Found: m/z=1129.1.

Compound 5c.

Compound 4c (3.5 mmol, 4.0 g), CuI (0.02 mmol, 0.004 g) and Pd(PPh$_3$)$_2$Cl$_2$ (0.02 mmol, 0.015 g) were added to a 250-mL three-neck round-bottom flask under a nitrogen atmosphere. When 20 mL of anhydrous degassed THF, 30 mL of anhydrous diisopropylamine, and trimethylsilylacetylene (8.8 mmol, 0.86 g) were added to the flask, the mixture was stirred under reflux for 12 hours. After the completion of the reaction (which was monitored by TLC), the reaction mixture was concentrated and dissolved in 50 mL of CH$_2$Cl$_2$, washed twice with water and saturated saline solution. The organic layer was collected, dried over anhydrous MgSO$_4$, and concentrated under reduced pressure. The product was purified by neutralized silica gel column chromatography using hexane/EtOAc (95/5 to 90/10, v/v) to yield orange-red solid (2.9 g, 78%). $^1$H NMR (400 MHz, CDCl$_3$) δ 6.40 (s, 2H), 4.00 (t, J=6.4 Hz, 2H), 3.88 (t, J=6.4 Hz, 4H), 2.61 (s, 6H), 1.76 (q, J=6.8 Hz, 6H), 1.59 (s, 6H), 1.49-1.43 (m, 6H), 1.40-1.24 (m, 48H), 0.88-0.84 (m, 9H), 0.19 (s, 18H); $^{13}$C NMR (100 MHz, CDCl$_3$) δ 158.9, 154.5, 145.1, 143.0, 139.1, 131.2, 129.1, 116.4, 106.2, 101.9, 97.3, 73.9, 69.7, 32.1, 30.5, 29.9, 29.8, 29.6, 29.5, 26.3, 26.2, 22.9, 14.3, 13.7, 13.5, 0.28; IR (cm$^{-1}$): 2922, 2853, 2151, 1536, 1469, 1420, 1391, 1316, 1248, 1197, 1101, 1004, 943, 853, 760, 721. $^{11}$B NMR (400 MHz, CDCl$_3$): 3.82 (t, J=97.6 MHz). ESI-MS. M$^+$ (C$_{65}$H$_{107}$BF$_2$N$_2$O$_3$Si$_2$) Calcd: m/z=1069.5. Found: m/z=1069.5.

Compound 6c.

When compound 5c (2.2 mmol, 2.4 g) was dissolved in degassed THF (50 mL) in a 250-mL flask at −70° C., tetrabutylammonium fluoride (TBAF) (5.6 mmol, 1.47 g, 5.6 mL of 1M solution) was added dropwise to the mixture via syringe. The reaction temperature was brought to the room temperature and the mixture was further stirred for 2 hours. After completion of the reaction, the mixture was acidified with acetic acid and extracted with CH$_2$Cl$_2$. The extracted organic layer washed twice with water and saturated saline solution, dried over anhydrous MgSO$_4$, and concentrated under reduced pressure. The crude product was purified by column chromatography using hexane/EtOAc (20/80, v/v) to give the desired product as dark orange-pink crystalline solid (1.4 g, 72%). $^1$H NMR (400 MHz, CDCl$_3$) δ 6.40 (s, 2H), 4.02 (t, J=6.4 Hz, 2H), 3.90 (t, J=6.4 Hz, 4H), 3.3 (s, 2H), 2.62 (s, 6H), 1.75 (q, J=6.8 Hz, 6H), 1.61 (s, 6H), 1.49-1.42 (m, 6H), 1.40-1.24 (m, 48H), 0.88-0.84 (m, 9H); $^{13}$C NMR (100 MHz, CDCl$_3$) δ 159.0, 154.5, 145.7, 143.4, 139.2, 131.1, 129.0, 115.2, 106.3, 84.5, 76.1, 73.9, 69.7, 32.1, 31.1, 30.5, 29.9, 29.8, 29.6, 29.5, 26.3, 26.2, 25.8, 22.9, 14.3, 13.7, 13.5. $^{11}$B NMR (400 MHz, CDCl$_3$): 3.82 (t, J=97.6 MHz). IR (cm$^{-1}$): 3300, 2922, 2853, 2108, 1526, 1469, 1420, 1387, 1334, 1310, 1183, 1112, 1066, 1003, 830, 720. ESI-MS. M$^+$ (C$_{59}$H$_{91}$BF$_2$N$_2$O$_3$) Calcd: m/z=925.2. Found: m/z=925.1.

Polymer C.

Compound 4c (0.13 mmol, 0.15 g), compound 6c (0.146 mmol, 0.135 g), CuI (0.01 mmol, 0.002 g) were added to 100-mL flask under a nitrogen atmosphere. In the glove box, Pd(PPh$_3$)$_4$ (0.01 mmol, 0.012 g) was added to the flask. When a degassed mixed solution of anhydrous THF (20 mL) and anhydrous diisopropylamine (20 mL) were added to the flask, the mixture was stirred under reflux for 24 hours. After removal of the solvent, the residue was dissolved in methylene chloride (5 mL), and added dropwise to 400 mL of ethanol to precipitate the polymer. The precipitated solid was collected by filtration and washed with excess ethanol and hexane. The obtained solid dried under vacuum for 24 h at room temperature to obtain dark-violet solid (0.196 g). $^1$H NMR (400 MHz, CDCl$_3$) δ 6.42 (s, 2H), 3.99 (br, 2H), 3.89 (br, 4H), 2.63 (s, 6H), 1.75 (br, 6H), 1.61 (s, 6H), 1.42 (br, 6H), 1.24 (br, 48H), 0.86-0.85 (br, 9H). $^{13}$C NMR (100 MHz, CDCl$_3$) δ 158.2, 154.5, 143.3, 141.1, 139.3, 131.4, 129.0, 115.2, 106.3, 94.6, 74.0, 69.7, 32.1, 31.1, 30.5, 29.9, 29.8, 29.6, 29.5, 26.3, 26.2, 25.8, 22.9, 14.3, 13.7, 13.5; IR (cm$^{-1}$): 2921, 2852, 1521, 1466, 1421, 1389, 1363, 1313, 1229, 1167, 1092, 1000, 758, 721.

Polymers A, B and C are soluble in common organic solvents such as chloroform, methylene chloride and THF. However, the solubility order is polymer C>polymer B>polymer A as the introduction of more side chains to each BODIPY core enhances solvation of conjugated polymers.

Photophysical Properties.

Figure 38:
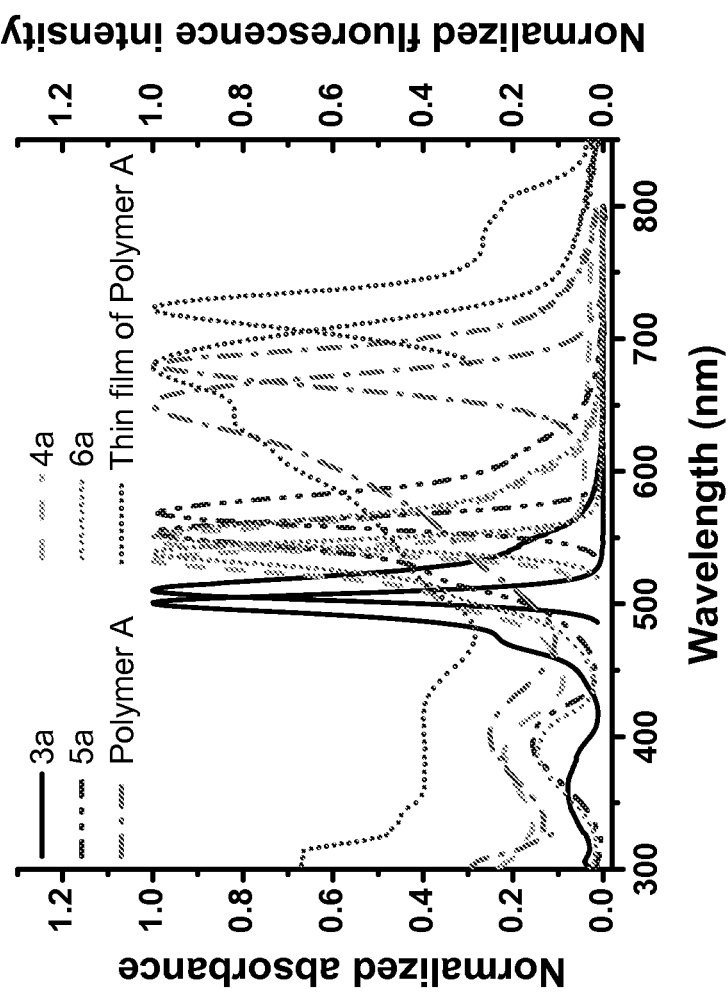
FIG. 38 shows absorption and fluorescence spectra for BODIPY dyes and polymers.
Figure 39:
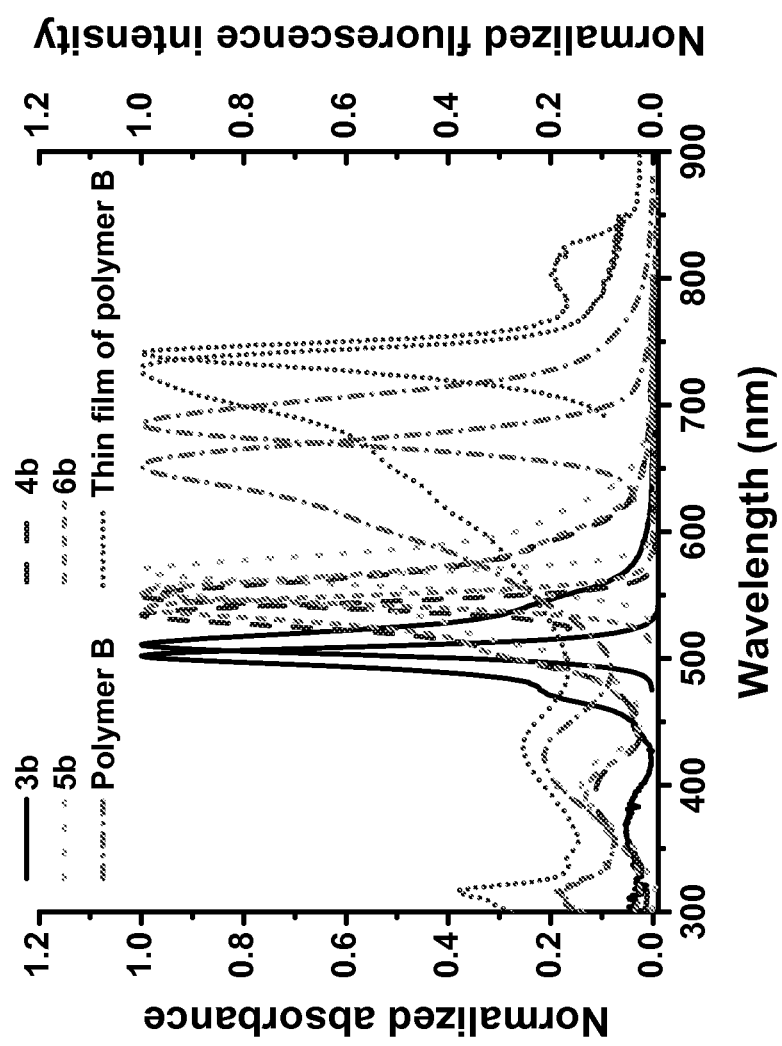
FIG. 39 shows absorption and fluorescence spectra for BODIPY dyes and polymers.
Figure 40:
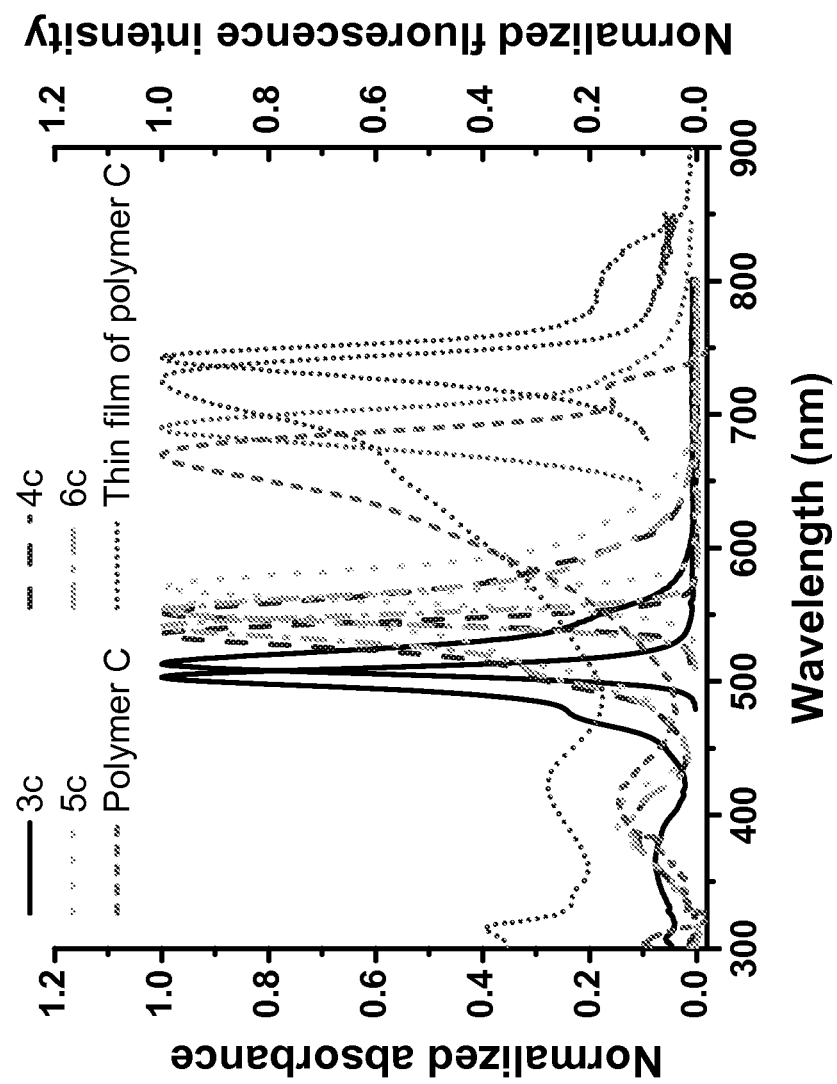
FIG. 40 shows absorption and fluorescence spectra for BODIPY dyes and polymers.

The absorption properties of green emissive BODIPY dye (3a) are characterized by a strong S$_0$→S$_1$ (π-π*) transition at 501 nm and a weaker broad band around 350 nm ascribed to the S$_0$→S$_2$ (π-π*) transition (FIG. 38). Introduction of 2,6-diiodo substituents to the BODIPY core leads to a large red shifts (33 nm and 38 nm) of both the UV-absorption and fluorescence maxima, respectively, significantly depresses the fluorescence quantum yield because of efficient intersystem crossing induced by the heavy atom effect of iodine (FIG. 38, Table 9). 2,6-Diethynylation of 2,6-diiodo-tetramethyl BODIPY (4a) results in a little red shift due to the enhanced conjugation. However, polymer A emits in deep red region at 680 nm, and exhibits pronounced bathochromic shifts (149 nm and 211 nm) of both the absorption and fluorescence maxima relative to the initial BODIPY dye (3a) because of its significant extension of π-conjugation (FIG. 40 and Table 9). Polymer B displays an absorption maximum at 662 nm and fluorescence maximum at 684 nm, a slight red shifted relative to polymer A. Polymer C displays a slight red shift compared with polymer B as it shows absorption maximum at 669 nm and fluorescence maximum at 690 nm (FIG. 40). The absorption peaks of conjugated polymers become broader than BODIPY monomers due to the extended π-conjugation (FIG. 40). In addition, polymers A, B and C display a little more Stokes shifts than their corresponding BODIPY dyes (Table 9). BODIPY dyes (3a, 3b, 3c, 5a, 5b, 5c, 6a, 6b and 6c) show fluorescence lifetimes in several nanoseconds (Table 9). However, the diiodo-functionalized BODIPY dyes (4a, 4b and 4c) display much shorter fluorescence lifetimes (ranging from 0.15 ns to 0.21 ns), consistent with their decreased quantum yields because of efficient intersystem crossing induced by the heavy atom effect of iodine (Table 9).

Arylation at the meso position has no significant effect on the absorption and emission maxima of BODIPY dyes since the arylated moiety is not coplanar with the BODIPY core due to steric hindrance although the substitution position is structurally different (Table 9). As a result, three different BODIPY monomers (4a-4-c and 6a-6c) each have only 1 or 2 nm difference among their respective absorption or emission spectral maxima. However, the absorption and emission maxima of polymer C are somewhat more red-shifted relative to those of polymers A and B, which might arise from amplification effect of conjugated polymers. Polymers A, B and C displays a little shorter fluorescence lifetimes than their starting BODIPY dyes (3a, 3b and 4c) (Table 9).

TABLE 9

Absorption and emission maxima, and quantum yields of BODIPY dyes and polymers in methylene chloride solution. Quantum yields of BODIPY dyes and polymeric dyes were determined by use of fluorescein (quantum yield of 0.85 in 0.1N NaOH) as a standard.

| | BODIPY dyes or polymers | | | | | |
| --- | --- | --- | --- | --- | --- | --- |
| | 3a | 4a | 5a | 6a | Polymer A | Thin film of polymer A |
| Absorption maxima (nm) | 501 | 533 | 554 | 539 | 650 | 680 |
| Emission maxima (nm) | 509 | 548 | 569 | 551 | 680 | 723 |
| Quantum yield (%) | | 2.3 | | | | |
| Fluorescence lifetime (ns) | 3.9 | 0.21 | 4.4 | 3.6 | 1.4 | |
| Stokes shift (nm) | 8 | 15 | 15 | 12 | 30 | 43 |

TABLE 9-continued

Absorption and emission maxima, and quantum yields of BODIPY dyes and polymers in methylene chloride solution. Quantum yields of BODIPY dyes and polymeric dyes were determined by use of fluorescein (quantum yield of 0.85 in 0.1N NaOH) as a standard.

| | BODIPY dyes or polymers | | | | | |
|---|---|---|---|---|---|---|
| | 3b | 4b | 5b | 6b | Polymer B | Thin film of polymer B |
| Absorption maxima (nm) | 502 | 534 | 555 | 540 | 662 | 728 |
| Emission maxima (nm) | 510 | 549 | 5.70 | 5.52 | 68.4 | 7.41 |
| Quantum yield (%) | | 2.7 | | | | |
| Fluorescence lifetime (ns) | 4.1 | 0.15 | 4.6 | 3.9 | 1.1 | |
| Stokes shift (nm) | 8 | 15 | 15 | 12 | 22 | 12 |

| | BODIPY dyes or polymers | | | | | |
|---|---|---|---|---|---|---|
| | 3c | 4c | 5c | 6c | Polymer C | Thin film of polymer C |
| Absorption maxima (nm) | 503 | 535 | 556 | 541 | 669 | 726 |
| Emission maxima (nm) | 511 | 550 | 570 | 553 | 690 | 743 |
| Quantum yield (%) | | 2.3 | | | | |
| Fluorescence lifetime (ns) | 3.2 | 0.19 | 4.4 | 3.0 | 1.6 | |
| Stokes shift (nm) | 9 | 15 | 14 | 12 | 19 | 19 |

Thermal Stabilities of the Polymers.

Figure 41:
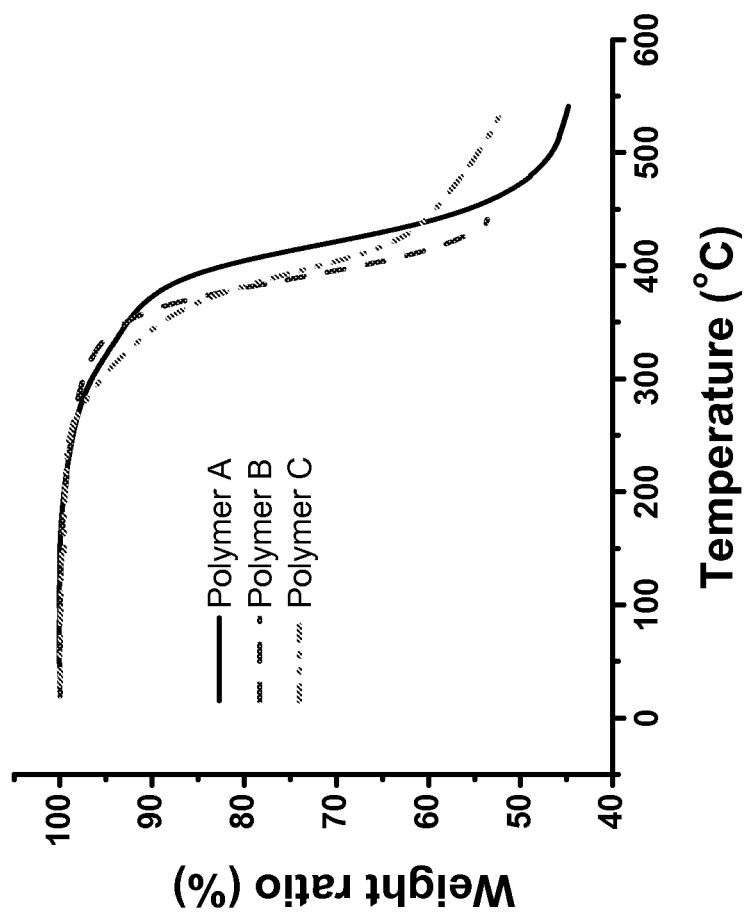
FIG. 41 shows TGA curves for BODIPY based polymers.

Thermal stabilities of polymers A, B and C were determined by thermogravimetrc analysis (TGA) at the heating rate of 20° C./min under nitrogen atmosphere. From the graphs, the thermal decomposition temperatures ($T_d$) of the polymers ranged from 270 to 360° C., which suggests their good thermal stability. (FIG. 41) The small amount of weight loss of polymer C before its $T_d$ is probably due to decomposition of the oliogmers. Differential scanning calorimetry (DSC) of polymers did not give a clear phase transition, which may arise from that polymer chain movements are limited by their rigid structures.

Example 14

Synthesis of Fluorescent Conjugated Glycopolymers A-E

Figure 42:
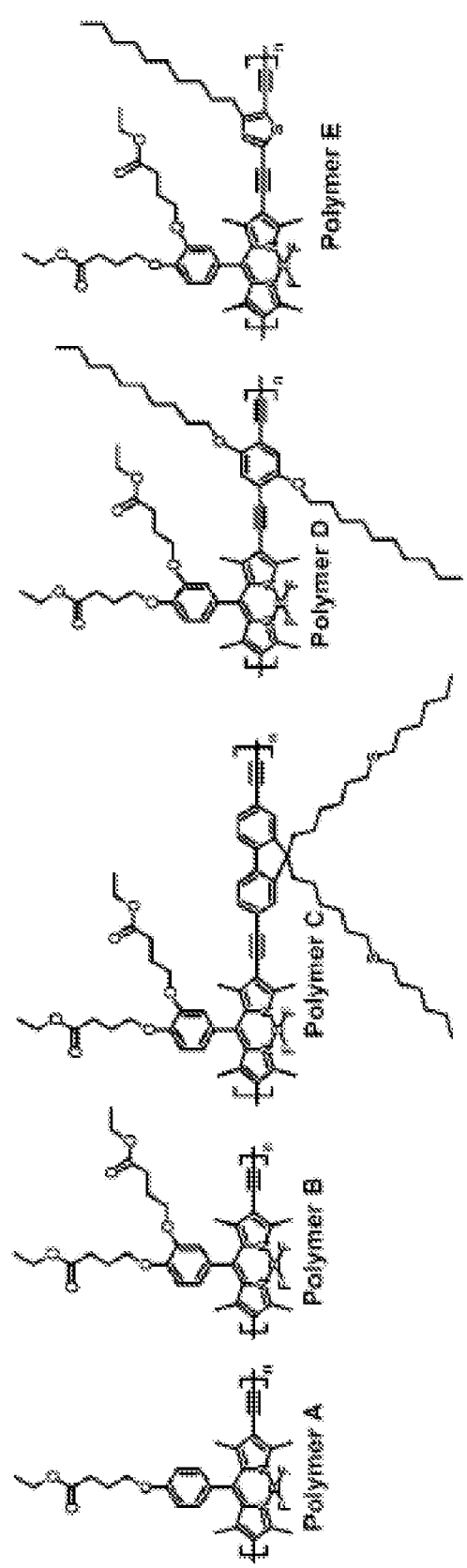
FIG. 42 shows chemical structures of conjugated polymers with BODIPY backbone

The structures of Polymers A-E are shown in FIG. 42

Instrumentation.

$^1$H NMR and $^{13}$C NMR spectra were taken on a 400 MHz Varian Unity Inova spectrophotometer instrument. $^1$H and $^{13}$C NMR spectra were recorded in CDCl$_3$, and chemical shifts (δ) are given in ppm relative to solvent peaks ($^1$H, δ 7.26; $^{13}$C, δ 77.3) as internal standard. UV spectra were taken on a Hewlett-Packard 8452A Diode Array UV-visible spectrophotometer. Fluorescence spectra were recorded on a Spex Fluorolog 1681 0.22 m steady-state fluorometer. Fluorescence quantum yields of BODIPY dyes and polymers were measured in methylene chloride and calculated by using fluorescein excited at 490 nm in 0.1 N NaOH as the reference (quantum efficiency, cPn=85%). Fluorescence lifetimes were measured on a 010-3300 Nitrogen Laser laserstrobe PTI instrument and analyzed using FeliX32 software. Molecular weights of the polymers were determined by gel permeation chromatography (OPC) by using a Waters associates model 6000A liquid chromatograph. Three American Polymer Standards Corp. ultrastyragel columns in series with porosity indices of 103, 104, and 105 A were used and housed in an oven thermostatted at 30° C. The mobile phase was HPLC grade THF which was filtered and degassed by vacuum filtration through a 0.5 μm fluoropore filter prior to use. The polymers were detected by a Waters Model 440 ultraviolet absorbance detector at a wavelength of 254 nm and a Waters Model 2410 refractive index detector. Molecular weights were determined relative to polystyrene standards.

Materials.

Unless otherwise indicated, all reagents and solvents were obtained from commercial suppliers (Aldrich, Sigma, Fluka, Acros Organics, Fisher SCIentific, Lancaster) and were used without further purification. Air- and moisture-sensitive reactions were conducted in oven-dried glassware using a standard Schlenk line or drybox techniques under an inert atmosphere of dry nitrogen. 9,9-Bis-(6'-bromohexyl)-2,7-diido-9H-fluorene, 1,4-diiodo-2,5didecyloxybenzene (7b), and 2,5-diiodo-3-decylthiophene (7C) were prepared according to the reported procedures.

Polymer A

Figure 44:
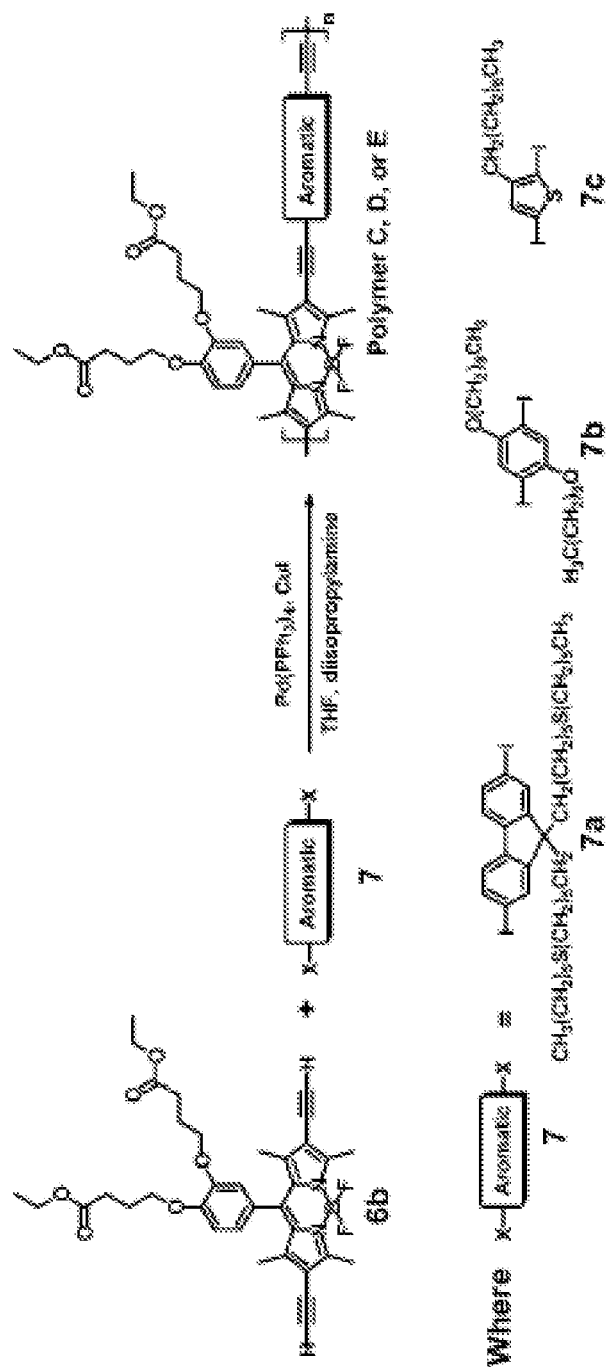
FIG. 44 shows a synthetic route to a BODIPY based polymer.

The synthetic route to Polymer A is shown in FIG. 44 and is detailed below.

Ethyl 4-(4-Formylphenoxy)butanoate (1a)

When 150 mL of degassed DMF was added to a 500 mL three-neck round-bottom flask containing 4-hydroxybezaldehyde (40.9 mmol, 5 g), ethyl 4-bromobuterate (49.1 mmol, 9.57 g), and K$_2$CO$_3$ (122 mmol, 16.8 g) under a nitrogen atmosphere, the mixture was stirred for 4 h at 80° C. under a nitrogen atmosphere. After completion of the reaction (which was monitored by TLC), the reaction mixture was concentrated under reduced pressure. The residue was dissolved in 50 mL of EtOAc and washed twice with water and saturated NaCl solution. The organic layer was collected, dried over anhydrous MgSO4, and concentrated under reduced pressure. The resulting crude product was purified by silica gel column chromatography using hexane/EtOAc (70/30, v/v) to obtain white solid (9.36 g, 97%). $^1$H NMR (400 MHz, CDCl$_3$): δ 9.85 (s, $^7$H), 7.80 (d, J=8.8 Hz, 2H), 6.99 (d, J=8.8 Hz, 2H), 4.12 (q, J=7.2 Hz, 2H), 4.07 (t, J=6.0 Hz, 2H), 2.50 (t, J=7.2 Hz, 2H), 2.12 (q, J=6.4, 2H), 1.26 (t, J=7.2 Hz, 3H). $^{13}$C NMR (100 MHz, CDCl$_3$): δ 190.9, 173.2, 164.1, 132.2, 130.2, 114.9, 67.3, 60.7, 30.8, 24.6, 14.4.

BODIPY Dye 3a.

Ethyl 4-(4-formylphenoxy)butanoate (1a) (8.72 mmol, 2.07 g) and 2,4-dimethylpyrrole (17.44 mmol, 1.66 g) were dissolved in 1000 mL of dry CH$_2$Cl$_2$ in a 2000-mL threeneck flask. Eight drops of trifluoroacetic acid (TFA) were added to the reaction mixture, and the resulting mixture was stirred in the dark for 12 h under nitrogen atmosphere at room temperature. After the complete consumption of aldehyde (1a) (which was monitored by TLC), DDQ (2,3-dichloro-5,6-dicyano-1,4-benzoquinone) (8.72 mmol 1.974 g) in 10 mL of CH$_2$Cl$_2$ was added to the reaction mixture. When the mixture was stirred for 30 min, 17 mL of diisopropylethylamine (DIEA) and 17 mL of BF$_3$.OEt$_2$ were added to the mixture. After the mixture was further stirred for 30 min, it was concentrated to 200 mL and filtered. The filtrate was washed twice with water and brine solution, dried over anhydrous $MgSO_4$, and concentrated under reduced pressure. The crude product was purified by column chromatography using hexane/EtOAc (90/10 to 70/30, v/v) to obtain a dark brown crystalline solid (1.51 g, 38%). $^1$H NMR (400 MHz, $CDCl_3$): δ 7.13 (d, J=8.4 Hz, 2H), 6.96 (d, J=8.4 Hz, 2H), 5.95 (s, 2H), 4.14 (q, J=7.2 Hz, 2H), 4.04 (t, J=6.2 Hz, 2H), 2.54-2.51 (m, 8H), 2.15-2.11 (m, 2H), 1.40 (s, 6H), 1.25 (t, J=7.2 Hz, 3H). $^{13}$C NMR (100 MHz, $CDCl_3$): δ 173.3, 159.6, 155.4, 143.3, 142.0, 132.0, 129.4, 127.3, 121.2, 115.2, 67.0, 60.67, 30.9, 24.8, 14.8, 14.4. IR: 2954, 2922, 2970, 1736, 1609, 1542, 1514, 1464, 1441, 1408, 1375, 1365, 1309, 1281, 1261, 1239, 1191, 1179, 1153, 1090, 1043, 937, 828, 802, 763, 703 $em^{-1}$. ESI-MS: $M^+$ ($C_{25}H_{29}BF_2N_2O_3$) calcd, m/z=454.2. found, m/z=454.9. It shows absorption maximum at 501 nm and emission maximum at 510 nm in $CH_2Cl_2$ solution.

BODIPY Dye 4a.

When iodic acid (6.13 mmol, 1.08 g) in 5 mL of water was added dropwise to the ethanol solution 50 mL) containing compound 3a (3.1 mmol 1.4 g) and iodine (6.7 mmol 0.85 g) over 30 min, the mixture was stirred for 2 h.[14] After the completion of the reaction, the mixture was concentrated under reduced pressure, dissolved in $CH_2Cl_2$ and washed twice with water and saturated saline solution. The organic layer was collected, dried over anhydrous $MgSO_4$, and concentrated under reduced pressure. The crude product was purified by column chromatography to yield 4a as red crystals (2.1 g, 98%). $^1$H NMR (400 MHz, $CDCl_3$): δ 7.11 (d, J=8.4 Hz, 2H), 6.99 (d, J=8.4 Hz, 2H), 4.15 (q, J=7.2 Hz, 2H), 4.06 (t, J=6.0 Hz, 2H), 2.62 (s, 6H), 2.54 (t, J=6.0, 2H), 2.17-2.13 (m, 2H), 1.42 (s, 6H), 1.26 (t, J=6.8 Hz, 3H). $^{13}$C NMR (100 MHz, $CDCl_3$): δ 173.3, 160.0, 156.8, 145.5, 141.7, 131.9, 129.3, 126.9, 115.5, 85.7, 67.2, 60.7, 30.9, 24.8, 17.4, 16.2, 14.5. IR: 2961, 2899, 1720, 1605, 1538, 1509, 1464, 1431, 1398, 1344, 1310, 1296, 1263, 1225, 1177, 1073, 1042, 1000, 916, 837, 763, 705 $em^{-1}$. ESI-MS: $M^+$ ($C_{25}H_{27}BF_2I_2N_2O_3$) calcd, m/z=706.0. found, m/z=705.6. It shows an absorption maximum at 533 nm and emission maximum at 548 nm in $CH_2Cl_2$ solution.

BODIPY Dye 5a.

BODIPY dye 4a (1.69 mmol, 1.2 g), CuI (0.02 mmol, 0.004 g), and $Pd(PPh_3)_2Cl_2$ (0.02 mmol, 0.015 g) were added to a 100-mL three-neck round-bottom flask under a nitrogen atmosphere. When 20 mL of anhydrous degassed THF, 20 mL of anhydrous diisopropylamine, and trimethylsilylacetylene 5.0 mmol, 0.49 g) were added to the flask, the mixture was stirred under reflux for 4 h. After the completion of the reaction (which was monitored by TLC), the reaction mixture was concentrated and dissolved in 50 mL of $CH_2Cl_2$ and washed twice with water and saturated saline solution. The organic layer was collected, dried over anhydrous $MgSO_4$, and concentrated under reduced pressure. The product was purified by silica gel column chromatography using hexane/EtOAc (95/5 to 80/20, v/v) to yield orange-red solid (0.91 g, 84%). $^1$H NMR (400 MHz, $CDCl_3$): δ 7.17 (d, J=8.4 Hz, 2H), 6.98 (d, J=8.4 Hz, 2H), 4.15 (q, J=7.2 Hz, 2H), 4.05 (t, J=6.0 Hz, 2H), 2.60 (s, 6H), 2.54 (t, J=6.0, 2H), 2.16-2.13 (m, 2H), 1.48 (s, 6H), 1.26 (t, J=6.8 Hz, 3H) 0.19 (s, 18H). $^{13}$C NMR (100 MHz, $CDCl_3$): δ 173.3, 159.9, 158.7, 145.1, 143.1, 131.6, 129.3, 126.7, 116.3, 115.4, 101.8, 97.4, 67.1, 60.7, 30.9, 24.8, 14.4, 13.8, 0.28. IR: 2955, 2923, 2152, 1737, 1609, 1530, 1472, 1393, 1366, 1318, 1290, 1247, 1198, 1174, 1086, 1048, 1001, 946, 930, 765, 703 $em^{-1}$. ESI-MS $[M]^+$ ($C_{35}H_{45}BF_2N_2O_3Si_2$) calcd, m/z=646.3. found, m/z=647.4.

It shows absorption maximum at 553 nm and emission maximum at 569 nm in $CH_2Cl_2$ solution.

BODIPY Dye 6a.

When BODIPY dye 5a (0.77 mmol, 0.50 g) was dissolved in degassed THF (8 mL) in a 50-mL flask at −70 DC, tetrabutylammonium fluoride (TBAF) (3.1 mmol, 3 mL of 1 M solution) was added dropwise to the mixture via syringe under a nitrogen atmosphere. The reaction temperature was brought to the room temperature, and the mixture was further stirred for 4 h under nitrogen atmosphere. After completion of the reaction, the reaction mixture was acidified with acetic acid, diluted with water, and then extracted with 50 mL of $CH_2Cl_2$. When the reaction mixture was concentrated under reduced pressure, the residue was dissolved in 50 mL of $CH_2Cl_2$ and washed twice with water and saturated saline solution. The organic layer was collected, dried over anhydrous $MgSO_4$, and concentrated under reduced pressure. The crude product was purified by column chromatography using hexane/EtOAc (20/80, v/v) to give the desired product as orange-pink crystalline solid (0.29 g, 76%). $^1$H NMR (400 MHz, $CDCl_3$): δ 7.11 (d, J=8.4 Hz, 2H), 6.99 (d, J=8.4 Hz, 2H), 4.15 (q, J=7.2 Hz, 2H), 4.06 (t, J=6.0 Hz, 2H), 3.29 (s, 2H), 2.62 (s, 6H), 2.54 (t, J=6.0, 2H), 2.17-2.13 (m, 2H), 1.50 (s, 6H), 1.26 (t, J=6.8 Hz, 3H). $^{13}$C NMR (100 MHz, $CDCl_3$): δ 173.3, 159.9, 158.9, 145.7, 143.5, 131.5, 129.2, 126.4, 115.5, 115.2, 84.2, 76.2, 67.1, 60.7, 30.9, 29.9, 24.8, 14.4, 13.7. IR: 3293, 3257, 2936, 1719, 1529, 1474, 1394, 1368, 1316, 1288, 1272, 1244, 1196, 1178, 1004, 953, 806, 766, 707 $em^{-1}$. ESI-MS $[M]^+$ ($C_{29}H_{23}BF_2N_2O_3$) calcd, m/z=502.2. found, m/z=503.1. It shows absorption maximum at 538 nm and emission maximum at 552 nm in $CH_2Cl_2$ solution.

Polymer A.

BODIPY dye 4a (0.133 mmol, 94 mg), BODIPY dye 6a (0.139 mmol, 70 mg), and CuI (2 mg) were added to a 100-mL flask under a nitrogen atmosphere. In the glovebox, $Pd(PPh_3)_4$ 5 mg) was added to the flask. When a degassed mixed solution of anhydrous THF (20 mL) and anhydrous diisopropylamine (20 mL) were added to the flask, the mixture was stirred under reflux for 24 h. After removal of the solvent, the residue was dissolved in methylene chloride. The organic layer was washed with water, dried over anhydrous $MgSO_4$, and filtered. Then the filtrate was concentrated under reduced pressure and added to 200 mL of ethanol to precipitate the polymer. The precipitated solid was collected, washed with ethanol, and dried under vacuum for 24 h at room temperature to obtain dark-violet solid (0.102 g). $^1$H NMR (400 MHz, CDCh): δ 7.11 (d, 2H), 6.99 (d, 2H), 4.15 (broad q, 2H), 4.06 (broad t, 2H), 2.62 (s, 6H), 2.54 (broad t, 2H), 2.17-2.13 (broad m, 2H), 1.42 (s, 6H), 1.27 (broad t, 3H). $^{13}$C NMR (100 MHz, $CDCl_3$): δ 173.3, 159.9, 158.1, 143.3, 142.3, 131.5, 129.2, 126.9, 116.5, 115.5, 89.0, 67.1, 60.7, 30.9, 29.9, 24.8, 14.4, 13.7. IR: 2925, 1732, 1608, 1513, 1472, 1436, 1390, 1313, 1226, 1164, 1088, 836, 765, 703 $em^{-1}$. It shows absorption maximum at 659 nm and emission maximum at 678 nm in $CH_2Cl_2$ solution. OPC (THF, polystyrene standard), $M_n$=16500 g/mol; polydispersity=1.8.

Polymer B

Figure 43:
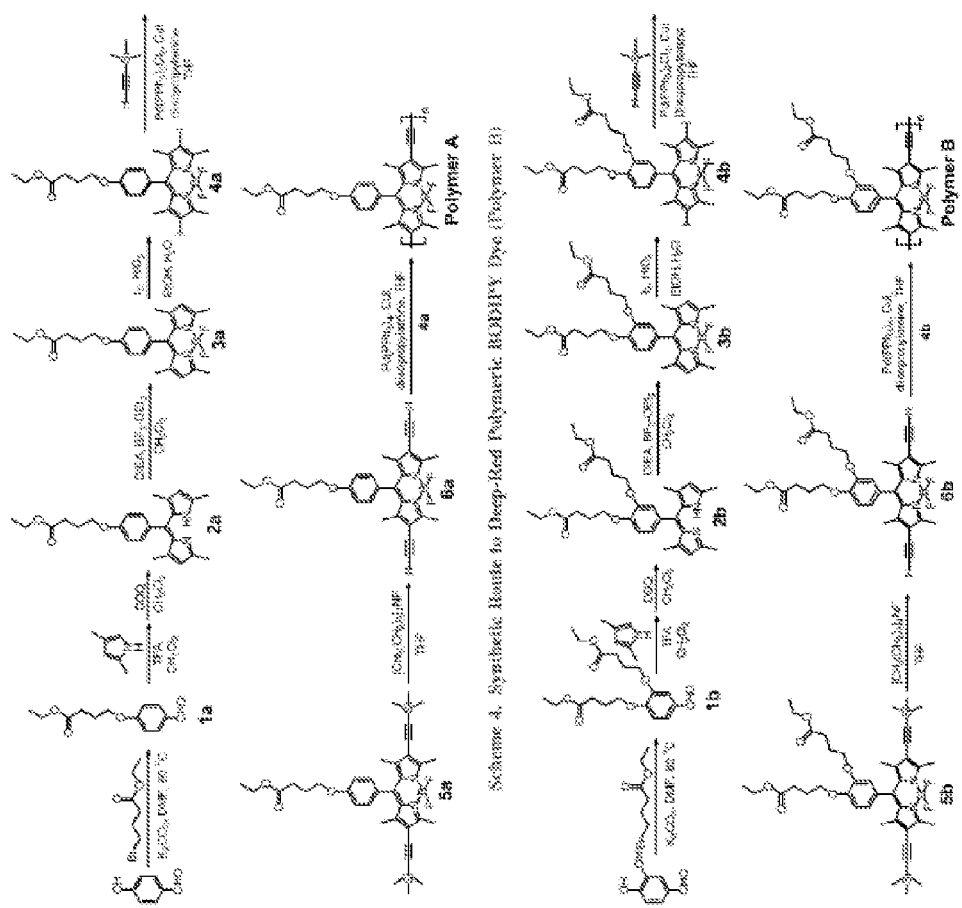
FIG. 43 shows a synthetic route to a BODIPY based polymer.

The synthetic route to Polymer B is shown in FIG. 43 and is detailed below.

Compound 1b.

When 200 mL of DMF was added to a 500-mL three-neck round-bottom flask containing 3,4-dihydroxybezaldehyde 59.7 mmol, 8 g), ethyl 4-bromobuterate (143.3 mmol, 27.9 g), and $K_2CO_3$ (238.8 mmol, 32.4 g) under a nitrogen atmosphere, the mixture was stirred for 4 h at 80° C. under a nitrogen atmosphere. After completion of the reaction (which was monitored by TLC), DMF was removed from the mixture under reduced pressure. The residue was dissolved in 150 mL of EtOAc and washed with water and saturated saline solution twice. The organic layer was collected, dried over $MgSO_4$, and concentrated under reduced pressure. The resulting crude product was purified by silica gel column chromatography using hexane/EtOAc (70/30, v/v) to obtain white solid (20.7 g, 95%). $^1$H NMR (400 MHz, $CDCl_3$): δ 9.80 (s, LH), 7.42-7.37 (m, 2H), 6.94 (d, J=8.0 Hz, LH), 4.15-4.06 (m, 8H), 2.54-2.49 (m, 4H), 2.17-2.12 (m, 4H), 1.23 (t, J=7.2 Hz, 6H). $^{13}$C NMR (100 MHz, $CDCl_3$): δ 191.0, 173.2, 154.4, 149.3, 130.3, 126.9, 112.2, 111.5, 68.1, 68.0, 60.6, 30.8, 30.6, 24.6, 24.5, 14.4.

BODIPY Dye 3b.

Compound 1b (8.72 mmol, 3.19 g) and 2,4-dimethylpyrrole (17.44 mmol, 1.66 g) were added to degassed anhydrous 1000 mL of $CH_2Cl_2$ in a 2000-mL three-neck roundbottom flask. When eight drops of TFA were added to the reaction mixture, the mixture was stirred in the dark for 12 h at room temperature under nitrogen atmosphere. After the completion of aldehyde (1b) (which was conformed by TLC), DDQ (2,3-dichloro-5,6-dicyano-1,4-benzoquinone) (8.72 mmol 1.974 g) in $CH_2Cl_2$ was added. After the mixture was stirred for 30 min, DIEA (diisopropylethylamine) (17 mL) and $BF_3.OEt_2$ (17 mL) were added. When the mixture was stirred for ½ h, it was concentrated to 200 mL and filtered. The filtrate was washed twice with water and brine solution, dried over $MgSO_4$ and concentrated under reduced pressure. The crude product was purified by column chromatography using hexane/EtOAc (90/10 to 70/30, v/v) to obtain a dark brown crystalline solid (1.8 g, 37%). $^1$H NMR (400 MHz, $CDCl_3$): δ 6.95 (d, J=8.4 Hz, LH), 6.78-6.76 (m, 2H), 5.95 (s, LH), 4.17-4.05 (m, 6H), 3.98 (t, J=6.0 Hz, 2H), 2.56-2.48 (m, 10H), 2.18-2.08 (m, 4H), 1.44 (s, 6H), 1.26-1.20 (m, 6H). $^{13}$C NMR (100 MHz, $CDCl_3$): δ 173.3, 173.2, 155.5, 149.7, 149.6, 143.3, 141.7, 131.8, 127.7, 121.3, 121.1, 114.3, 113.9, 68.5, 68.2, 60.6, 30.8, 24.8, 14.7, 14.6, 14.4. IR: 2926, 1739, 1720, 1543, 1509, 1470, 1413, 1371, 1306, 1265, 1160, 1134, 1060, 1037, 1007, 975, 954, 824, 802, 760, 744, 726 $em^{-1}$. ESI-MS $[M+Na]^+$ ($C_{31}H_{39}BF_2N_2O_6Na$) calcd, m/z=607.3. found, m/z=607.3. It shows absorption maximum at 502 nm and emission maximum at 511 nm in $CH_2Cl_2$ solution.

BODIPY Dye 4b.

When iodic acid (6.13 mmol, 1.08 g) in 5 mL of water was added dropwise to the ethanol solution 50 mL) containing BODIPY dye 3b (3.1 mmol 1.8 g) and iodine (6.7 mmol 0.85 g) over 30 min, the mixture was stirred for 2 h. After the completion of the reaction, the reaction mixture was concentrated under reduced pressure and dissolved in $CH_2Cl_2$. The organic layer was washed twice with water and with saturated saline solution, dried over $MgSO_4$, and concentrated under reduced pressure. The crude product was purified by column chromatography using hexane/EtOAc (80/20, v/v) to yield 4b as red crystals (2.5 g, 98%). $^1$H NMR (400 MHz, $CDCl_3$): δ 6.97 (d, J=8.4 Hz, LH), 6.75-6.71 (m, 2H), 4.17-4.09 (m, 6H), 3.97 (t, J=6.0 Hz, 2H), 2.61 (s, 6H), 2.57-2.48 (m, 4H), 2.18-2.08 (m, 4H), 1.45 (s, 6H), 1.27-1.20 (m, 6H). $^{13}$C NMR (100 MHz, $CDCl_3$): δ 173.3, 173.1, 156.8, 150.0, 149.9, 145.5, 141.4, 131.8, 127.2, 120.9, 114.3, 113.6, 85.7, 68.6, 68.2, 60.6, 30.8, 24.8, 17.3, 16.2, 14.4. IR: 2977, 2957, 2772, 2931, 1730, 1539, 1508, 1463, 1396, 1345, 1309, 1265, 1245, 1178, 1138, 1119, 1085, 1048, 989, 956, 758, 724 $em^{-1}$. ESI-MS $[M+Na]^+$ ($C_{31}H_{37}BF_2I_2N_2O_6Na$) calcd, m/z=859.1. found, m/z=859.4. It shows absorption maximum at 534 nm and emission maximum at 549 nm in $CH_2Cl_2$ solution.

BODIPY Dye 5b.

BODIPY dye 4b (1.7 mmol, 1.5 g), CuI (0.02 mmol, 4 mg) and Pd(PPh$_3$)$_2$Cl$_2$ (0.02 mmol, 15 mg) were added to a 100-mL three-neck round-bottom flask under nitrogen atmosphere. When degassed anhydrous THF (20 mL), anhydrous diisopropylamine (20 mL), and trimethylsilylacetylene 5.3 mmol, 0.52 g) were added to the flask, the mixture was stirred under reflux for 4 h. After the completion of the reaction (which was monitored by TLC), the reaction mixture was concentrated under reduced pressure, dissolved in 50 mL of $CH_2Cl_2$ and washed twice with water and saturated saline solution. The organic layer was collected, dried over $MgSO_4$, and concentrated under reduced pressure. The product was purified by silica gel column chromatography using hexane/EtOAc (95/5 to 70/30, v/v) to yield orange-red solid (1.07 g, 82%). $^1$H NMR (400 MHz, $CDCl_3$): δ 6.96 (d, J=8.4 Hz, LH), 6.74-6.71 (m, 2H), 4.15-4.07 (m, 6H), 3.97 (t, J=6.0 Hz, 2H), 2.60 (s, 6H), 2.57-2.48 (m, 4H), 2.18-2.09 (m, 4H), 1.52 (s, 6H), 1.27-1.20 (m, 6H), 0.19 (s, 18H). $^{13}$C NMR (100 MHz, $CDCl_3$): δ 173.3, 173.1, 158.8, 149.9, 149.8, 145.0, 142.7, 131.4, 127.0, 120.9, 116.4, 114.3, 113.6, 101.9, 97.3, 68.6, 68.2, 60.6, 30.8, 24.8, 14.4, 13.7, 13.6, 0.28. IR: 2921, 2852, 2201, 1604, 1513, 1467, 1435, 1389, 1363, 1310, 1263, 1227, 1162, 1083, 994, 814, 760, 724 $em^{-1}$. ESI-MS $[M]^+$ ($C_{41}H_{55}BF_2N_2O_6Si_2$) calcd, m/z=776.4. found, m/z=776.9. It shows absorption maximum at 554 nm and emission maximum at 570 nm in $CH_2Cl_2$ solution.

BODIPY Dye 6b.

When BODIPY dye 5b (0.65 mmol, 0.50 g) was dissolved in degassed THF (8 mL) in a 50-mL flask at −70 DC, tetrabutylammonium fluoride (TRAF) (2.6 mmol, 2.6 mL of 1 M solution) was added dropwise to the mixture via syringe under nitrogen atmosphere. The reaction temperature was brought to room temperature, and the mixture was further stirred for 4 h under nitrogen atmosphere. After completion of the reaction, the reaction mixture was acidified with acetic acid, diluted with water, and then extracted with 50 mL of $CH_2Cl_2$. The organic layer was washed twice with water and saturated saline solution. The organic layer was collected, dried over anhydrous $MgSO_4$, and concentrated under reduced pressure. The crude product was purified by column chromatography using hexane/EtOAc (20/80, v/v) to give the product as orange-pink crystalline solid (0.29 g, 75%). $^1$H NMR (400 MHz, $CDCl_3$): δ 6.97 (d, J=8.4 Hz, LH), 6.76-6.71 (m, 2H), 4.15-4.07 (m, 6H), 3.96 (t, J=6.0 Hz, 2H), 3.30 (s, 2H), 2.60 (s, 6H), 2.57-2.48 (m, 4H), 2.18-2.09 (m, 4H), 1.54 (s, 6H), 1.27-1.20 (m, 6H). $^{13}$C NMR (100 MHz, $CDCl_3$): δ 173.3, 173.1, 158.9, 150.0, 149.9, 145.7, 143.2, 131.4, 126.8, 120.9, 115.2, 114.3, 113.6, 84.3, 76.1, 68.6, 68.2, 60.6, 30.8, 24.8, 14.4, 13.7, 13.6. IR: 3296, 3255, 2958, 2933, 1728, 1532, 1467, 1392, 1316, 1265, 1247, 1184, 1084, 1013, 995, 761 $em^{-1}$. ESI-MS $[M+Na]^+$ ($C_{31}H_{37}BF_2I_2N_2O_6Na$) calcd, m/z=655.3. found, m/z=655.9. It shows absorption maximum at 539 nm and emission maximum at 553 nm in $CH_2Cl_2$ solution.

Polymer B.

BODIPY dye 4b (0.81 mmol, 0.677 g), BODIPY dye 6b (0.84 mmol, 0.531 g), and CuI (0.Q1 mmol, 4 mg) were added to a 100-mL round-bottom flask. Pd(PPh$_3$)$_4$ (10 mg) was added to the flask under a nitrogen atmosphere. When a degassed mixed solution of anhydrous THF (20 mL) and anhydrous diisopropylamine (20 mL) were added to the flask, the mixture was stirred under reflux for 24 h. After removal of the solvent, the residue was dissolved in methylene chloride and washed with water. The organic layer was collected, dried over anhydrous $MgSO_4$, and filtered.

Then the filtrate was concentrated under reduced pressure and added to 200 mL of ethanol to precipitate the polymer. The precipitated solid was collected, washed with ethanol, and dried under vacuum for 24 h at room temperature to obtain dark-violet solid (0.912 g). $^1$H NMR (400 MHz, CDCl$_3$): δ 6.96 (br, LH), 6.73 (br, 2H), 4.15-4.09 (br, 6H), 3.97 (br, 2H), 2.62 (s, 6H), 2.55-2.49 (br, 4H), 2.14-2.10 (br, 4H), 1.54 (s, 6H), 1.25-1.20 (br, 6H). $^{13}$C NMR (100 MHz, CDCl$_3$): δ 173.3, 173.1, 158.2, 150.0, 149.8, 143.3, 142.3, 131.7, 126.9, 120.9, 116.5, 114.2, 113.6, 89.0, 68.6, 68.2, 60.6, 31.1, 30.8, 24.8, 14.4, 13.8, 13.7. IR: 2932, 1729, 1513, 1471, 1436, 1390, 1311, 1264, 1228, 1161, 1087, 992, 882, 816, 760, 725, 694, 681 cm$^{-1}$. It displays absorption maximum at 665 nm and emission maximum at 683 nm in CH$_2$Cl$_2$ solution. OPC (THF, polystyrene standard), M$_n$=23 800 g/mol; polydispersity=1.9.

Polymers C, D and E

The synthetic route to polymers C, D and E is shown in FIG. 44 and detailed below.

9,9-Bis(6'-(hexylthio)hexyl)-2,7-diiodo-9H-fluorene (7a)

When 150 mL of degassed DMF was added to a 250-mL three-neck round-bottom flask containing 9,9-bis-(6'-bromohexyl)-2,7-diido9H-fluorene (2.69 mmol, 2 g), hexanethiol (8.07 mmol, 0.95 g), and K$_2$CO$_3$ (10.8 mmol, 1.48 g) under a nitrogen atmosphere, the mixture was stirred for 24 h at 40° C. under a nitrogen atmosphere. After completion of the reaction (which was monitored by TLC), the reaction mixture was concentrated under reduced pressure, added to water, and extracted with EtOAc. The organic layer was washed twice with water and saturated NaCl solution, dried over anhydrous MgSO$_4$, and concentrated under reduced pressure. The resulting cmde product was purified by silica gel column chromatography using hexane/EtOAc to obtain brown liquid (1.47 g, 67%). $^1$H NMR (400 MHz, CDCl$_3$): δ 7.65-7.61 (m, 4H), 7.38 (d, J=7.6, 2H), 2.44-2.35 (m, 8H), 1.89-1.85 (m, 4H), 1.53-1.47 (m, 4H), 1.4-1.22 (m, 20H), 1.15-1.04 (m, 8H), 1.03-0.84 (m, 6H). $^{13}$C NMR (100 MHz, CDCl$_3$): δ 152.5, 140, 136.3, 132.1, 121.7, 93.4, 55.5, 40.2, 32.4, 32.3, 31.7, 31.6, 29.9, 29.8, 29.7, 28.8, 23.8, 22.8, 14.3, 14.2. IR: 2924.9, 2853.4, 1593.4, 1567.8, 1448.0, 1409.4, 1393.4, 1377.0, 1279.1, 1255.6, 1054.0, 1003.3, 879.2, 808.1, 738.3 cm$^{-1}$. ESI-MS M$^4$ (C$_{37}$H$_{56}$I$_2$S$_2$) calcd, m/z=818.8. found, m/z=818.7.

Polymer C.

BODIPY dye 6b (0.126 mmol, 80 mg), 9,9-bis(6'(hexylthio)hexyl)-2,7-diiodo-9H-fluorene (7a) (0.115 mmol, 94 mg), and CuI (2 mg) were added to a 100-mL flask under a nitrogen atmosphere. In the glovebox, Pd(PPh$_3$)$_4$ 5 mg was added to the flask. When a degassed mixed solution of anhydrous THF (20 mL) and anhydrous diisopropylamine (20 mL) were added to the flask, the mixture was stirred under reflux for 24 h. After removal of the solvent, the residue was dissolved in methylene chloride 5 mL and added to 400 mL of ethanol to precipitate the polymer. The precipitated solid was filtered and washed with ethanol and hexane. The obtained solid was dried under vacuum for 24 h at room temperature to obtain dark-violet solid (0.147 g). $^1$H NMR (400 MHz, CDCl$_3$): δ 7.65-7.60 (br, 1H), 7.45-7.36 (m, 2H), 7.03-6.99 (br, 1H), 6.84-6.77 (br, 2H), 4.19-4.12 (br, 6H), 4.12-4.00 (br, 2H), 2.76 (s, 6H), 2.59-2.13 (M, 16H), 1.94 (br, 4H), 1.66 (s, 6H), 1.56-1.47 (br, 4H), 1.36-1.09 (m, 34), 0.86-0.84 (br, 6H). $^{13}$C NMR (100 MHz, CDCl$_3$): δ 173.3, 173.2, 158.9, 151.1, 149.9, 144.1, 140.7, 132.3, 131.8, 130.8, 125.5, 121.1, 120.2, 116.4, 114.4, 97.7, 68.7, 68.3, 60.7, 40.5, 32.4, 32.2, 31.6, 30.8, 29.8, 28.8, 24.8, 23.9, 22.7, 22.6, 14.5, 14.0, 13.9. IR: 2925.4, 1731:7, 1521.2, 1391.2, 1313.7, 1269.7, 1245.4, 1078.6, 1002.5, 820.6, 760.4 cm$^{-1}$. It shows absorption maximum at 606 nm and emission maximum at 641 nm in CH$_2$Cl$_2$ solution. OPC (THF, polystyrene standard), M$_n$=21 600 g/mol; polydispersity=2.1.

Polymer D.

BODIPY dye 6b (0.08 mmol, 50 mg), 1,4-diiodo-2,5-didecyloxybenzene (7b) (0.072 mmol, 46 mg), and CuI (2 mg) were added to a 100-mL flask under a nitrogen atmosphere. In the glovebox, Pd(PPh$_3$)$_4$ 5 mg was added to the flask. When a degassed mixed solution of anhydrous THF (20 mL) and anhydrous diisopropylamine (20 mL) were added to the flask, the mixture was stirred under reflux for 24 h. The polymer was purified in a way for polymer C to obtain dark-violet solid (0.073 g). $^1$H NMR (400 MHz, CDCl$_3$): δ 6.99 (br, 1H), 6.85-6.75 (br, 4H), 4.18-4.11 (br, 6H), 3.99-3.92 (br, 6H), 2.72 (s, 6H), 2.58-2.49 (m, 4H), 2.18-2.12 (br, 4H), 1.75 (br, 4H), 1.62 (s, 6H), 1.42 (br, 4H), 1.28-1.20 (br, 30H), 0.86-0.84 (br, 6H). $^{13}$C NMR (100 MHz, CDCl$_3$): δ 173.3, 173.1, 158.8, 153.4, 152.0, 149.9, 143.8, 142.3, 131.8, 127.1, 123.4, 121.0, 116.6, 116.0, 114.3, 113.8, 93.5, 87.4, 70.4, 69.5, 68.6, 68.3, 60.7, 33.9, 32.0, 30.9, 29.9, 29.8, 29.7, 29.54, 29.51, 29.4, 26.3, 26.2, 24.8, 22.9, 14.4, 14.4, 14.3, 13.8, 13.7. IR: 2924.6, 1726.2, 1526.4, 1314.8, 1009.7, 762.0 cm$^{-1}$. It exhibits absorption maximum at 635 nm and emission maximum at 657 nm in CH$_2$Cl$_2$ solution. OPC (THF, polystyrene standard), M$_n$=19200 g/mol; polydispersity=1.9.

Polymer E.

BODIPY dye 6b (0.126 mmol, 80 mg), 2,5-diiodo3-deeylthiophene (7c), (0.115 mmol, 54 mg), and CuI (2 mg) were added to a 100-mL flask under a nitrogen atmosphere. In the glovebox, Pd(PPh$_3$)$_4$ 5 mg was added to the flask. When a degassed mixed solution of anhydrous THF (20 mL) and anhydrous diisopropylamine (20 mL) were added to the flask, the mixture was stirred under reflux for 24 h. The polymer was purified in a way for polymer C to obtain dark-violet solid (0.106 g). $^1$H NMR (400 MHz, CDCl$_3$): δ 7.00-6.98 (m, 2H), 6.76 (br, 2H), 4.18-4.10 (br, 6H), 3.98 (br, 2H), 2.66 (s, 6H), 2.58-2.49 (m, 6H), 2.18-2.12 (br, 4H), 1.57 (br, 8H), 1.27-1.22 (br, 20H), 0.86-0.84 (br, 3H). $^{13}$C NMR (100 MHz, CDCl$_3$): δ 173.3, 173.1, 158.7, 150.2, 149.9, 147.4, 144.3, 142.6, 132.7, 131.8, 126.8, 123.1, 121, 116.2, 115.9, 114.3, 113.7, 89.1, 86.4, 76.9, 68.6, 68.2, 60.6, 32.1, 30.8, 30.3, 29.9, 29.8, 29.7, 29.6, 29.5, 24.8, 22.9, 19.9, 14.44, 14.41, 14.3, 13.9, 13.8. IR: 2921.1, 1731.0, 1516.5, 1391.3, 1312.0, 1246.0, 1170.0, 1000.0, 760.0, 724.7 cm$^{-1}$. It shows absorption maximum at 628 nm and emission maximum at 664 nm in CH$_2$Cl$_2$ solution. OPC (THF, polystyrene standard), M$_n$=15 700 g/mol; polydispersity=2.0.

Optical Properties of the Monomers and Polymers.

Figure 45:
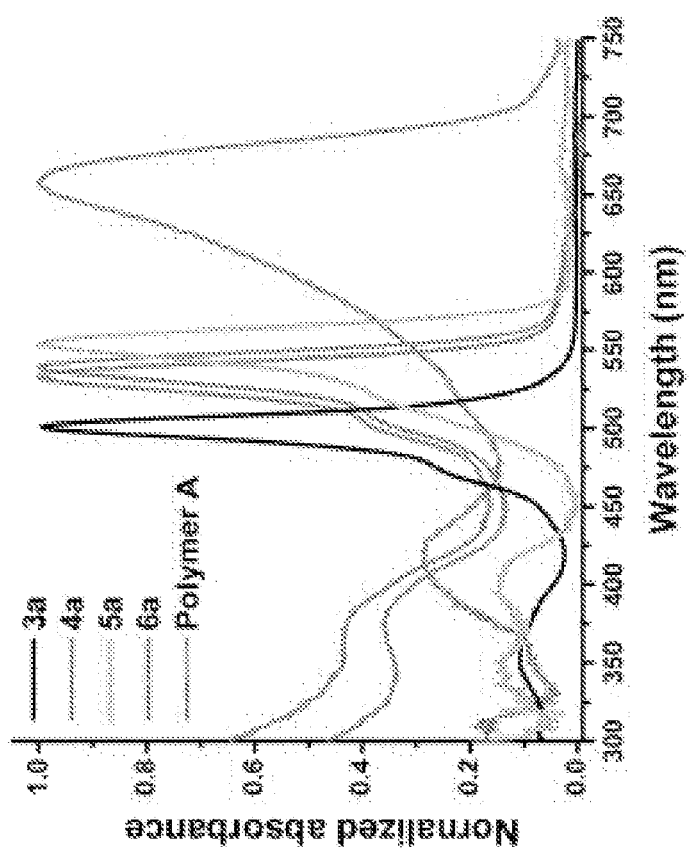
FIG. 45 shows absorption spectra for BODIPY dyes and polymers.
Figure 46:
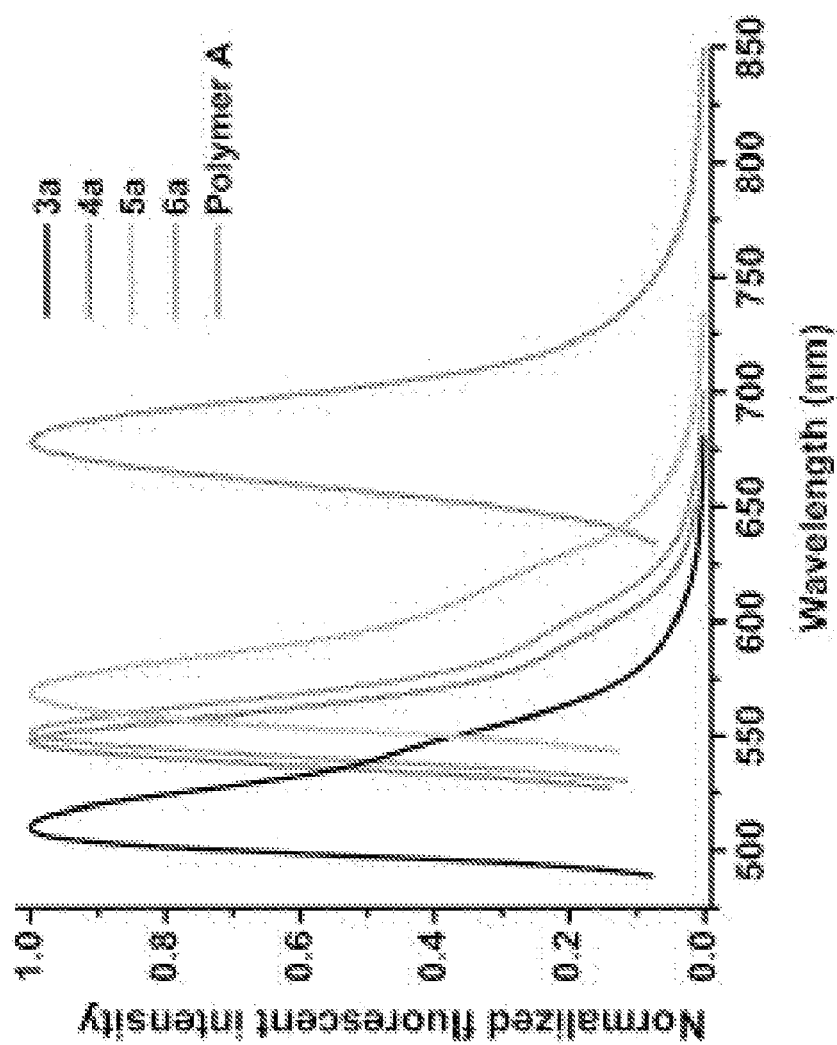
FIG. 46 shows fluorescence spectra for BODIPY dyes and polymers.
Figure 47:
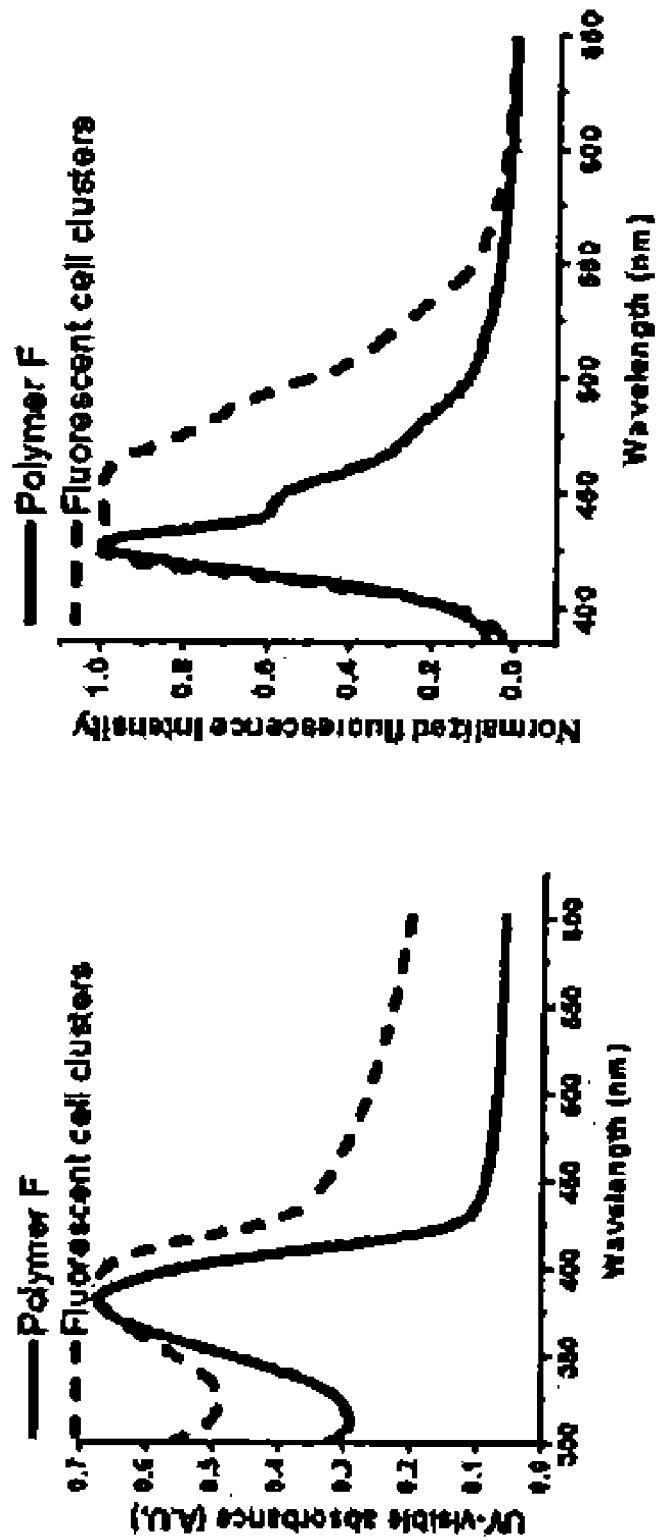
FIG. 47 shows UV-visible absorption (left) and fluorescent spectra (right) of polymer XXIV in the absence and presence of *E. coli* bacteria of ORN178 strain ($1 \times 10^8$ cells). Excitation wavelength is 370 nm.

The absorption properties of green emissive BODIPY dye (3a) are characterized by a strong S$_0$→S$_1$ (π-π*) transition at 501 nm and a weaker broad band around 350 nm ascribed to the S$_0$→S$_2$ (π-π*) transition (FIG. 45). Introduction of 2,6-diiodo substituents to the BODIPY core leads to large red shifts (33 and 38 nm) of both the UV absorption and fluorescence maxima, respectively, significantly depressing the fluorescence quantum yield because of efficient intersystem crossing induced by the heavy atom effect of iodine (FIG. 45, Table 10). 2,6-Diethynylation of 2,6-diiodotetramethyl BODIPY (4a) results in a little red shift due to the enhanced conjugation. However, polymer A emits in the deep red region at 678 nm and exhibits pronounced bathochromic shifts (158 and 168 nm) of both the absorption and the fluorescence maxima relative to the initial BODIPY dye (3a) because of its significant extension of π-conjugation (FIG. 46 and Table 10). Polymer B displays an absorption maximum at 665 nm and fluorescence maximum at 683 nm, a slight red-shift relative to polymer A. The absorption peaks of conjugated polymers become broader than BODIPY monomers as a result of the extended π-conjugation (FIG. 46). BODIPY dyes (3a, 3b, 5a, 5b, 6a, and 6b) show fluorescence lifetimes of several nanoseconds (Table 10). However, the diiodo-functionalized BODIPY dyes (4a and 4b) display much shorter fluorescence lifetimes (ranging from 0.08 to 0.13 ns), consistent with their decreased quantum yields because of efficient intersystem crossing induced by the heavy atom effect of iodine (Table 10).

TABLE 10

Absorption and Emission Maxima and Quantum Yields of BODIPY Dyes and Polymers in Methylene Chloride Solution.

| | BODIPY dyes or polymers | | | | |
|---|---|---|---|---|---|
| | 3a | 4a | 5a | 6a | polymer A |
| absorption maxima (nm) | 501 | 533 | 553 | 538 | 659 |
| emission maxima (nm) | 510 | 548 | 569 | 552 | 678 |
| quantum yield (%) | 76 | 5.8 | 71 | 63 | 21 |
| fluorescence lifetime (ns) | 3.8 | 0.13 | 4.5 | 4.2 | 3.8 |

| | BODIPY dyes or polymers | | | | |
|---|---|---|---|---|---|
| | 3b | 4b | 5b | 6b | polymer B |
| absorption maxima (nm) | 502 | 534 | 554 | 539 | 665 |
| emission maxima (nm) | 511 | 549 | 570 | 553 | 683 |
| quantum yield (%) | 81 | 5.8 | 79 | 67 | 23 |
| fluorescence lifetime (ns) | 4.1 | 0.08 | 5.2 | 5.9 | 3.7 |

[a]Quantum yields of BODIPY dyes and polymeric dyes were determined by use of fluorescein (quantum yield of 0.85 in 0.1N NaOH) as a standard.[13-16]

Arylation at the meso position has no significant effect on the absorption and emission maxima of BODIPY dyes since the arylated moiety is not coplanar with the BODIPY core because of steric hindrance, although the substitution position is structurally different (Table 10). As a result, two different BODIPY monomer pairs (4a-4-b and 6a-6b) each have only 1 nm difference between their respective absorption or emission spectral maxima. However, the absorption and emission maxima of polymer B are somewhat more red-shifted relative to those of polymer A, which might arise from amplification effect of conjugated polymers. The quantum yields of the meso-phenyl BODIPY dyes (3b, 5b, and 6b) are a little higher than those of the corresponding less substituted analogues (3a, 5a, and 6a) (Table 10). The difference might result from reduced free rotation of the phenyl group in the more substituted compounds and a subsequent decrease in loss of energy from the excited states through nonirradiative molecular motions. Polymers A and B displays similar fluorescence lifetimes to their starting BODIPY dyes (3a and 3b) (Table 10).

Incorporation of different band gap monomers such as fluorene, benzene, and thiophene units into the backbone of poly(2,6-BODIPY-ethynylene) results in the copolymers with different red emissions. Fluorescence maxima of the copolymers with fluorene, benzene, and thiophene units are 641, 657, and 664 nm, respectively (Table 11), which is consistent with their band gap energy differences (fluorine>benzene>thiophene). Introduction of the thiophene unit to poly(2,6-BODIPY-ethynylene) significantly reduces the fluorescence quantum yield of the copolymer and shortens fluorescence lifetime of the copolymer due to efficient intersystem crossing induced by the heavy atom effect of sulfur.

TABLE 11

Absorption and Emission Maxima and Quantum Yields of BODIPY-Based Copolymers in Methylene Chloride Solution

| | BODIPY-based copolymers | | |
|---|---|---|---|
| | polymer C | polymer D | polymer E |
| absorption maxima (nm) | 606 | 635 | 628 |
| emission maxima (nm) | 641 | 657 | 664 |
| quantum yield (%) | 25 | 24 | 6 |
| fluorescence liftime (ns) | 2.8 | 3.6 | 0.23 |

[a]Quantum yields of BODIPY dyes and polymeric dyes were determined by use of fluorescein (quantum yield of 0.85 in 0.1N NaOH) as a standard.[13-16]

Example 15

Prevention of Nonspecific Interactions of Conjugated Glycopolymers with Other Proteins Well-defined poly(ethylene glycol) as tethered spacers between carbohydrate and polymer backbones are used to enhance water-solubility of conjugated glycopolymers, and prevent the nonspecific interactions of BODIPY-based conjugated glycopolymers with other proteins. Histone (from calf thymus, Type II-A), hemoglobin (from bovine blood), myoglobin (from horse heart), lysozyme (from chicken egg white), cytochrome c (from bovine heart), albumin (from bovine serum), and sticking protein fibrinogen are used to test whether there are nonspecific interactions of the conjugated glycopolymers with these proteins by measuring UV-Visible and fluorescent spectra of the conjugated glycopolymers in 0.1 M phosphate buffer (pH 7.2) in the absence and presence of different concentrations of each protein above (from 1.0 μM to 1.0 mM). The non-specific interactions of the conjugated glycopolymers with other proteins can result in changes of fluorescent intensity of the conjugated glycopolymers.

Example 16

Detection of Escherichia coli

Fluorene-based α-mannose bearing conjugated glycopolymer (polymer XXIV) and α-mannose bearing conjugated poly(p-phenylene) (polymer XXX) have been used as bioimaging materials for detection of E. coli bacteria.

Two E. coli strains, ORN178 and ORN208, were used for testing and control experiments to investigate the specific binding of a-mannose-bearing polymers XXIV and XXX to FimH protein of E. coli. The ORN178 strain expresses the wild-type type 1 pili that selectively bind to α-mannose, whereas the ORN208 strain is deficient of the fimH gene and expresses abnormal type 1 pili that fail to mediate specific binding to α-mannose. Incubation of polymer XXIV or XXX with the ORN178 strain resulted in formation of fluorescently stained bacteria clusters from which the polymer was not removed by rinsing and separation. However, Polymers XXIV and XXX failed to bind to ORN208 strain and polymers XXIII and XXXI did not bind to the ORN178 strain, 11 which indicates that α-mannose-bearing polymers XXIV and XXX selectively bind to ORN178 through multivalent interactions. Results show that fluorescently-stained bacterial cluster and individual cells by glycopolymer XXIV can easily be observed. Strong multivalent interactions between polymer XXIV and bacterial pili result in significant red shifts in both absorption and emission spectral maxima because long, flexible poly(ethylene glycol) tethered spacers, significantly reduce steric binding hindrance of the polymeric mannose residues to bacterial pili (FIG. 25). The red shift of the polymer fluorescence was also observed in fluorescent imaging of fluorescently-stained bacterial cluster where there is a big green spot in the center of the image.

Example 17

Use of BODIPY-Based Conjugated Glycopolymers to Sensitively Detect *Escherichia coli*

BODIPY-based fluorescent conjugated glycopolymers as bioimaging materials are used to detect *Escherichia coli* (*E. coli*). Type 1 pili in *E. coli* are filamentous proteinaceous appendages composed of FimA, FimF, FimG, and FimH proteins. FimH protein is uniquely responsible for the binding to α-D-mannose. Two *E. coli* strains, ORN178 and ORN208, will be used for testing and control experiments since the ORN178 strain expresses wild-type 1 pili that selectively binds to α-D-mannose. In contrast, the ORN208 strain is deficient of the fimH gene and expresses abnormal type 1 pili that fail to mediate α-D-mannose-specific binding. *E. coli* bacterial cells will be grown and prepared according to the published procedure. (*Biomacromolecules* 2006, 7, (9), 2470-2474). Other bacterial samples such as *Campylobacter Jejuni* and *Yersinia enterocolitica* are obtained from American Type Culture Collection (ATCC) Global Bioresource Center. The cultures are grown in TYG medium (5% tryptone, 2.5% yeast extract, 1% glucose) at 37° C. for 24 to 48 h with shaking at 200 rpm. Bacterial cells are collected by centrifugation at 20,000 g, washed and resuspended in phosphate-buffered saline (PBS) or appropriate buffer for further studies.

A 1.0 mL aliquot of *E. coli* ORN178 cells (with different cell number) in 0.1 M phosphate buffer (pH 7.2) with 1.0 mM $CaCl_2$ and 1.0 mM $MnC_{12}$ are incubated with 5-20 µg aliquot of BODIPY-based fluorescent conjugated glycopolymers for one half to two hours with gentle shaking, centrifuged at 10,000 g for 30 minutes, and washed six times with 0.1 M phosphate buffer. The final cell pellet is resuspended in 0.1 M phosphate buffer (pH 7.2). Absorption and fluorescent spectra of BODIPY-based conjugated glycopolymers are recorded in 0.1 M phosphate buffer (pH 7.2) with 1.0 mM $CaCl_2$ and 1.0 mM $MnCl_2$ in the absence and presence of different amounts from (a few to $10^9$) of bacterial cells. It is expected that strong interactions of *E. coli* bacteria with BODIPY-based conjugated glycopolymers bearing α-mannose residues will result in the formation of fluorescently-stained bacterial clusters or cells. A fluorescent confocal microscope is used to capture images of these fluorescently-stained bacterial clusters or cells, and determine detection limit (number of bacterial cells per mL) of the imaging materials. Cooperative multiple bindings of *E. coli* bacteria with α-mannose-bearing glycopolymers are tested by adding free α-mannose to the phosphate buffer containing fluorescently stained bacteria clusters. Measurements can then be made of the sufficient level of concentration of free α-mannose needed (relative to the concentration of the α-mannose-bearing glycopolymers) to make fluorescently stained bacteria clusters completely disappear. This will enable the study of the strength of the cooperative multiple bindings of *E. coli* with the glycopolymers bearing different densities and spacing of α-mannose ligands.

Control experiments are conducted using the ORN208 cells instead of the ORN178 cells to test the selectivity of BODIPY-based conjugated glycopolymers and investigate whether there are nonspecific interactions of the conjugated glycopolymers with the ORN208 cells as the ORN208 strain is unable to mediate α-mannose-specific binding.

*E. coli* is detected in contaminated samples by incubating α-mannose-bearing conjugated glycopolymers with strain ORN178 which is placed as a contaminant into solutions that include sheep erythrocytes and serum. *E. coli* is detected in solution containing different bacteria of *E. coli* and *Campylobacter Jejuni* and *Yersinia enterocolitica*. The testing is conducted in a manner similar to that of pure bacterial samples.

Anticipated results: BODIPY-based conjugated glycopolymers will circumvent the problem of residual blue fluorescence, (blue haze) that tends to emanate from biological fluids because the deep-red and near-infrared emissive polymeric dyes with emission wavelengths ranging from 680 nm to 900 nm have low background absorption, low scattering and cheap illumination sources. Strong multivalent interactions of a-mannose-bearing conjugated glycopolymers with *E. coli* strain ORN178 will result in fluorescently-stained bacterial clusters or fluorescently-stained bacterial cells, which will depend on number of bacterial cells. BODIPY-based conjugated glycopolymers bearing oligomannose or hydrophobic aromatic α-mannose residues will have much higher sensitivity than those bearing α-mannose residues because the FimH adhesin of Type 1 fimbriae of *E. coli* possesses an extended combining site and a hydrophobic region next to the carbohydrate-binding site of FimH, and displays a considerably higher affinity to oligomannose and hybrid type such as Manα3Manβ4GlcNAc and Manα6 (Manα3)Manα6(Manα3)Man, and to hydrophobic aromatic α-mannose. BODIPY-based conjugated glycopolymers bearing longer oligo(ethylene glycol) tethered spacers (with repeated unit (m)>10, up to 43) will be highly soluble in aqueous solution and display much stronger multivalent interactions with bacterial pili due to less steric binding hindrance of carbohydrates to the bacterial pili, 10 which might allow for sensitive detection of a few bacterial cells. BODIPY-based conjugated glycopolymers bearing galactose or N-acetylgalactosamine residues will have strong interactions with *Yersinia enterocolitica* which is reported to selectively interact with galactose and N-acetylgalactosamine of native small intestinal mucin through a plasmid-mediated process. BODIPY-based conjugated glycopolymers bearing fucose residues will have strong interactions with *Campylobacter jejuni* whose binding to intestinal epithelial cells is achieved through fucosylated carbohydrate epitopes.

Example 18

Use of BODIPY-Based Conjugated Glycopolymers to Detect Influenza Virus

α-Sialic acid-bearing fluorescent conjugated glycopolymers are used to detect influenza virus. Influenza virus is roughly globular in shape and approximately 1000 Å in diameter. The outer surface of the virus contains the protein hemagglutinin (RA) and neuraminidase. The HA molecules aggregate into triangular clusters, distributing irregularly on the surface of the virus and the center-to-center distance between the clusters is 95-150 Å. The binding of the HAs to sialic acid (N-acetylneuraminic acid) groups present on cell surface glycoproteins and glycolipids initiates infection of a red blood cell by influenza virus and drives the cells to aggregate into massive clusters. The subtypes found in avian influenza virus binds preferentially to α-Sia(2→3)-Gal which predominates in avian gastrointestinal tract where viruses replicate. Human influenza virus prefers α-Sia(2→6)-Gal.

Influenza virus A/AA/6/60 (H₂N₂) strain passaged in mice and another passaged in chickens is obtained from Department of Public Health, University of Michigan, Ann Arbor, Mich., and propagated in embryonated chicken eggs using standard methods. α-Sialic acid-bearing glycopolymer stock solution is diluted with 0.1 M phosphate buffer (pH 7.2). When 1.0 mL of this solution is transferred to a 2.0 mL Eppendorf tube, 5-20 µL of the stock solution of Influenza Virus A or B is added to the tube, mixed and incubated at 4° C. for 0.5-2 hours. The UV-visible absorption and fluorescent spectra are recorded and compared with the same concentration of the mother solution. Fluorescent imaging of fluorescent clusters of the sialic acid-bearing glycopolymers with influenza virus is conducted a similar way to that of the fluorescently stained *E. coli* clusters.

Anticipated results: BODIPY-based conjugated glycopolymers bearing NeuAcα-2,6Galβ1,4GlcNAcβ or NeuAcα-2,6Galβ1,4GlcNAcβ residues (Table 3) will display strong interactions with human influenza virus while BODIPY-based conjugated glycopolymers bearing NeuAcα-2,3Galβ1,4GlcNAcβ or NeuAcα-2,3Galβ1,4GlcNAcβ residues (Table 3) will not have any interactions with human influenza.

The invention claimed is:

1. A polymer is according to formula (I):

(I)

wherein each -A- is independently selected from —AR—,

——————═══— AR ——————═══—,

——————═══— AR ——————═══—, or

——————═══— ——————═══— AR ——————═══—;

wherein each —AR— is flourenyl;

wherein each $R_3$ is independently selected from R, alkyl, aryl or heteroaryl wherein each $R_2$ and $R_4$ are independently selected from alkyl or H;

wherein each $R_1$ and $R_5$ are independently selected from hydrogen, alkyl, or ——————═══— AR;

wherein each $R_0$ is —F, —OR, —R, aryl, heteroaryl,

——————═══— R, ——————═══— Aryl, or

——————═══— -Heteroaryl;

wherein each R is independently selected from —H, —(CH₂)ₘR₁₀, —(CH₂)ₘCOO(CH₂)ₚCH₃, —(CH₂)ₘSO₃Na, —(CH₂)ₘPO₃Na, —(CH₂)ₘN(CH₃)₃⁺ Br⁻, —(CH₂)ₘCOH(CH₂)ₚCH₃, —(CH₂)ₘOR₁₀, —(CH₂)ₘOR₈, —CH₂CH₂(OCH₂CH₂)ₘOR₁₀, —CH₂CH₂(OCH₂CH₂)ₘOR₈, —CH₂CH₂(OCH₂CH₂)ₘSR₈, or and
wherein each $R_8$ is independently selected from a carbohydrate residue;
and wherein each $R_{10}$ is independently selected from hydrogen, alkyl, heteroalkyl, hydroxy, amino, ammonic acid, thiol, carboxylic acid, nitrile, azide, ethynylene, halo, and tosylate;
wherein m is from 0 to 100;
wherein n is from 2 to 300 and
wherein p is from 0 to 20.

2. A polymer according to claim 1, wherein each $R_3$ is independently selected from wherein each $R_F$ is independently selected from R, OR, hydrogen, alkyl, heteroalkyl, aryl, heteroaryl, hydroxy, amino, thiol, carboxylic acid, nitrile, azide or halo; and
wherein each R is independently selected from —H, —(CH₂)ₘR₁₀, —(CH₂)ₘCOO(CH₂)ₚCH₃, —(CH₂)ₘSO₃Na, —(CH₂)ₘPO₃Na, —(CH₂)ₘN(CH₃)₃⁺ Br⁻, —(CH₂)ₘCOH(CH₂)ₚCH₃, —(CH₂)ₘOR₁₀, —(CH₂)ₘOR₈, —CH₂CH₂(OCH₂CH₂)ₘOR₁₀, —CH₂CH₂(OCH₂CH₂)ₘOR₈, —CH₂CH₂(OCH₂CH₂)ₘSR₈, or and
wherein each $R_8$ is independently selected from a carbohydrate residue;
and wherein each $R_{10}$ is independently selected from hydrogen, alkyl, heteroalkyl, hydroxy, amino, ammonic acid, thiol, carboxylic acid, nitrile, azide, ethynylene, halo, and tosylate.

3. A polymer according to claim 1, wherein each $R_1$ and $R_5$ is independently —CH₃ or —CH₂CH₃.

4. A polymer according to claim 1, wherein each $R_0$ is independently selected from

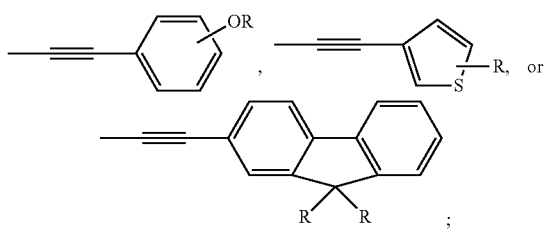
,
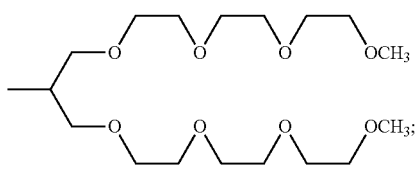

wherein each R is independently selected from —H, —$(CH_2)_m R_{10}$, —$(CH_2)_m COO(CH_2)_p CH_3$, —$(CH_2)_m SO_3Na$, —$(CH_2)_m PO_3Na$, —$(CH_2)_m N(CH_3)_3^+ Br^-$, —$(CH_2)_m COH(CH_2)_p CH_3$, —$(CH_2)_m OR_{10}$, —$(CH_2)_m OR_8$, —$CH_2CH_2(OCH_2CH_2)_m OR_{10}$, —$CH_2CH_2(OCH_2CH_2)_m OR_8$, —$CH_2CH_2(OCH_2CH_2)_m SR_8$, or and wherein each $R_8$ is independently selected from a carbohydrate residue;

and wherein each $R_{10}$ is independently selected from hydrogen, alkyl, heteroalkyl, hydroxy, amino, ammonic acid, thiol, carboxylic acid, nitrile, azide, ethynylene, halo, and tosylate.

* * * * *